US011464831B2

(12) United States Patent
Bicalho

(10) Patent No.: US 11,464,831 B2
(45) Date of Patent: *Oct. 11, 2022

(54) COMPOSITIONS AND METHODS USING IL-8 FOR IMPROVING HEALTH OF MAMMALS

(71) Applicant: Cornell University, Ithaca, NY (US)

(72) Inventor: Rodrigo Carvalho Bicalho, Dryden, NY (US)

(73) Assignee: Cornell University, Ithaca, NY (US)

( * ) Notice: Subject to any disclaimer, the term of this patent is extended or adjusted under 35 U.S.C. 154(b) by 7 days.

This patent is subject to a terminal disclaimer.

(21) Appl. No.: 16/567,991

(22) Filed: Sep. 11, 2019

(65) Prior Publication Data

US 2020/0078444 A1    Mar. 12, 2020

Related U.S. Application Data

(63) Continuation-in-part of application No. 15/541,126, filed as application No. PCT/US2016/012154 on Jan. 5, 2016, now Pat. No. 10,500,253.

(60) Provisional application No. 62/729,832, filed on Sep. 11, 2018, provisional application No. 62/099,643, filed on Jan. 5, 2015.

(51) Int. Cl.
  *A61K 38/20* (2006.01)
  *A61K 9/00* (2006.01)
  *A61P 15/14* (2006.01)

(52) U.S. Cl.
  CPC ........ *A61K 38/2053* (2013.01); *A61K 9/0019* (2013.01); *A61K 9/0034* (2013.01); *A61P 15/14* (2018.01)

(58) Field of Classification Search
  CPC . A61K 38/2053; A61K 9/0019; A61K 9/0034
  See application file for complete search history.

(56) References Cited

U.S. PATENT DOCUMENTS

| | | | |
|---|---|---|---|
| 3,108,875 A | 10/1963 | Bell | |
| 5,624,670 A * | 4/1997 | Kelly | A61P 15/04 424/85.2 |
| 6,013,252 A | 1/2000 | Terao et al. | |
| 6,027,908 A | 2/2000 | Saito et al. | |
| 6,114,510 A | 9/2000 | Scholz et al. | |
| 2005/0232898 A1 | 10/2005 | Canning et al. | |
| 2006/0233748 A1 | 10/2006 | Merzouk et al. | |
| 2010/0112087 A1 | 5/2010 | Harrison et al. | |
| 2010/0113384 A1 | 5/2010 | Ametaj | |
| 2010/0298245 A1 | 11/2010 | Aydt et al. | |
| 2014/0206752 A1 | 7/2014 | Afeyan et al. | |

FOREIGN PATENT DOCUMENTS

| | | |
|---|---|---|
| CN | 1225016 A | 8/1999 |
| CN | 101253934 A | 9/2008 |
| EP | 0543476 A1 | 5/1993 |
| RU | 2405376 C2 | 12/2010 |
| RU | 2012128258 A | 1/2014 |
| WO | 02/064167 A2 | 8/2002 |
| WO | 2014/195413 A1 | 12/2014 |

OTHER PUBLICATIONS

Sun et al., Medicine (Baltimore), 2016, vol. 95(52): e5537.*
Oliveira et al., J. Dairy Sci., 2016, vol. 99(11):9174-9183.*
Watanabe et al., Can. J. Vet. Res., 2008, vol. 72(3):291-296.*
Kimura et al., J. Dairy Sci., 2002, vol. 85(3):544-550.*
Watanabe, et al., Effects of intramammary infusions of interleukin-8 on milk protein composition and induction of acute-phase protein in cows during mammary involution, The Canadian Journal of Veterinary Research, 2008, vol. 72, pp. 291-296.
Kimura, et al., Decreased Neutrophil Function as a Cause of Retained Placenta in Dairy Cattle, Journal of Dairy Science, 2002, vol. 85, No. 3, pp. 544-550.
Neves, et al., Use of leukocytes as treatment for endometritis in mares experimentally infected with *Streptococcus equi* subsp. *zooepidemicus*, Animal Reproduction Science, Feb. 20, 2006, vol. 97, pp. 314-322.
Zerbe, et al., Development and comparison of in vivo and in vitro models for endometritis in cows and mares, Theriogenology, 2003, vol. 60, pp. 209-223.
Lyubimov et al., Effect of mastitis on milk productivity activity of cows and fitness for processing, Vestnik Kazanskogo GAU, 2013, vol. 2, No. 28, pp. 130-134.
Sarber et al., Chemotactic Activities in Nonmastitic and Mastitic Mammary Secretions: Presence of Interleukin-8 in Mastitic but Not Nonmastitic Secretions, Clinical and Diagnostic Laboratory Immunology, Jan. 1998, vol. 5, No. 1, pp. 82-86.
Muhaghegh-Dolatabady, Single Nucleotide Polymorphism in the Promoter Region of Bovine Interleukin 8 Gene and its Association with Milk Production Traits and Somatic Cell Score of Holstein Cattle in Iran, Iranian Journal of Biotechnology, Nov. 25, 2014, vol. 12, No. 3, pp. 36-41.
Galvao et al., Association between interieukin-8 receptor-alpha (CXCR1) polymorphism and disease incidence, production, reproduction, and survival in Holstein cows, Journal of Dairy Science, Apr. 2011, vol. 94, No. 4, pp. 2083-2091.

(Continued)

*Primary Examiner* — Xiaozhen Xie
(74) *Attorney, Agent, or Firm* — Hodgson Russ LLP

(57) ABSTRACT

The present disclosure provides compositions and methods for improving reproductive health of mammals and increasing milk production from female mammals. The methods involve administering an effective amount of IL-8 to a female mammal such that the reproductive health of the mammal is improved, or milk production from the mammal is increased, or the fat content of the milk is increased, or the dry matter intake of the mammal is improved, or a combination thereof occurs. In another aspect the disclosure includes prophylaxis and/or therapy of uterine conditions by administering IL-8 to a female mammal. The disclosure includes but is not necessarily limited to systemic administration of the IL-8. Kits for carrying out the methods are also included.

12 Claims, 19 Drawing Sheets

Specification includes a Sequence Listing.

(56) References Cited

OTHER PUBLICATIONS

Rains, J. L. et al., Hyperketonemia Increases MCP-1 and IL-8 Secretion, LFA-1 and ICAM-1 Expression, and Monocyte Adhesion to Endothelial Cells, 70th Annual Meeting of the American Diabetes Association, Jun. 2010, vol. 59, No. Suppl. 1, p. A240.

Zhang, M. et al., Genetic Polymorphism of IL8 Gene and Its Association with Milk Traits and SCS in Holstein Imported from Australia, Acta Veterinaria et Zootechnica Sinica, Dec. 31, 2013, vol. 44, No. 5, pp. 690-696.

Le Marechal, C. et al., Mastitis Impact on Technological Properties of Milk and Quality of Milk Products—A Review, Dairy Sci. & Technol, Mar. 11, 2011, vol. 91, pp. 247-282.

Xue, J., The Impact of Subclinical Ketosis on Mastitis, Antioxygen and Immune Function in Dairy Cow, Chinese Master's Theses Full-text Database Agriculture Science and Technology, Jun. 15, 2013, vol. 6, pp. D050-D602.

Takahashi, H., et al.. Effect of Intramammary Injection of RbIL-8 on Milk Levels of Somatic Cell Count, Chemiluminescence Activity and Shedding Patterns of Total Bacteria and *S. aureus* in Holstein Cows with Naturally Infected-subclinical Mastitis, J. Vet. Med., Feb. 2005, vol. 52, No. 1, pp. 32-37.

Nikitina, T.N., et al., Immunoadjuvant activity of cytokines, BIOpreparations. Prevention, Diagnosis, Treatment, 2008, vol. 1, No. 29, pp. 16-19.

Cotton, J.A., et al., Interleukin-8 in gastrointestinal inflammation and malignancy: induction and clinical consequences. International Journal of Interferon, Cytokine and Mediator Research, May 10, 2016, vol. 8, pp. 13-34.

\* cited by examiner

COMPOSITIONS AND METHODS USING IL-8 FOR IMPROVING HEALTH OF MAMMALS

CROSS-REFERENCE TO RELATED APPLICATIONS

This application claims priority to U.S. provisional application No. 62/729,832, filed Sep. 11, 2018. This application is also a continuation-in-part of U.S. patent application Ser. No. 15/541,126, filed Jun. 30, 2017, now U.S. Pat. No. 10,500,253, which is a national phase of international patent application no. PCT/US2016/012154, filed Jan. 5, 2016, which claims priority to U.S. provisional application No. 62/099,643, filed Jan. 5, 2015, the entire disclosures of each of which are incorporated herein by reference.

FIELD

This disclosure relates generally to administering Interleukin-8 (IL-8) to mammals, including but not necessarily limited to female bovine mammals, and including but not necessarily limited to systemic administration of IL-8.

BACKGROUND

As the world population grows and more importantly as the per capita purchasing power parity increases, the demand for animal protein (milk, meat, and eggs) will steadily and inevitably grow; to avoid inflationary pressures the supply of animal protein products must increase significantly and sustainably with minimal expansion in agricultural land use. Additionally, it has been reported that feed efficiency is the single greatest factor contributing to variation in the carbon footprint, and that improving efficiency of feed conversion can reduce greenhouse gas emissions both via reductions in enteric methane and manure output. Post-partum uterine diseases such as metritis, endometritis, and retained placenta are important for animal welfare reasons, contributing to cow discomfort and elimination from the herd; coupled with profoundly affected reproductive performance, reduced milk yield and treatment costs. Metritis and endometritis are commonly associated with mixed bacterial infection of the uterus, including *E. coli*, *T. pyogenes*, and *F. necrophorum* (Bicalho et al., 2012). A contributory factor increasing susceptibility to uterine diseases is the immunosuppression faced by cows during the periparturient period (Drackley, 1999; Cai et al., 1994; Kimura et al., 1999; Hammon et al., 2006; Galvao et al., 2010). There is an ongoing and unmet need for improved approaches targeted to prophylaxis and therapy of post-partum diseases, as well as for improving reproductive performance and milk production, and for increasing intake of dry matter. The present disclosure addresses these and other needs.

SUMMARY

The present disclosure includes producing each and every result, singularly, and all combinations thereof, that are described herein. In embodiments, the disclosure relates to administration of IL-8 systemically, including by intravenous administration, and also to intravaginal and intrauterine administration. In embodiments, the disclosure provides for intravenous administration of IL-8 to male or female bovine animals. The disclosure demonstrates, among other effects, use of intravenous IL-8 to improve lactation performance, as evidenced by increased milk production, as well as improved production of fat corrected milk (FCM) and energy corrected milk (ECM). Such effects are demonstrated to be durable, and can be elicited using a single IL-8 administration. The disclosure also demonstrates a beneficial increase in insulin resistance that is elicited by intravenous IL-8 administration. The disclosure also demonstrates changes in dry matter intake that is correlated with IL-8 administered intravenously and as an intra-uterine administration.

The disclosure includes all forms of IL-8 described herein, and all methods of producing it, including but not limited to all cloning intermediates, plasmids, purification tags, including but not necessarily limited to poly-histidine tags, and amino acids that may be included in a contiguous IL-8 polypeptide that are encoded by a plasmid or other vector, but are not part of endogenously produced IL-8, such as amino acids encoded by polycloning sites, or other features of protein expression vectors that result in incorporation of additional amino acids into the IL-8 polypeptide. Thus, in an embodiment, the disclosure includes standardized cloning, production, and purification of rbIL-8 from bacterial culture, and demonstrates that that the purification method presented provides recombinant bovine IL-8 that is biologically active and safe.

DESCRIPTION OF THE FIGURES

Part I Figures

Part II Figures

Figure 4:
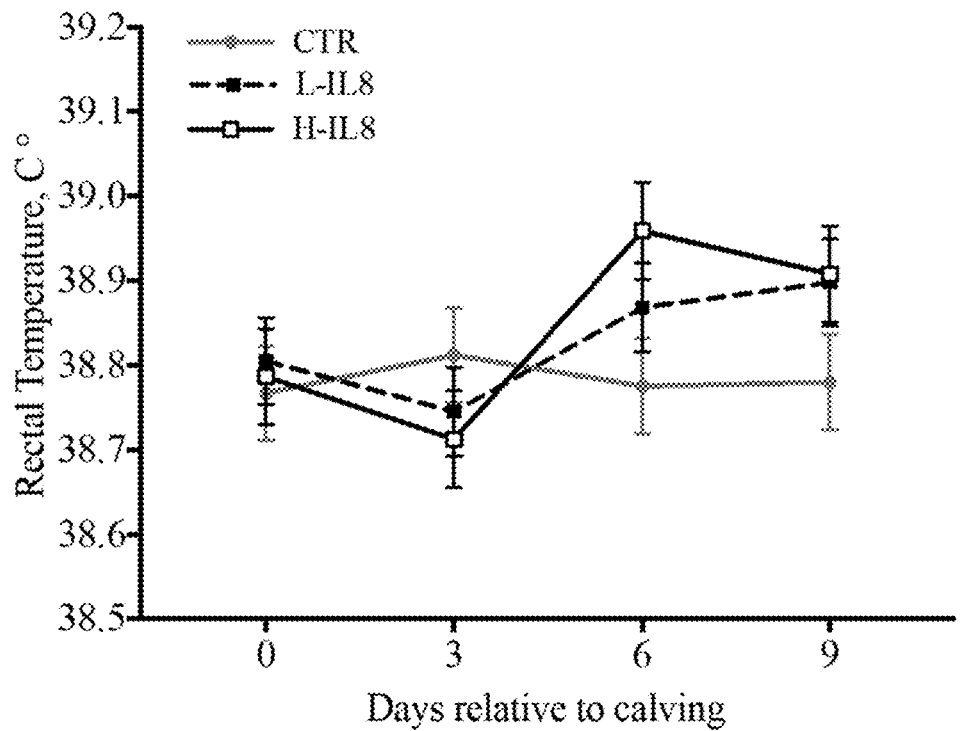

FIG. 4. Rectal temperature (° C.) of cows treated with different rbIL-8 doses and controls from study 1. Postpartum cows (n=213) were randomly allocated into one of three intrauterine treatment groups: control (CTR; 250 mL of saline solution), low-dose (L-IL8; 11.25 g of rbIL-8 diluted in 250 mL of saline solution), and high-dose (H-IL8, 1,125 μg of rbIL-8 diluted in 250 mL of saline solution). Results are presented at LSM±SEM. *$P \leq 0.05$.

Figure 5:
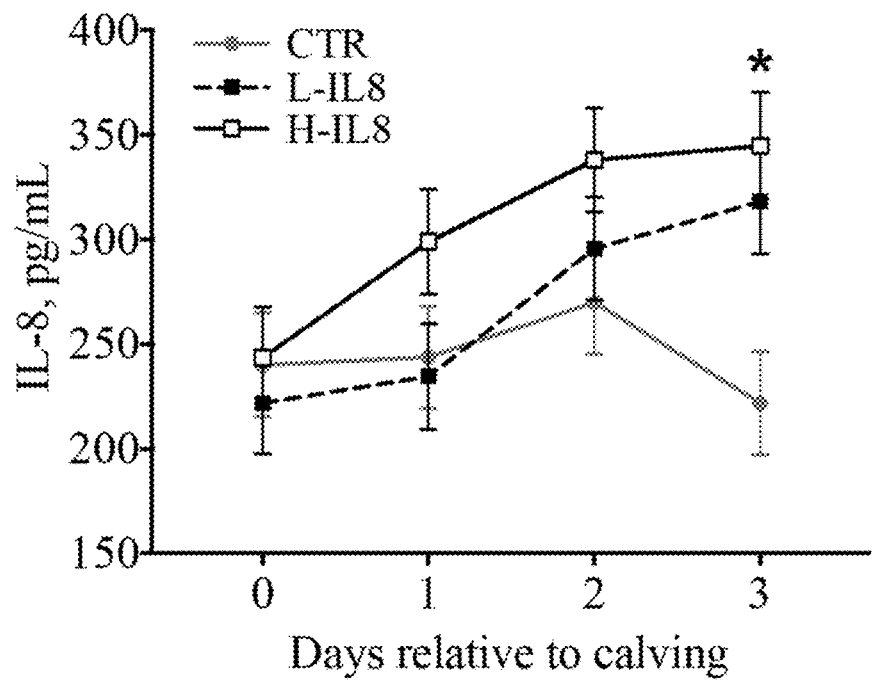

FIG. 5. Interleukin-8 (IL-8) plasma concentrations of cows treated with different rbIL-8 doses and controls from study 1. Postpartum cows (n=213) were randomly allocated into one of three intrauterine treatment groups: control (CTR; 250 mL of saline solution), low-dose (L-IL8; 11.25

μg of rbIL-8 diluted in 250 mL of saline solution), and high-dose (H-IL8, 1,125 μg of rbIL-8 diluted in 250 mL of saline solution). Blood samples were harvested from a subset of cows (20/treatment group). Results are presented at LSM±SEM. *P≤0.05.

Figure 6:
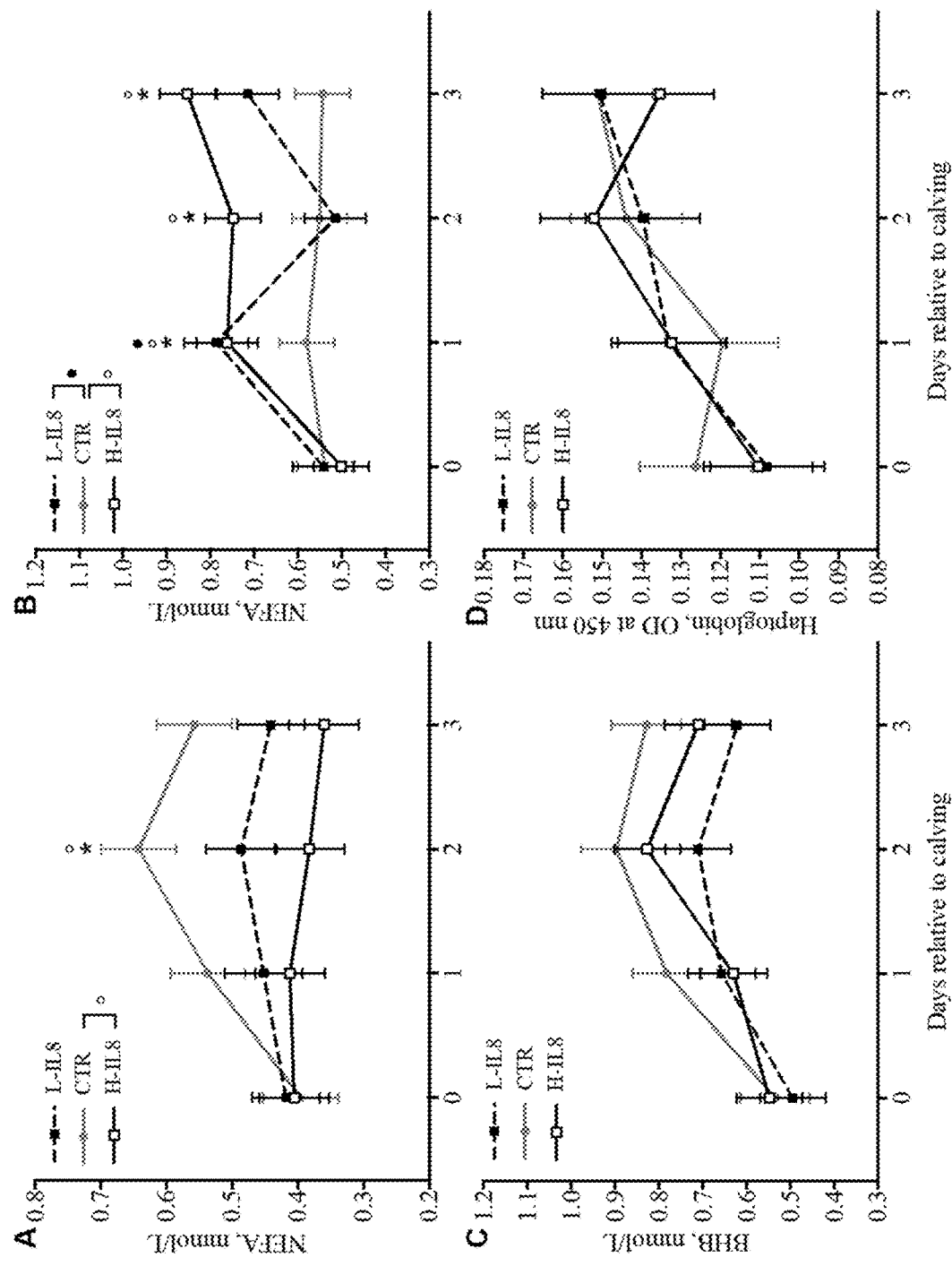

FIG. 6. Non-esterified fatty acids (NEFA) serum levels of primiparous (A) and multiparous (B) cows, and β-hydroxybutyrate (BHB; C), and haptoglobin (D) serum levels of cows treated with rbIL-8 and controls from study 1. Postpartum cows (n=213) were randomly allocated into one of three intrauterine treatment groups: control (CTR; 250 mL of saline solution), low-dose (L-IL8; 11.25 μg of rbIL-8 diluted in 250 mL of saline solution), and high-dose (H-IL8, 1,125 μg of rbIL-8 diluted in 250 mL of saline solution). Blood samples were harvested from a subset of cows (20/treatment group). Results are presented at LSM±SEM. *P≤0.05.

Figure 7:
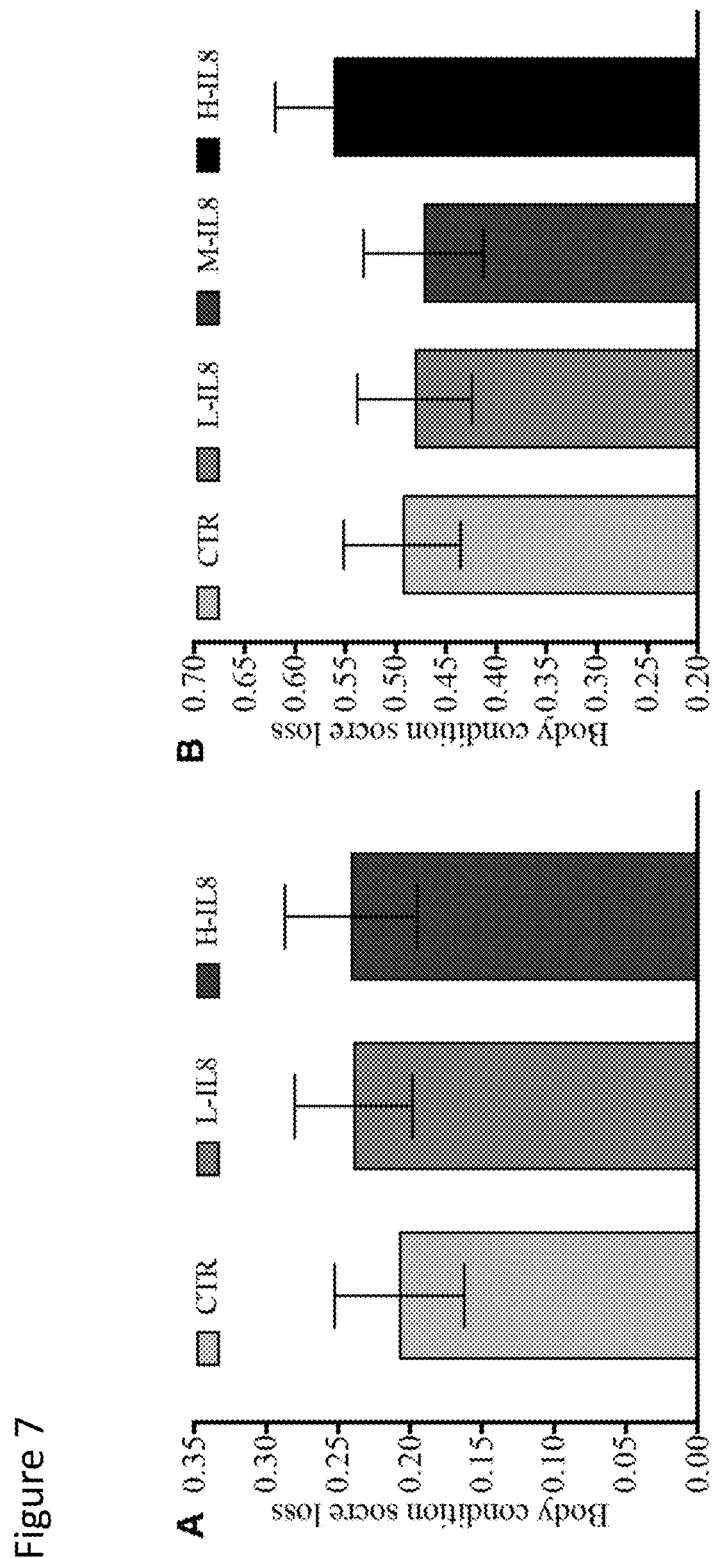

FIG. 7. Body condition score loss from day of enrollment (day of parturition) until 35 days in milk of cows treated with different doses of rIL8 and controls from studies 1 (A) and 2 (B). For study 1, 213 cows were randomly allocated into one of three intrauterine treatment groups: control (CTR; 250 mL of saline solution), low-dose (L-IL8; 11.25 μg of rbIL-8 diluted in 250 mL of saline solution), and high-dose (H-IL8, 1,125 μg of rbIL-8 diluted in 250 mL of saline solution). For study 2, 164 cows were randomly allocated into one of four treatment groups: control (CTR, 250 mL of saline solution), low-dose (L-IL8, 0.14 μg of rbIL-8), medium-dose (M-IL8, 14 μg of rbIL-8), and high-dose (H-IL8, 1,400 μg of rbIL-8). Results are presented at LSM±SEM.

Figure 8:
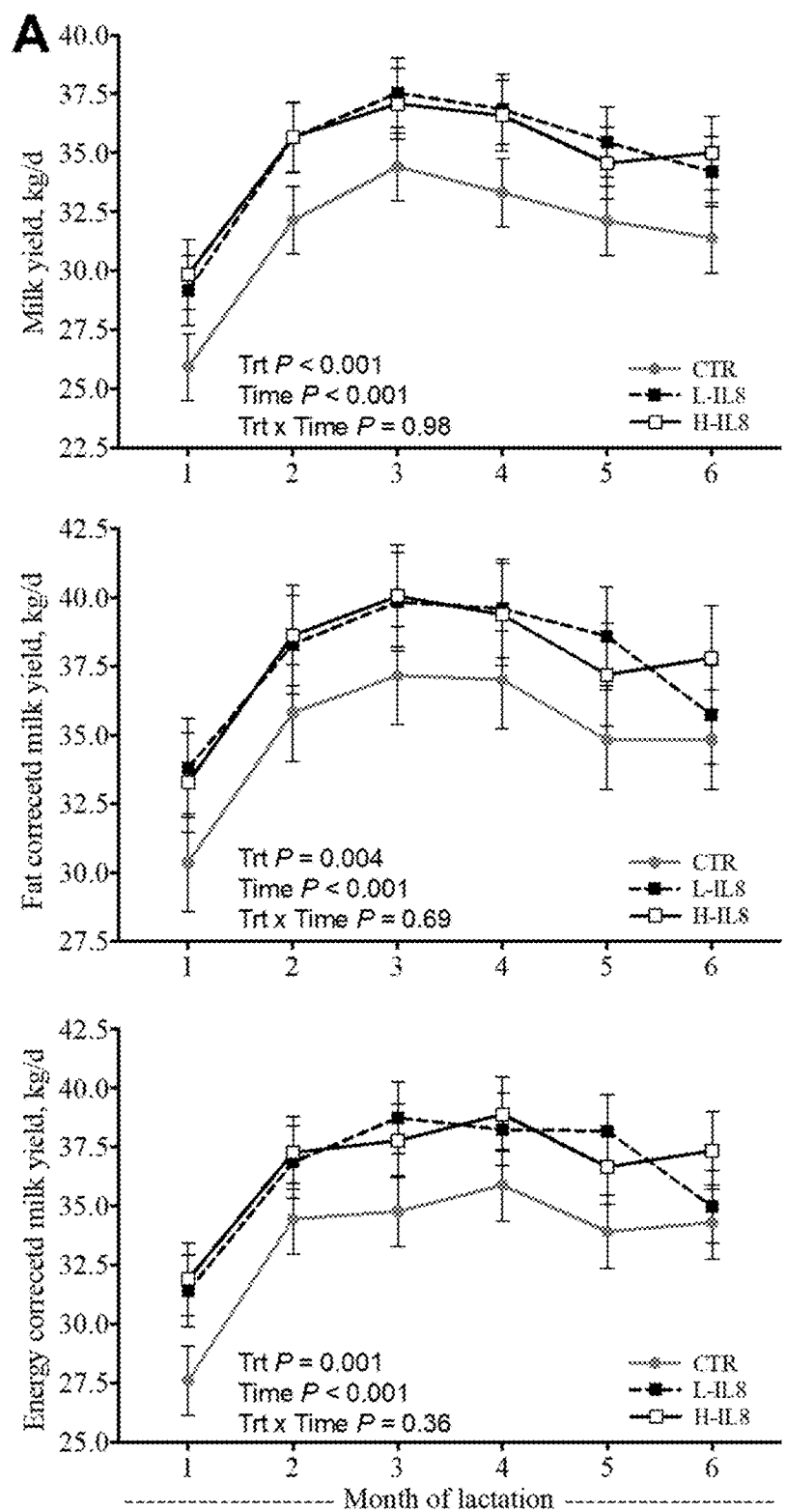
Figure 8:
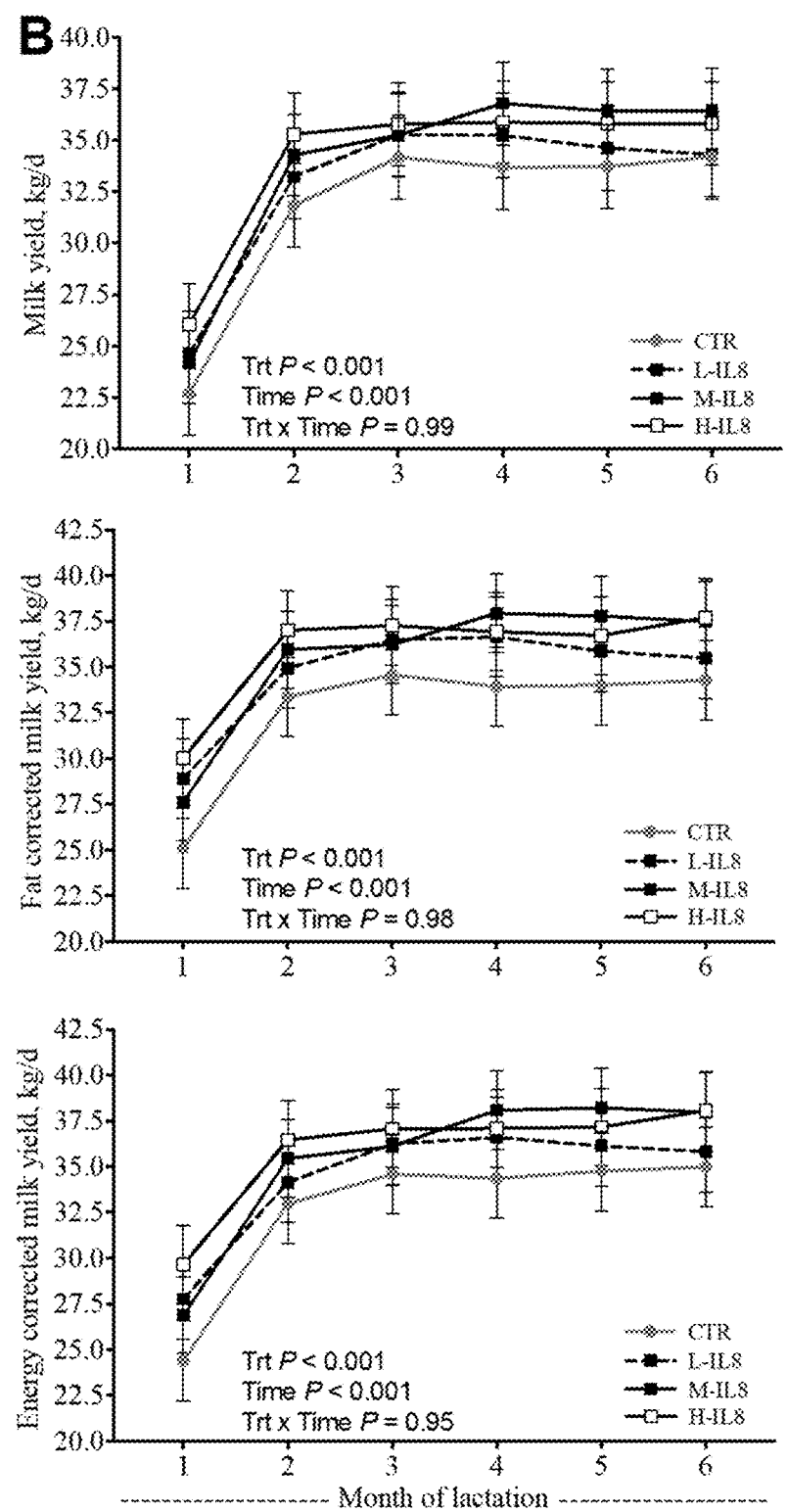

FIG. 8. Monthly milk yields (kg/d), 3.5% fat corrected milk yields (kg/d), and energy corrected milk yields (kg/d) after parturition of cows treated with different doses of rIL8 and controls from studies 1 (A) and 2 (B). For study 1, 213 cows were randomly allocated into one of three intrauterine treatment groups: control (CTR; 250 mL of saline solution), low-dose (L-IL8; 11.25 μg of rbIL-8 diluted in 250 mL of saline solution), and high-dose (H-IL8, 1,125 μg of rbIL-8 diluted in 250 mL of saline solution). For study 2, 164 cows were randomly allocated into one of four treatment groups: control (CTR, 250 mL of saline solution), low-dose (L-IL8, 0.14 μg of rbIL-8), medium-dose (M-IL8, 14 μg of rbIL-8), and high-dose (H-IL8, 1,400 μg of rbIL-8). P-value for the fixed effect of treatment, time and the interaction term treatment by time are included in each graph. Results are presented at LSM±SEM.

Figure 9:
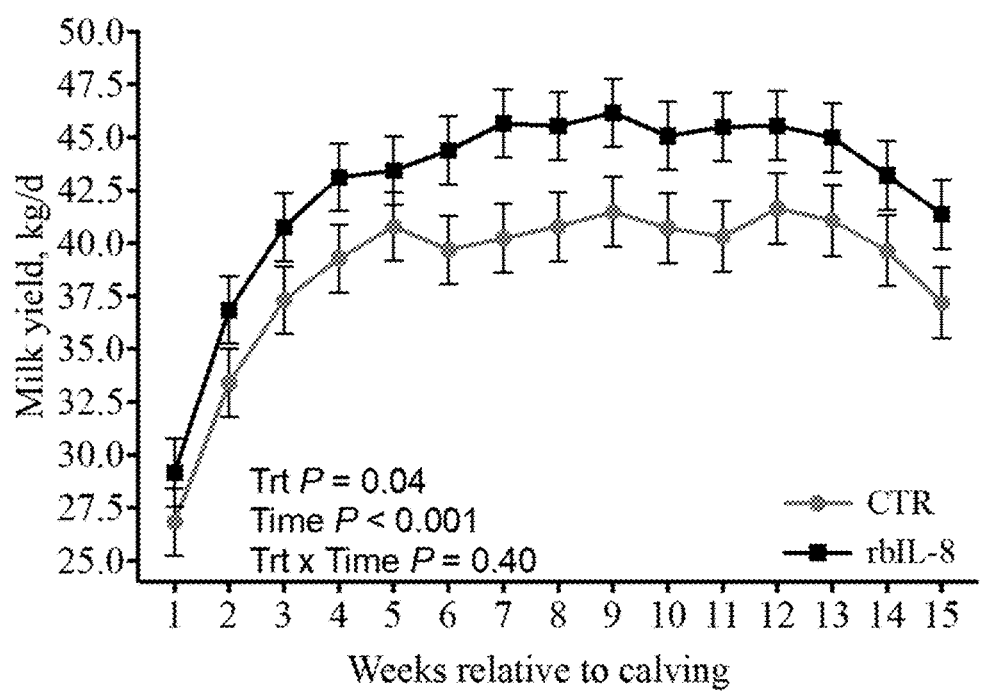

FIG. 9. Weekly milk yields (kg/d) after parturition of cows (n=39) treated with rbIL-8 (intravenous administration, rbIL-8=70 μg) and controls (saline solution) from study 3. P-value for the fixed effect of treatment, time and the interaction term treatment by time are included in the graph. Results are presented at LSM±SEM.

Part III Figures

Figure 10:
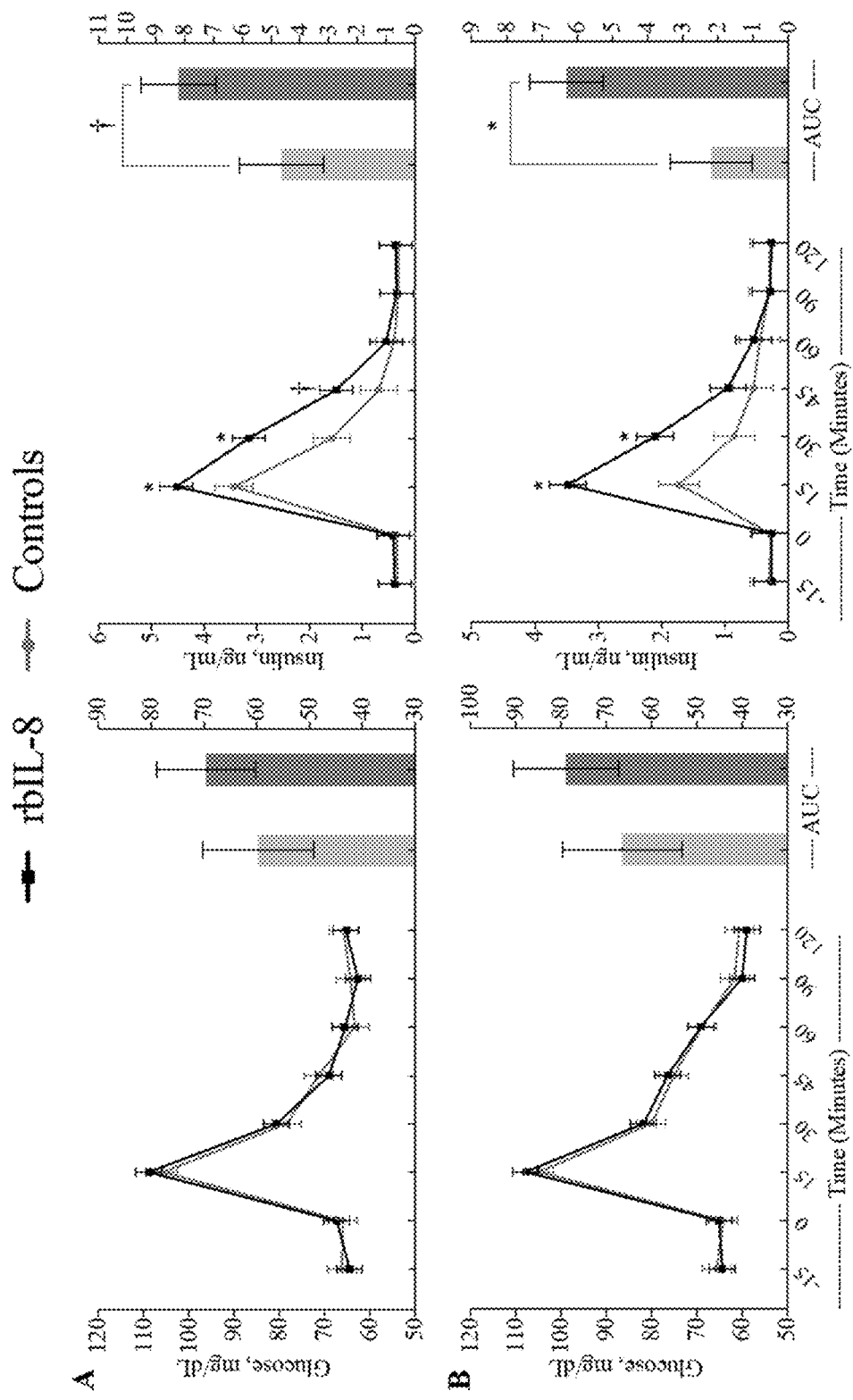

FIG. 10. Glucose and insulin responses to the glucose tolerance test in calves treated with rbIL-8 or controls at 12 h (A) and 7 d (B) after the treatments. Light gray bars and dark gray bars represent the area under the curve [AUC; mg/dL (glucose) and ng/mL (insulin) per 120 min] of control and rbIL-8-treated calves, respectively. *P≤0.001, P≤0.01, *P≤0.05, † P≤0.1.). Results are presented at LSM±SEM.

Figure 11:
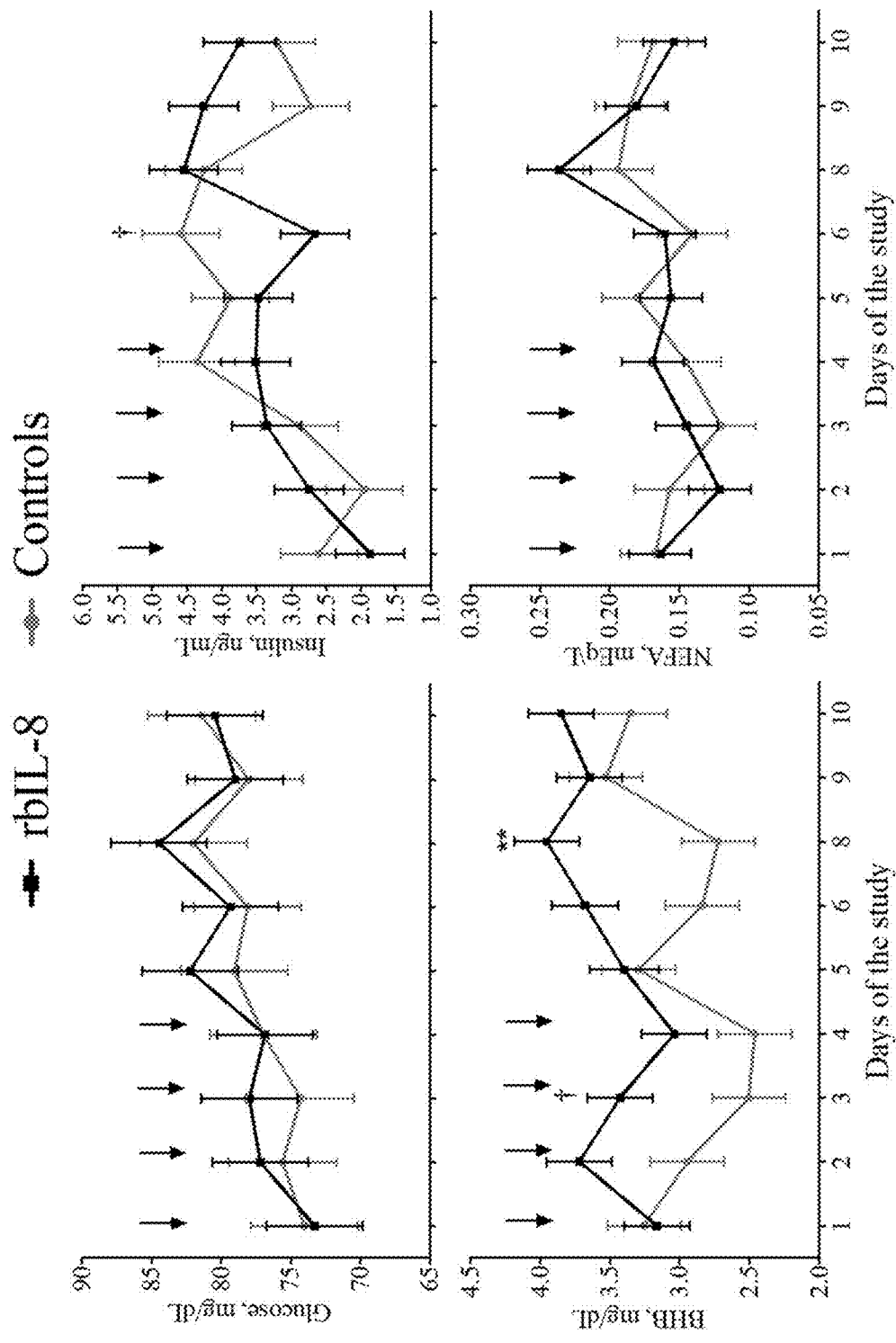

FIG. 11. Plasma concentrations of glucose, insulin, BHB and NEFA from d 1 to d 10 of the study of rbIL-8-treated and control calves. The arrows indicate the times of the treatments. *P≤0.001, P≤0.01, *P≤0.05, † P≤0.1.). Results are presented at LSM±SEM.

Figure 12:
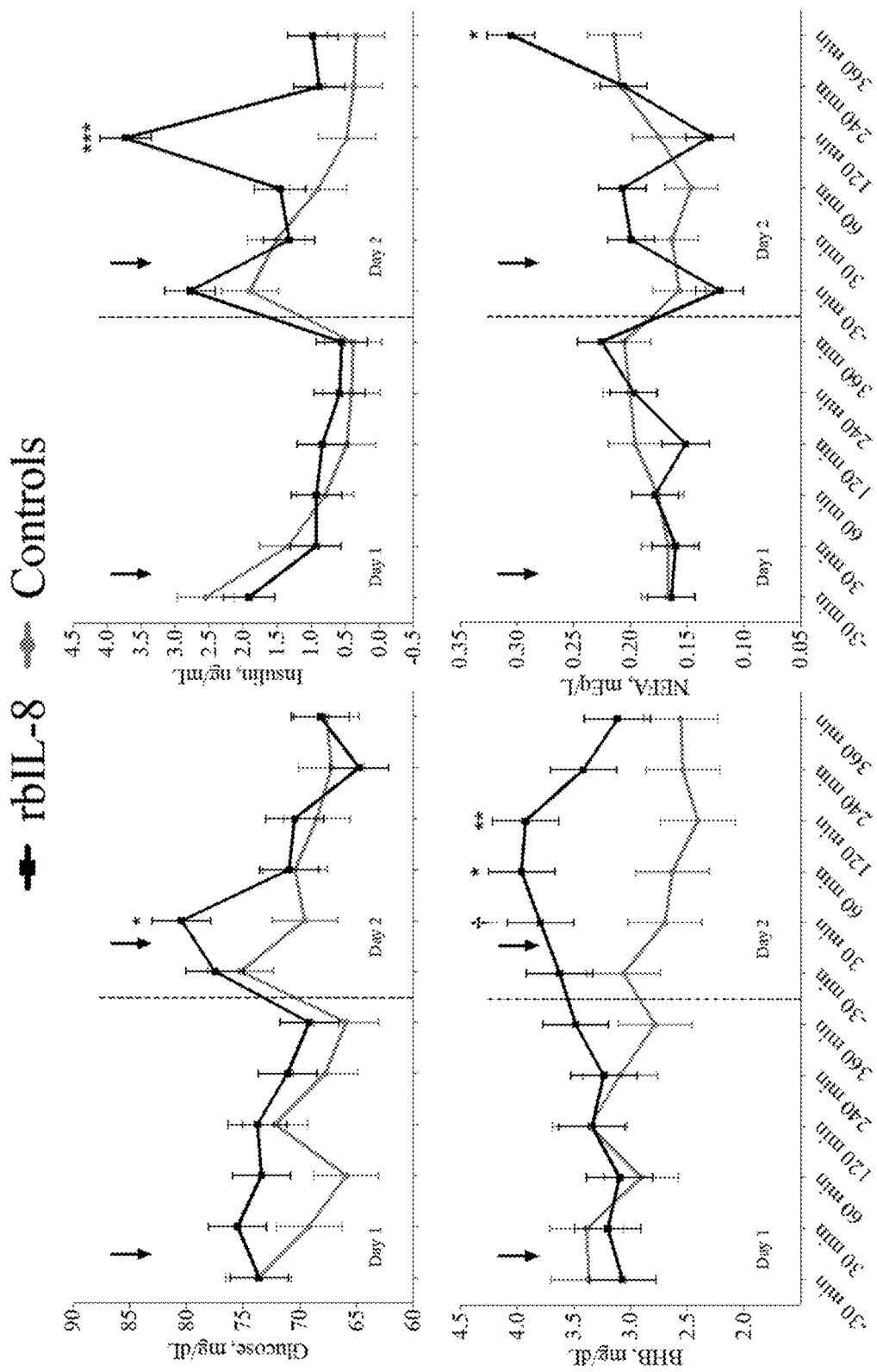

FIG. 12. Dynamics of the plasma concentrations of glucose, insulin, BHB, and NEFA after the first treatment (0900 h) on d 1 and 2 of the study of rbIL-8-treated and control calves. The arrows indicate the time of the treatments. *P≤0.001, P≤0.01, *P≤0.05, † P≤0.1. Results are presented at LSM±SEM.

Figure 13:
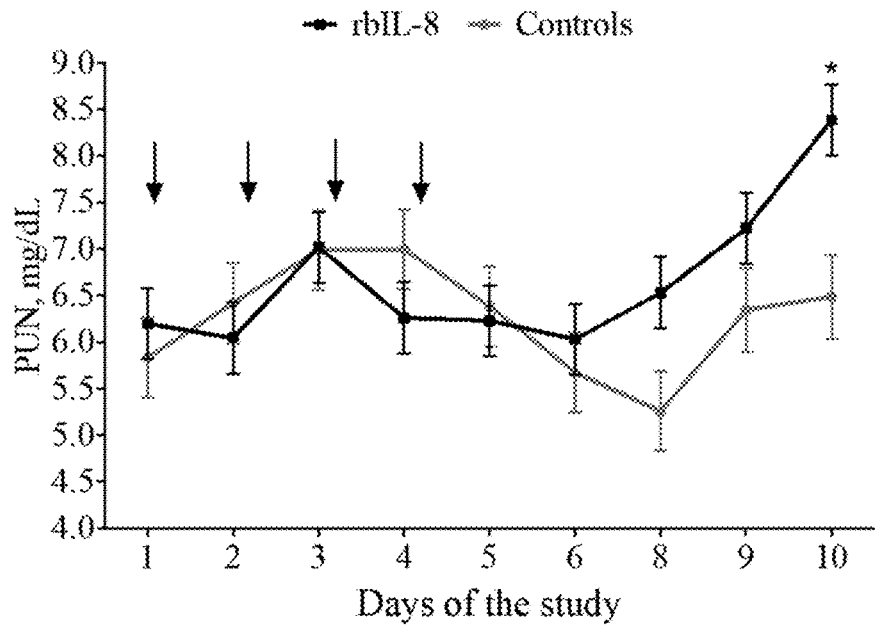

FIG. 13. Plasma urea nitrogen (PUN) concentration of rbIL-8-treated and control calves from d 1 to d 10 of the study. The arrows indicate the times of the treatments. * P≤0.001, P≤0.01, *P≤0.05, † P≤0.1. Results are presented at LSM±SEM.

Figure 14:
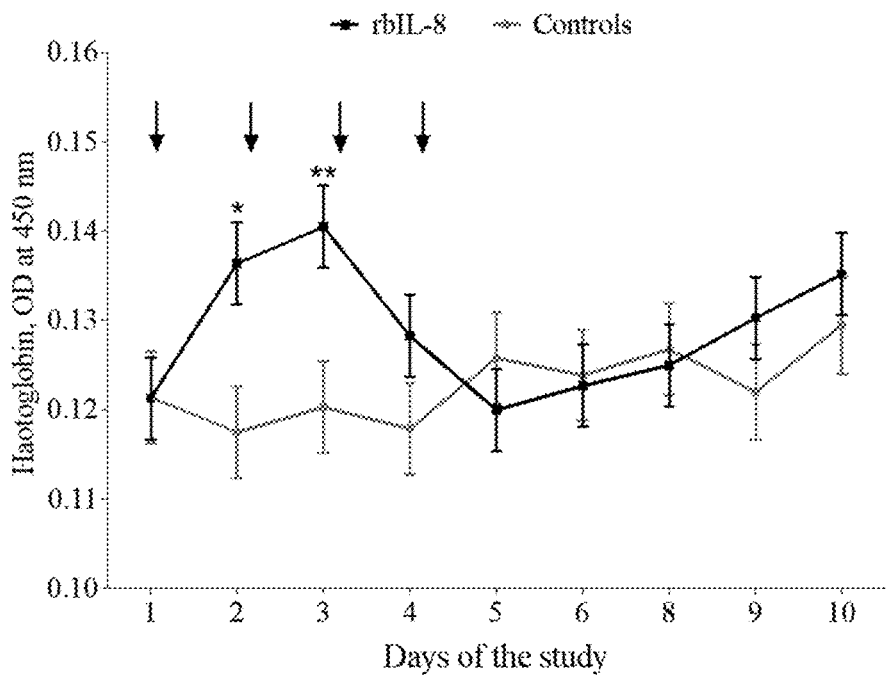

FIG. 14. Plasma concentration of haptoglobin (optical density units) of rbIL-8-treated and control calves from d 1 to d 10 of the study. The arrows indicate the times of the treatments. *P≤0.001, P≤0.01, *P≤0.05, † P≤0.1. Results are presented at LSM±SEM. OD=optical density.

Figure 15:
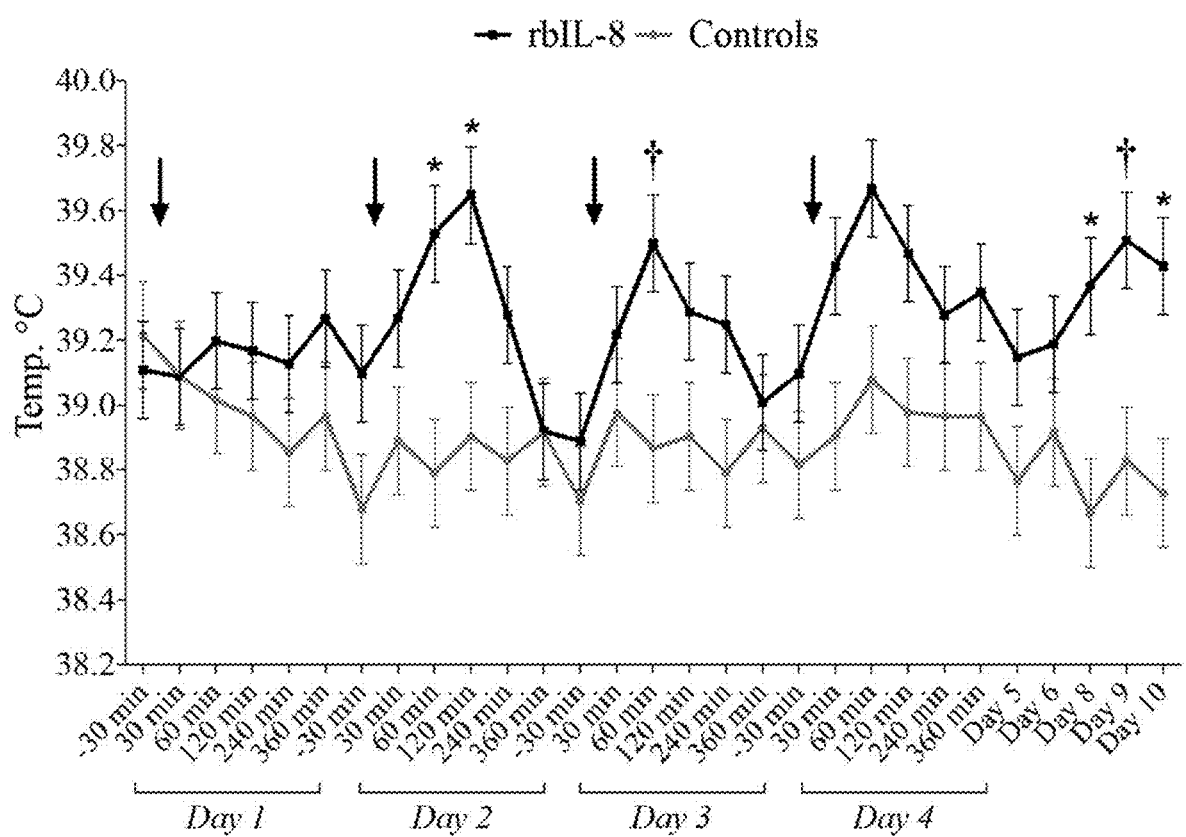

FIG. 15. Dynamics of rectal temperature following the first treatment (0900 h) on d 1, 2, 3, and 4 of the study of rbIL-8-treated and control calves. The arrows indicate the times of the treatments. *P≤0.001, P≤0.01, *P≤0.05, † P≤0.1. Results are presented at LSM±SEM.

Figure 16:
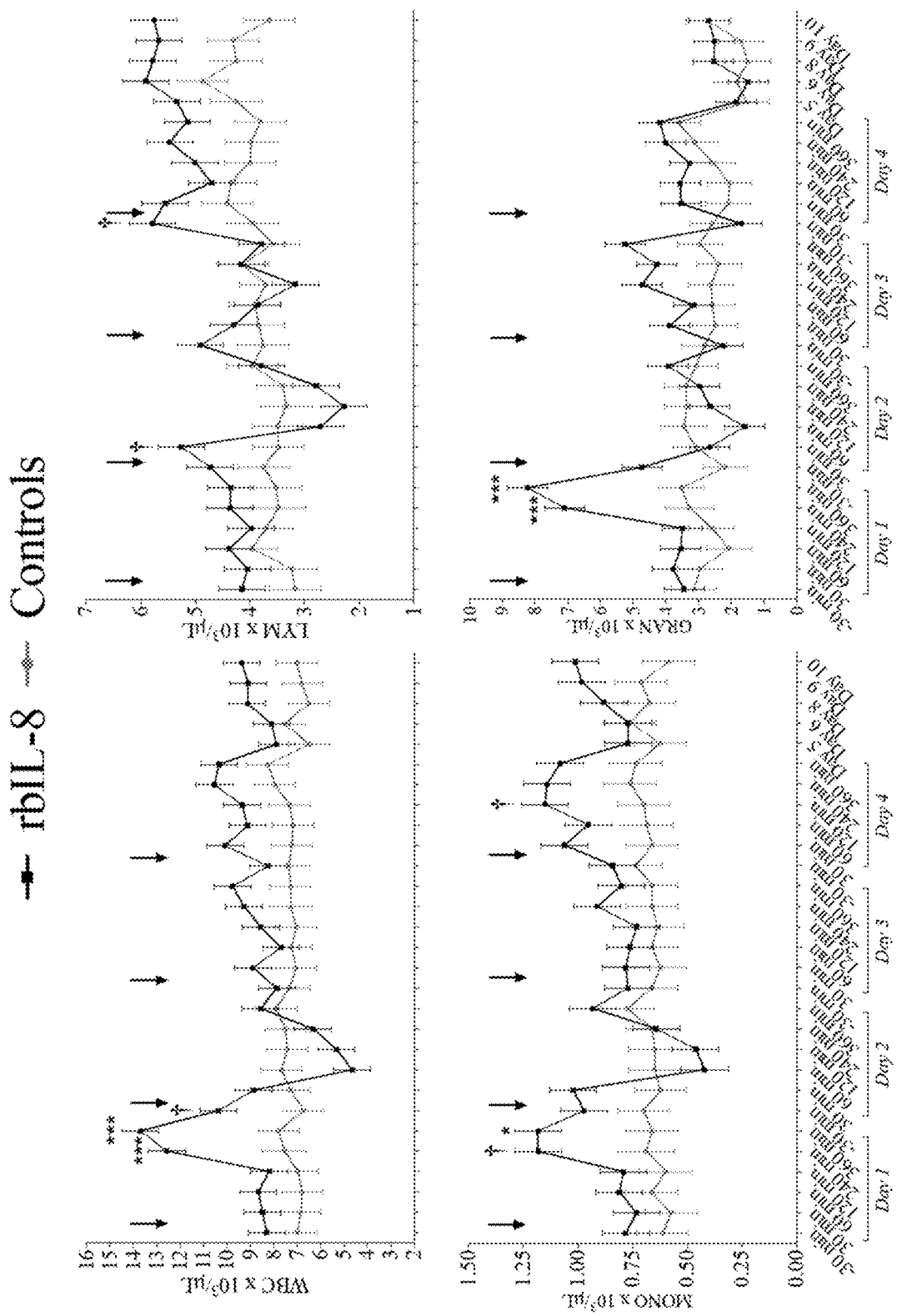

FIG. 16. Dynamics of the concentration in absolute numbers of white blood cells (WBC), lymphocytes (LYM), monocytes (MONO), and granulocytes (GRAN) following the first treatment (0900 h) on d 1, 2, 3 and 4 of the study of rbIL-8-treated and control calves. The arrows indicate the times of the treatments. *P≤0.001, P≤0.01, *P≤0.05, † P≤0.1. Results are presented at LSM±SEM.

Figure 17:
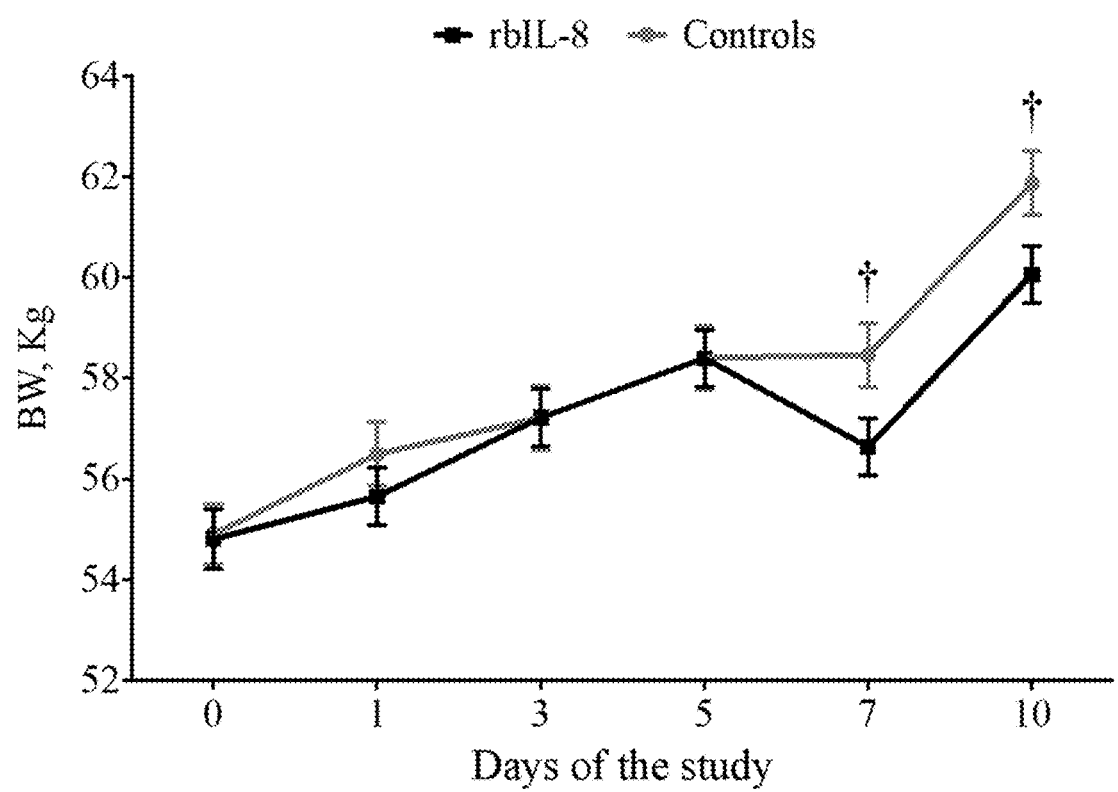

FIG. 17. The body weight of rbIL-8-treated and control calves from d 0 to d 10 of the study. *P≤0.001, P≤0.01, *P≤0.05, † P≤0.1. Results are presented at LSM±SEM.

Part IV Figures

Figure 18:
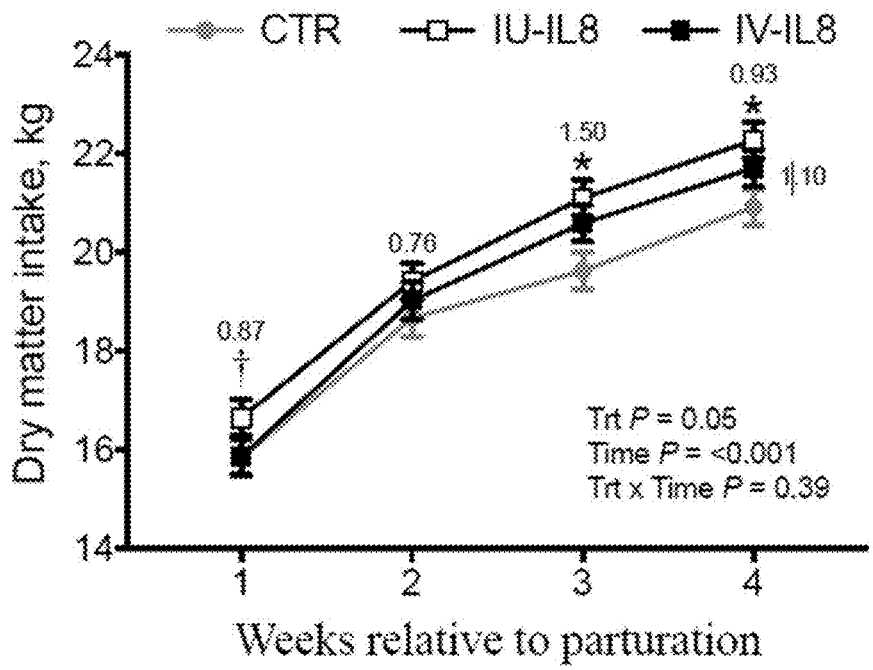

FIG. 18. Graph showing Dry Mater Intake data for intra-uterine IL8 (IU-IL-8), intravenous IL8 (IV-IL8), and control (CTR) animals.

Figure 19:
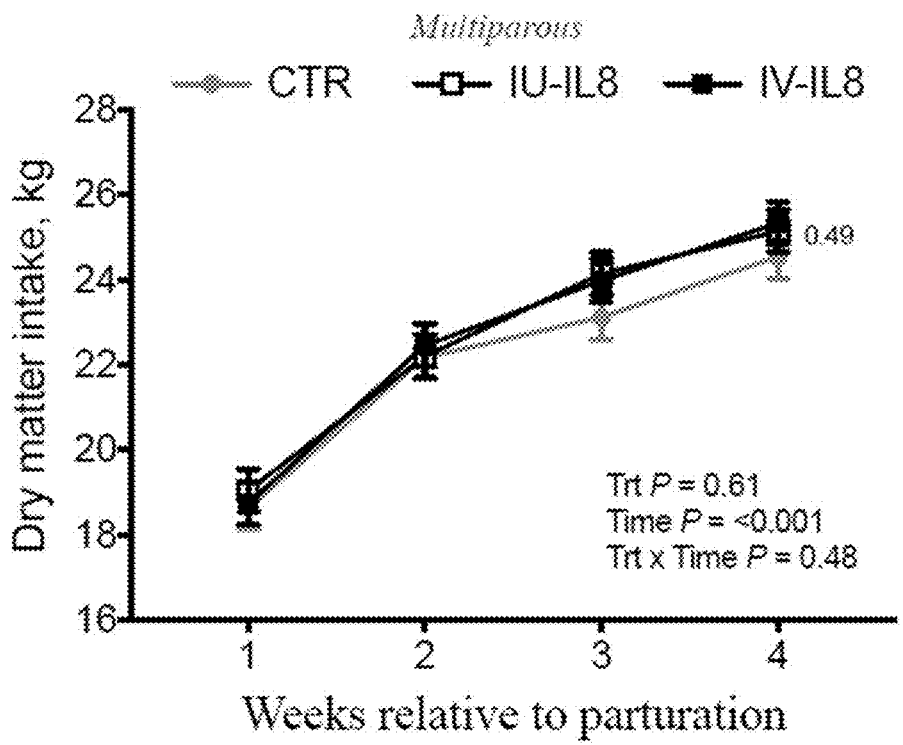

FIG. 19. Graph showing Dry Mater Intake data for IU-IL-8, IV-IL8, and CTR for multiparous animals.

Figure 20:
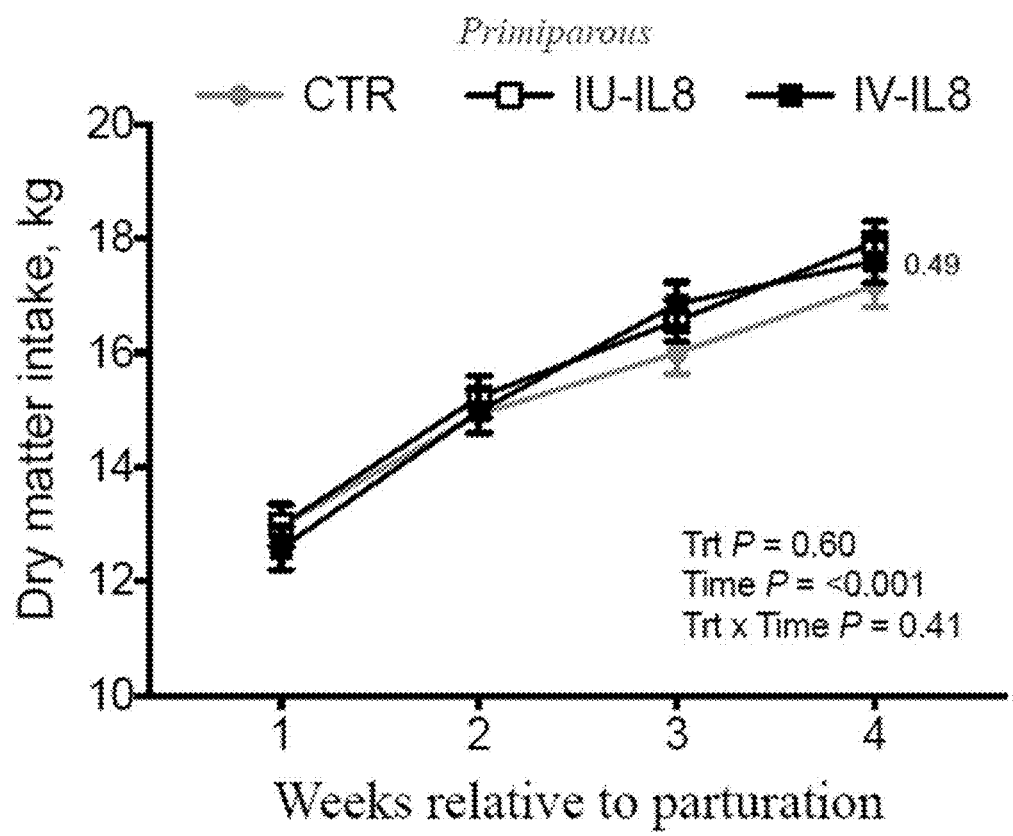

FIG. 20. Graph showing Dry Mater Intake for IU-IL-8, IV-IL8, and CTR for primiparous animals.

Figure 21:
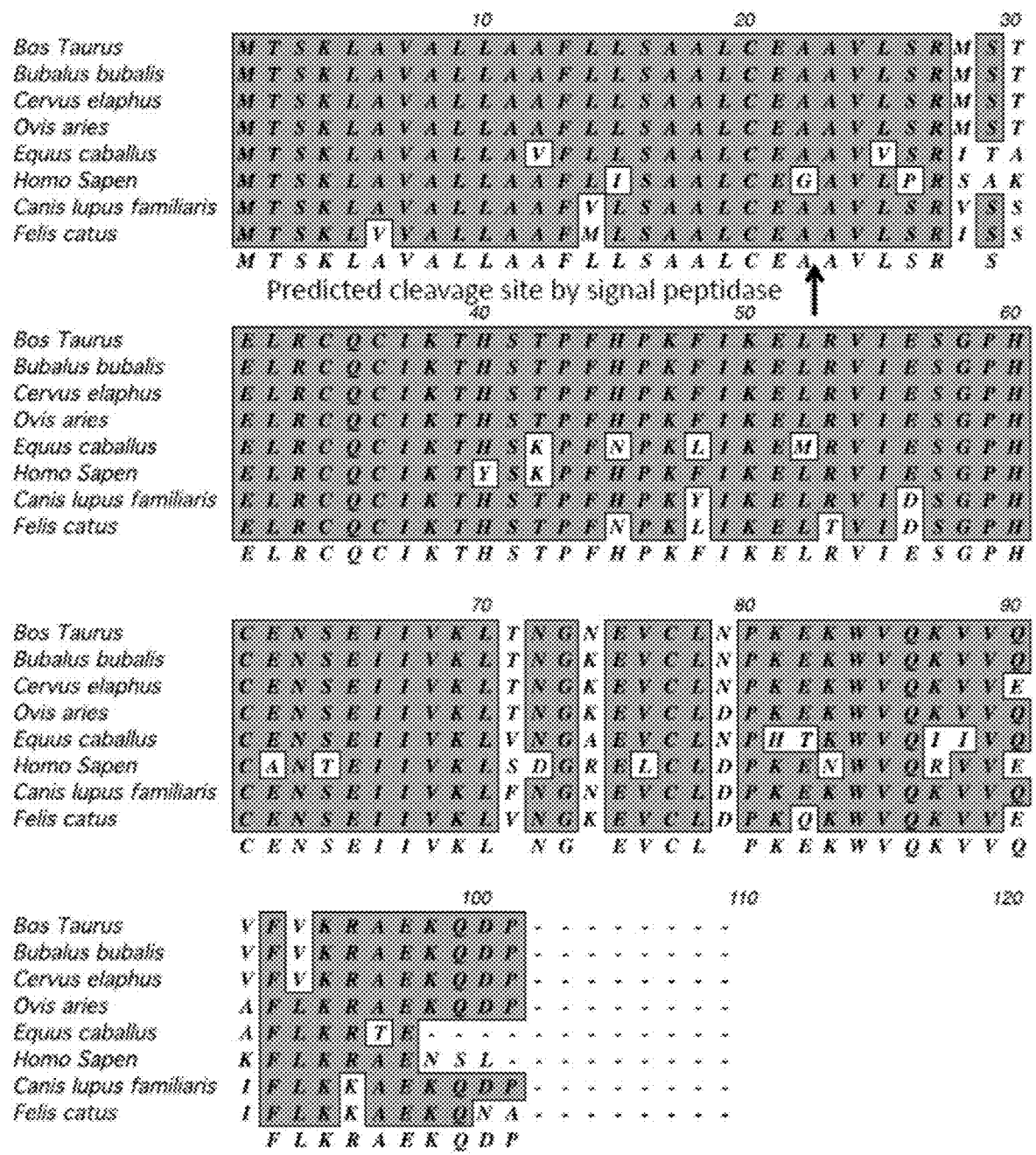

FIG. 21. Representative amino acid sequence alignments of IL-8 from select animal species. The sequences are shown from N- to C-termini. The sequence for each species and the consensus sequence is contiguous throughout the rows. The *Bos taurus* sequence is SEQ ID NO: 1. The Bubalus bubalis sequence is SEQ ID NO:2. The Cervus elephus sequence is SEQ ID NO:3. The Ovis aries sequence is SEQ ID NO:4. The Equus caballus is SEQ ID NO:5. The Homo sapiens sequence is SEQ ID NO:6. The Canis lupus familiaris sequence is SEQ ID NO:7. The Felus catus sequence is SEQ ID NO:8. The consensus of the specific mammal sequences shown in the bottom row is SEQ ID NO:9.

DETAILED DESCRIPTION

Unless defined otherwise, all technical and scientific terms used herein have the same meaning as commonly understood by one of ordinary skill in the art to which this invention belongs. Every numerical range given throughout this specification includes its upper and lower values, as well as every narrower numerical range that falls within it, as if such narrower numerical ranges were all expressly written herein.

This disclosure includes every nucleotide sequence described herein, and all sequences that are complementary to them, RNA equivalents of DNA sequences, all amino acid sequences described herein, and all polynucleotide sequences encoding the amino acid sequences. Each protein sequence and functional fragments of them are included. Polynucleotide and amino acid sequences having from 80-99% similarity, inclusive, and including ranges of numbers there between, with the sequences provided here are included in the invention. All of the amino acid sequences described herein can include amino acid substitutions, such as conservative substitutions, that do not adversely affect the function of the protein or polypeptide that comprises the amino acid sequences.

The present disclosure relates generally to administering an effective amount of IL-8 to female mammals to improve the health of the female mammals, which can comprise prophylaxis and/or therapy of one or more uterine diseases and/or hyperketonemia, and increasing milk production and/or fat content of milk, and combinations thereof. The disclosure thus encompasses in certain embodiments administering an effective amount of IL-8 to a mammal such that milk production by the mammal is increased, and/or the fat content of milk produced by the mammal is increased, and/or the mammal has reduced uterine disease and/or reduced hyperketonemia. In embodiments the milk produced by the mammal is increased and collected. In embodiments reduced uterine disease includes but is not necessarily limited to reduced endometritis and/or puerperal metritis, and/or reduced retained placenta.

With respect to uterine diseases, as is known in the art, metritis generally involves inflammation of the wall of the uterus, while endometritis generally involves inflammation of the endometrium. In this regard, the present discovery that exogenously administered IL-8 has beneficial effects on uterine health was unforeseen because, among the known functions of IL-8 is its association with inflammation. Further, the serendipitous discovery of the favorable effects of IL-8 on milk fat content and milk production as further described below was unexpected. In view of these findings, the methods of the present disclosure result in an increase in the health of a female mammal as evidenced by, for example, increasing milk production, increasing fat corrected milk production, increasing energy corrected milk production, reducing the incidence of retained placenta, reducing the incidence or severity of metritis, or clinical endometritis, or puerperal metritis, or by improving the body condition score of the mammal at parturition, or reducing ketosis, including but not necessarily limited to reducing hyperketonemia, or reducing rectal temperature, or combinations thereof. Thus, the disclosure includes a variety of ways by which the general health and reproductive function of female mammals can be improved.

Those skilled in the art will recognize that energy corrected milk (ECM) is the amount of energy in milk based upon milk, fat and protein and adjusted to 3.5% fat and 3.2% protein. The conventional ECM formula is ECM=(0.327× milk lbs.)+(12.95×fat lbs.)+(7.65×protein lbs.).

It is expected that methods of the present disclosure will be applicable to any female mammal. In embodiments, the disclosure is directed to veterinary approaches, and thus in this aspect pertains to non-human mammals. In embodiments, the non-human female mammal to which IL-8 is administered is a ruminant, including but not necessarily limited to bovines, sheep, antelopes, deer, giraffes, and their relatives, and further can include pseudoruminants, such as the camelids. In embodiments, the ruminant is a female bovine mammal that is a member of the genus Bos, such as oxen, cows, and buffalo. In one embodiment the ruminant is a dairy cow. In embodiments the dairy cow is a primiparous or multiparous cow. In embodiments, the female mammal is an ungulate.

In an embodiment the disclosure includes administering IL-8 to a member of the genus Sus, and therefore encompasses practicing the invention with any swine, examples of which are not limited to the domestic pig (i.e., Sus domesticus), also commonly referred to as a swine or a hog.

The disclosure also includes administering IL-8 to non-bovine and non-ruminant mammals, including but not necessarily limited to equines, canines, and felines. In embodiments the disclosure includes administering IL-8 to aquatic mammals, such as cetacean mammals, examples of which are not necessarily limited to whales, dolphins and porpoises. Thus, the invention in certain aspects pertains to companion animals, as well as animals kept in conservation settings, for example in zoos or aquariums.

The methods described herein are also expected to be suitable for use with humans, such as by administering IL-8 to a human female for the purpose of increasing milk production or increasing the nutritional value of milk by increasing its fat content.

Particular implementations of this disclosure may also exclude IL-8 administration under certain circumstances. For example, in certain approaches, IL-8 administration is not given to a mammal from which milk is not obtained subsequent to the IL-8 administration. In certain embodiments, milk obtained subsequent to IL-8 administration to, for example, a dairy cow, is suitable for human consumption. Thus, in certain embodiments the IL-8 administration is to a non-human mammal from which milk is intended to be obtained and/or is obtained, wherein the milk is for human consumption and/or is consumed by humans. In certain aspects the disclosure may exclude IL-8 administration to particular types of mammals. In one example, the IL-8 is not given to a rodent. The disclosure can thus comprise administering IL-8 to all types of mammals, except rodents, specific examples of which include but are not limited to mice, rats and guinea pigs. In another example primates, including either or both human and non-human primates, can be excluded from the group of mammals to which the IL-8 is given. In one example the mammal to which IL-8 is administered does not have thrombosis, including but not limited to deep vein thrombosis. In certain embodiments the disclosure may exclude IL-8 administration during certain time periods, for example, in certain embodiments the disclosure may exclude IL-8 administration during pregnancy for the purpose promoting fertilization, implantation, or to induce uterine contractions. In certain aspects, IL-8 is not administered to a species of mammal for which acute inflammation after coitus is beneficial to and/or promotes conception. In certain embodiments the IL-8 is not administered by direct infusion into mammary tissue or a teat, and thus in embodiments the IL-8 administration does not induce or promote mastitis.

IL-8 is well known in the art as a chemokine produced by a number of different cell types, including macrophages. It is also referred to as CXCL8, and binds with specificity to the CXCR1 and CXCR2 receptors. It is produced as a precursor protein which is typically between 99 amino acids (for human IL-8), and up to 103 amino acids for other species, and undergoes cleavage to produce active isoforms. The cleaved version of human IL-8 that is most frequently secreted by human macrophages is 72 amino acids in length. In connection with this, while certain representative examples of the effects of recombinant bovine IL-8 (also referred to herein as "rbIL-8") administration to dairy cows are provided in this disclosure, it is expected that any IL-8 expressed by any animal can be used in the methods of the invention. In non-limiting embodiments, the IL-8 is a recombinantly produced *Bos taurus* IL-8 which comprises the following sequence or a fragment of:
MTSKLAVALL AAFLLSAALC EAAVLSRMST ELRCQCIKTH STPFHPKFIK ELRVIESGPH CENSEIIVKL TNGNEVCLNP KEKWVQKVVQ VFVKRAEKQD P (SEQ ID NO: 10). This sequence comprises the natural bovine IL-8 leader sequence.

In embodiments, the IL-8 is the processed form, and thus is shorter than a precursor IL-8 sequence. In embodiments, the IL-8 is at least 70 amino acids in length. In embodiments, the IL-8 used in the methods of this disclosure have at least 70 contiguous IL-8 amino acids, wherein the at least 70 amino acids have at least 70.0% homology to the bovine sequence presented above, and/or to the consensus sequence presented in the FIG. 21 (bottom row of alignment). In embodiments, the IL-8 comprises or consists of a sequence having that is between 70-100% identical to the *Bos Taurus* sequence across 70, 71, 72, 73, 74, 75, 76, 77, 78, 79, or 80, or more, contiguous amino acids thereof. In embodiments, such sequence identity and length is relative to the amino acid sequence beginning at the N-terminus, or beginning at any amino acid from the N-terminus through amino acid position 2-25, inclusive, and including each amino acid position there between. In embodiments, the IL-8 comprises or consists of the sequence or a fragment of any amino acid sequence presented in the FIG. 21. In an embodiment, the IL-8 comprises a change of the ELR to AAR in the *Bos Taura* sequence shown in the FIG. 21.

IL-8 used in methods of this disclosure can be obtained from any suitable source. In one embodiment, the IL-8 is obtained commercially from a vendor. For example, human IL-8 expressed in *E. coli* and provided as a lyophilized powder can be obtained from Sigma Aldrich. Bovine IL-8 can be obtained from Kingfisher Biotech, Inc., of Saint Paul, Minn. Alternatively, the IL-8 can be produced recombinantly using techniques well known to those skilled in the art, such as by using a protein expression system.

In a non-limiting and illustrative embodiment, IL-8 is produced recombinantly using the approaches shown in any of Part I, Part II, or Part II of this disclosure, or modifications thereof that will be apparent to those skilled in the art given the benefit of the present disclosure. In embodiments, a pET28-His-L-EK-IL8 construct as described in WO/2016/111992, from which the entire disclosure is incorporated herein, is provided. In embodiments, a full length IL-8 comprises a leader sequence on the N-terminal end of IL-8, such as a leader sequence that remains are part of the expressed protein by way of cloning using pET28 and pTrc plasmids. In embodiments, the IL-8 contains a poly-histidine purification tag, such as a 6×His-tag that is used for purification of the IL-8. In embodiments, the IL-8 contains the natural IL-8 leader sequence, or any combination of the foregoing. Any segment of the plasmid-derived amino acid sequence, and any segment of the IL-8 sequence, can be excluded from the invention.

Compositions comprising IL-8 for use in the methods of this disclosure can be provided in a variety of forms and delivered via a variety of routes. Compositions for use in humans or non-human mammals can be prepared by mixing IL-8 with any suitable pharmaceutically acceptable carriers, excipients and/or stabilizers. Some examples of compositions suitable for mixing with IL-8 can be found in: Remington: The Science and Practice of Pharmacy (2005) 21st Edition, Philadelphia, Pa. Lippincott Williams & Wilkins. In certain aspects, IL-8 can be added to the feed of a mammal, and thus consumed as a dietary additive to support reproductive health and/or milk production.

Compositions comprising IL-8 can be administered to the mammal using any available method and route, including oral, parenteral, subcutaneous, intraperitoneal, intrapulmonary, and intranasal administrations. Parenteral infusions include intramuscular, intravenous, intra-arterial, intraperitoneal, intravaginal, intrauterine, and subcutaneous administration. Thus, the compositions can be administered systemically. The composition can be administered via an intra-mucosal approach. The administration of IL-8 can be performed before or after birth, and can be performed during pregnancy.

In certain embodiments, subject to certain provisos as further described herein, compositions comprising IL-8 are administered to a pregnant mammal, and thus a prepartum administration is used. In certain approaches the prepartum administration is performed during the mammogenesis period which varies from species to species but is within the last third of the gestation. As a non-limiting illustration, in an embodiment, the gestation period of a Holstein cow is 280 days. Thus, the administration of IL-8 after approximately 180 days of gestation is believed, without intending to be bound by theory, to help the development of the mammary gland leading to an increase in milk production in the postpartum period.

In an embodiment, a prepartum administration comprises an intravaginal administration of an IL-8 containing composition. In one non-limiting example, an intravaginal administration of an IL-8 containing composition is administered to a pregnant mammal, such as a dairy cow.

In certain embodiments, compositions comprising IL-8 are administered to a mammal that has recently given birth, and thus a postpartum administration is used. In embodiments, a postpartum intrauterine administration is used. In one non-limiting example, a postpartum intrauterine administration of an IL-8 containing composition is administered to a mammal, such as a dairy cow, within 72 hours of giving birth (parturition). Administering within shorter or longer times after parturition is also encompassed by this disclosure. In certain non-limiting examples, the composition comprising IL-8 is administered immediately post partition, and up to 20 weeks after parturition. In certain approaches the disclosure thus includes administering on the same day as parturition, or within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140 days, inclusive, and including all ranges of integers there between, from parturition.

In certain approaches, the disclosure comprises, as an alternative to exogenous IL-8 administration, stimulating endogenous IL-8 production such that one or more of the effects described herein are produced. In non-limiting examples, stimulating exogenous IL-8 production comprises administering to a mammal one or more IL-8 stimulating compounds and/or compositions, including but not necessarily limited to tumor necrosis factor alpha (TNF-α), lipopolysaccharide (LPS), an interleukin-1 (IL-1), platelet-activating factor (PAF), and/or other substances that will can be used in embodiments of the instant invention, given the benefit of the present disclosure.

In certain embodiments the present disclosure comprises administration of an IL-8 containing composition to one or more mammals, a non-limiting example of which is a dairy cow(s), such that any one or any combination of the following is achieved: i) an increase in milk production; ii) an increase in energy corrected milk production; iii) an increase in fat content of milk produced by the mammal; iv) a reduction in the development of puerperal metritis, and/or a reduction in the incidence of puerperal metritis when the IL-8 administration is given to a plurality of mammals; v) a reduction in development of clinical endometritis, and/or a reduction in the incidence of clinical endometritis when the IL-8 administration is given to a plurality of mammals; vi) a reduction in hyperketonemia, such as a reduction in subclinical ketosis, and/or the incidence of subclinical ketosis when the IL-8 administration is given to a plurality of mammals, and vii) inhibiting retained placenta, viii) an increase in dry matter uptake. In embodiments, the foregoing effects of IL-8 administration are achieved by using an intrauterine or systemic (i.e., intravenous) administration of the IL-8 containing composition, but it is considered that other administration routes could also be used.

It will be recognized that any of the foregoing results produced as a result of IL-8 administration can be compared to a reference to assess the effect of the IL-8 administration. Any suitable reference can be used, and those skilled in the art will recognize suitable references given the benefit of this disclosure. In embodiments, the reference can be a single value or a range of values. For example, a reference can be a standardized curve or an area on a graph. The reference can comprise a positive or negative control. In embodiments the reference comprises a measurement made from a sample obtained from a mammal to which IL-8 was not administered, or a different amount of IL-8 was administered, or a different IL-8 dosing schedule was used. In various aspects a measurement of a result can be compared to a reference to provide a qualitative or quantitative determination of the result, which may be positively or negatively correlated with IL-8 administration. In certain embodiments, comparison to a reference can be performed by an individual skilled in animal handling or testing. For example, retained placenta and metritis can be diagnosed by trained farm personnel according to specific protocols known in the art, and certain measurements as compared to a non-retained placenta or non-metritis condition can be made by those individuals, whether or not a direct comparison to a suitable reference is made. For example, in certain embodiments, a change in uterine discharge, such as the appearance of fetid, watery, red brown uterine discharge accompanied with fever can be used to diagnose puerperal metritis, whereas post-parturition cows which do not produce uterine discharge with such characteristics are determined to not have puerperal metritis.

This disclosure includes administering IL-8 to any one, or more than one mammal, such as a plurality or population of mammals. In an embodiment, the plurality of mammals comprises a group of dairy cows which can be present in, for example, a dairy farm of any scale, ranging from a few dairy cows to a commercial dairy farm which may house thousands of dairy cows.

As will be recognized from the results presented in the Examples and Figures of this disclosure, representative but non-limiting experiments demonstrate the foregoing enumerated effects using intrauterine and intravaginal infusions comprising a range if IL-8 amounts. In particular and non-limiting examples, aspects of the disclosure are demonstrated using 9.5 mg, 1.125 mg, 0.095 mg, 0.0095 mg, and 11.25 μg of recombinant IL-8. Thus, in embodiments, from 11.25 μg-9.5 mg, including all numbers to the second decimal point in the g range for the upper and lower values, and all ranges of these numbers, are included in this disclosure.

Thus, the disclosure demonstrates that a wide range of IL-8 amounts can elicit some or all of these effects, and given the benefit of this disclosure those skilled in the art will recognize how to modify IL-8 dosing to obtain a desired result in any particular mammal. Further, the disclosure includes a demonstration that IL-8 doses ranging from 9.5 mg, to as little as 0.0095 mg, produce a statistically significant increase in milk fat percentage. Accordingly, the disclosure includes administering an effective amount of IL-8, wherein the effective amount of IL-8 is an amount that results in a desired outcome. In one embodiment, the amount of IL-8 is from 0.001 μg to 10 mg, including all integers and amounts there between to the 0.001 μg unit, and all ranges of μg and mgs there between. In embodiments, at least 11.25 μg of IL-8 is administered to the mammal. In connection with this, the form and character of the particular IL-8 dosing regimen will be dictated by the route of administration and other known variables, taking into account such factors as the size, health, age, type of mammalian species, numbers of previous births (if any), previous history of uterine or other related conditions, and risk factors related to uterine conditions and milk production. In an embodiment, the mammal is in need of an IL-8 administration because of, for example, having a risk for or otherwise being predisposed to a uterine condition, or because of poor milk production. In embodiments, the administration of IL-8 is prophylactic or therapeutic, or both.

IL-8 compositions of this disclosure can be administered only once, or in a series of dosages, and can be administered concurrently or sequentially with any other compound or composition intended to improve the general health of the mammal, or for the specific purpose of promoting or enhancing the IL-8-induced effects described herein. In embodiments, the IL-8 administration is used in conjunction with an antibiotic, a hormone, or a growth factor. In certain approaches, IL-8 is administered only a single time, yet produces a durable effect on any one or combination of health and/or milk production outcomes as described herein.

Desired milk fat content can be determined using any suitable method, several of which are known in the art. For example, milk fat content can be determined by the so-called Babcock test or Gerber Method. In embodiments, the fat content of milk is increased. The present disclosure provides a demonstration of an increase in milk fat in milk obtained from dairy cows subsequent to intrauterine and intravaginal infusions of recombinant IL-8. Thus, in certain approaches, the disclosure includes methods for stimulating production of milk with increased fat, and includes the milk produced by such methods.

In certain aspects, the disclosure includes elevating milk fat in milk produced by a dairy cow relative to a control, such as an amount of milk fat in milk produced by a dairy cow that did not receive an IL-8 administration. In certain approaches, the increased milk fat comprises an increase of milk fat (relative to a control) of at least 0.01% to 0.5%, inclusive, and including all numbers to the second decimal point there between, and all ranges of such numbers. In certain approaches, milk produced according to an embodiment of this disclosure comprises at least 3.4% milk fat, and may comprise from 3.4%-4.4% milk fat, including all numbers to the second decimal point there between, and all ranges of such numbers. In certain approaches milk comprises such amounts of milk fat when first obtained from the mammal. Thus, the stated amounts may be present in unprocessed milk.

Practicing methods of this disclosure has in certain embodiments one or more effects on the mammal that is durable for a period of time. For example, the disclosure demonstrates increased the production of milk and fat corrected and energy corrected milk for 11 months from a single IL-8 administration. In certain implementations, the administration of IL-8 results in increased milk production, or increased fat corrected and/or energy corrected milk production, and/or an increase in fat content of milk, for a period of at least 1, 2, 3, 4, 5, 6, 7, 8, 9, 10, or 11 months subsequent to the IL-8 administration. Longer time periods are also encompassed. In certain approaches, IL-8 administration produces a durable effect on milk production that extends throughout a single lactation period, i.e., the entire period of lactation immediately subsequent to or during which the IL-8 is administered. In one example, the lactation period ends with a subsequent pregnancy. The disclosure includes in one non-limiting approach administering IL-8 in a single dose such that one or more effects on milk content and/or production as described herein persist for a period of at least 1, 2, 3, 4, 5, 6, 7, 8, 9, 10, or 11 months, or an entire period of lactation subsequent to or during which the single IL-8 administration is performed. In certain embodiments, one or more effects of IL-8 begin within a period of 1, 2, 3, 4, 5, 6, or 7 days of IL-8 administration and can persist thereafter according to any of the time periods described herein.

In certain aspects, the disclosure comprises increasing the amount of milk produced by a mammal, such as a dairy cow. In certain aspects, the increase in milk production comprises an increase of at least 1, 2, 3, 4, 5, 6, 7, 8, 9, 10, 11, or 12 pounds of milk per day. The increase in milk production can be assessed relative to a control, such as a dairy cow to which IL-8 is not administered. Those skilled in the art will recognize that a value of any IL-8 induced change described herein can be taken as, for example, an average value determined from a group of mammals over a period of time.

In another embodiment, the disclosure includes obtaining milk, and includes the milk itself, from a mammal treated with IL-8 as described above. This aspect comprises administering IL-8 to a female mammal described herein, and collecting milk produced subsequent to the administration. In one embodiment the milk produced by this process differs from other types of milk in that it has an increased fat content, such as milk fat content as described above. In embodiments, containers containing milk obtained from a mammal treated with IL-8 are provided. The containers can be any container, such as a consumer oriented container, for example a milk carton, or larger containers, such as a vat, or containers suitable for shipping or otherwise transporting large quantities of milk. In embodiments products made using milk obtained from a process describe herein are provided. Non-limiting examples of such products include cheese, yogurt, milk-based creams and creamers, ice cream, dairy based toppings, and any other dairy product made with said milk. Thus, in embodiments the dairy product can comprise a derivative of the milk, such as one or more separated components of the milk, including but not limited to the milk fat. Accordingly the milk can be processed to separate milk components for including in a variety of dairy products. The disclosure includes making such products using conventional approaches, but by substituting milk of this disclosure for previously available milk.

In another aspect the present invention provides articles of manufacture, such as a kit. The kit can include a pharmaceutical composition comprising IL-8 in one or more sealed containers, i.e., glass or plastic vials. The kit can include a syringe, a catheter or other delivery device. For example, in the case of a catheter it may be an artificial insemination (A.I.) catheter, such as a Gilt A.I. catheter, or equivalents. The kit can also include a bag, such as a bag that is suitable for containing a solution and adapted for use with the catheter for introducing a solution into a mammal, for instance by intravaginal or intrauterine delivery. The kit may optionally include instructions for use of its contents either written on a paper or in a computer-readable format. The kit can also contain IL-8 that is to be mixed with a carrier, such as IL-8 in a lyophilized form, and in this case the kit can further include instructions for reconstituting the lyophilized IL-8 into a carrier/solution for administration to the mammal. For example, the carrier may be sterile water, normal saline, or phosphate buffered saline. The carrier may be provided in one or more separate vials.

In another aspect the instant disclosure comprises an article of manufacture. The article of manufacture comprises IL-8 produced as described herein, provided in packaging. The packaging can comprise a container, or can itself be a container. Any suitable container can be used, such as a plastic or glass container, including but not limited to plastic or glass vials. In various embodiments, the article of manufacture includes printed material. The printed material can be part of the packaging, or it can be provided on a label, or as paper insert or other written material included with the packaging. The printed material provides information identifying IL-8 as contents of the package, and instructs a consumer how to use the IL-8 to produce any one or any combination of the effects on mammals as described herein.

In view of the foregoing, and without intending to be bound by any particular theory, the present invention relates in part to the observation that a contributory factor that increases susceptibility to uterine diseases is the immunosuppression faced by cows during the periparturient period (Drackley, 1999; Cai et al., 1994; Kimura et al., 1999; Hammon et al., 2006; Galvao et al., 2010). Neutrophils are the main leukocyte type involved in placental release (Kimura et al., 2002), and in bacterial clearance after uterine (Hussain, 1989) and mammary gland (Paape et al., 2002) infection. Blood neutrophil function begins to decline prior to parturition, reaches a nadir shortly after parturition, and slowly returns to prepartum levels by about 4 weeks postpartum (Kehrli and Goff, 1989; Goff and Horst, 1997). Several factors can account for the loss in neutrophil function, such as increases in blood estradiol and cortisol concentrations around calving, and deficit in nutrients and minerals such as vitamins A and E, calcium, and selenium (Goff and Horst, 1997; Kimura et al., 2002; Hammon et al., 2006). Additionally, neutrophils from cows with retained placenta (RP) also have decreased migration ability and decreased myeloperoxidase activity (Kimura et al., 2002). Cows with the greatest influx of neutrophils into the uterus have reduced risk of bacterial infection and reduced incidence of endometritis (Gilbert et al., 2007). The migration of neutrophils into the mammary gland is also believed to play a role in clearance of mastitis pathogens (Paape et al., 2002). IL-8 is a chemoattractant for neutrophils; binding of IL-8 to its receptors (CXCR1 and CXCR2) in the neutrophil induces neutrophil activation, stimulates chemotaxis, and increases phagocytosis and killing ability (Mitchell et al., 2003). Because neutrophils play a role in the maintenance of endometrial health, an appropriate stimulus to selectively attract neutrophils into the uterus is believed to be needed. However, continued inflammation results in the development of chronic uterine disease, which impairs fertility and reduces dairy profitability (Dubuc et al., 2011; Lima et al., 2013). Therefore, the present invention provides a counter-intuitive approach to, in one aspect, provide therapy and/or prophylaxis of uterine conditions that are known to be positively correlated with inflammation by administering IL-8, which is also known to promote inflammation. In this regard, and without intending to be constrained by theory, the present disclosure includes an analysis of whether administration of IL-8 could, despite its pro-inflammatory properties, nevertheless recruit and activate neutrophils into the uterus, resulting in early influx of neutrophils into the uterine lumen, early detachment of the placenta, early bacterial contamination clearance, and ultimately a net positive result in the form of healthier more fertile dairy cows. As evidenced by the following Examples, administration of IL-8 does result in healthier and more fertile dairy cows, and unexpectedly improves their milk production and fat content of the milk, and increases their dry matter intake.

The following Examples illustrate specific embodiments of the invention and are not intended to be limiting.

Part I

This Example demonstrates effects of recombinant bovine interleukin-8 (rIL-8) on uterine health, metabolism, and milk yield in Holstein cattle. In particular, this Part I of the disclosure illustrates standardized cloning, production, and purification of rbIL-8 from bacterial culture. Two experiments were conducted to evaluate the safety of rbIL-8 in cattle and to assess its biological activity in vivo. Holstein heifers and non-pregnant lactating cows that received vaginal and intrauterine infusion of rbIL-8 underwent an increase in the proportion of neutrophils in their reproductive tract. Furthermore, heifers treated with rbIL-8 intravenously displayed a significant increase in white blood cell counts caused by an increase in neutrophil counts, at 6 hours after treatment. The results establish that the purification method presented here is effective, and that the purified rbIL-8 is biologically active and safe when applied to modulate immune responses in cattle.

The data described in this Part I was obtained in strict accordance with the recommendations of The Animal Welfare Act of 1966 (P.L. 89-544) and its amendments 1970 (P.L. 91-579), 1976 (P.L. 94-279), 1985 (P.L. 99-198) that regulate the transportation, purchase, care, and treatment of animals used in research.

The following materials and methods were used to obtain the data described in this Part I.

Cloning, production, and purification of recombinant bovine interleukin-8

Plasmid Construction.

Construct pET28-His-L-EK-IL8 was created by subcloning the bovine IL-8 cDNA from Trc-His-L-EK-IL8 into pET28A (Novagen, Darmstadt, Germany) using the restriction sites NheI and XhoI. The original Trc plasmid was constructed by PCR amplification of the codon-optimized bovine IL-8 cDNA ΔSS using the following primers: 5'-C GGCGCC GTG CTG TCT CGT ATG TCC ACC GAA C (SEQ ID NO: 11) and 5'-G CTCGAG TCA CGG ATC TTG TTT TTC TGC ACG (SEQ ID NO: 12). The PCR product was TA-cloned into pGEM T vector (Promega, Madison, Wis.), isolated by blue and white screening, and subsequently sequenced for confirmation. The correct clone was then digested with the restriction enzymes SfoI and XhoI and ligated into pTrcHis B vector (Invitrogen, Carlsbad, Calif.). To maintain a native version of IL-8 upon enterokinase cleavage, the Trc vector was prepared by digestion with BamHI followed by digestion with mung bean nuclease to remove the 5' overhang and create a blunt end for ligation; the vector was then digested with XhoI. The final construct was confirmed by DNA sequencing.

The PCR amplification protocol described above results in bovine IL-8 starting with the following amino acid sequence: AVLSRMSTE (SEQ ID NO: 13). This approach included amplification of the biologically active region of bovine IL-8, but did not clone the bovine IL-8 leader sequence. When this was cloned into the plasmid vector, it was expressed behind a His-tag with an open reading frame encoding the following sequence:

(SEQ ID NO: 14)
*MGSSHHHHHHSSGLV**PRGSHMASMTGGQ* *QMGRDLYDDDDK*AVLSRMST

ELRCQCIKTHSTPFHPKFIKELRVIESGPHCENSEIIVKLTNGNEVCLNP

KEKWVQKVVQVFVKRAEKQDP.

In this sequence, bold and italicized amino acids are encoded by the plasmid. Non-bold and non-italics is the active region of bovine IL-8, without the bovine IL-8 leader sequence. This form of IL-8 is one of several forms encompassed by this disclosure.

Production of rbIL-8.

An overnight culture of pET28-His-L-EK-IL8 was used to inoculate LB broth supplemented with Kanamycin 30 μg/ml. Cultures were incubated for 3 hours (until an O.D.$_{600\,nm}$ of 0.6 was reached) at 37° C., shaking at 200 rpm. To induce protein expression, IPTG was added to each culture flask and cultures were further incubated for 4 hours at 37° C., shaking at 200 rpm. Cells were harvested by centrifugation at 12,000 g for 8 minutes at 4° C. Supernatant was discarded and pellets were stored at −20° C.

Cell pellets were resuspended in 10 mL of protein buffer A (250 mM sodium phosphate monobasic and 1500 mM NaCl; pH 7.4) per liter of culture. Cell suspensions were combined, placed on ice, and 10 μL per 10 mL of cell suspension of protease inhibitor cocktail (Sigma, USA) was added. Cells were then sonicated on ice with 2-s pulses at 3-s intervals 60 times using a Misonix Ultrasonic Liquid Processor Q500 (QSonica LLC, CT, USA) at 80% amplitude. Sonicated cells were centrifuged for 30 min at 12,000×g at 4° C. The soluble fraction of the supernatant was used for purification of His-tagged recombinant proteins under native conditions with Talon metal affinity chromatography resin (Clontech Laboratories, Takara Korea Biomedical Inc.), according to the manufacturer's protocol. Automated purification of the tagged proteins was performed using the AKTA-pure instrument (GE Healthcare Life Sciences) controlled by UNICORN software. The clear cell lysate prepared as described above was loaded at flow rates recommended by the manufacturer (i.e. between 2 and 5 mL/min) onto HiScale chromatography columns pre-packed with Talon metal affinity chromatography resin (Clontech Laboratories, Takara Korea Biomedical Inc.) previously equilibrated in buffer A (250 mM sodium phosphate monobasic and 1500 mM NaCl; pH 7.4). Protein was eluted with a two-step gradient (6% and 100%) of buffer B (buffer A plus 150 mM imidazole; pH 7.4). Loading and purifications were performed at 4° C. All chromatography columns were purchased from GE Healthcare. The fractions were analyzed by SDS-polyacrylamide gel electrophoresis (PAGE). Fractions containing the protein were concentrated using Amicon Ultra-15 Centrifugal Tubes with Ultracel-3 membrane (Millipore). Up to 15 ml of the protein sample was added to the filter and centrifuged at 4,200×g for 30 min at 4° C. The flow-through was discarded and the process was repeated until all fraction samples were combined. Buffer exchange was then completed using the above filters by washing the final protein sample with buffer A (the volume in the filter tube was brought up to 15 ml with buffer A and centrifuged at 4,200×g for 30 min at 4° C.). This was completed three times total to remove buffer B and any imidazole that may be present. The final protein sample was filter sterilized and stored in 25% glycerol at −20° C. Protein concentration was determined by completing Bradford assay. The columns on the AKTA system were washed and regenerated according to the manufacturer's instructions for several cycles.

Assessing the Presence of rbIL-8 after Purification.

Western blot analysis was conducted using a 6HIS primary antibody to confirm the presence of the recombinant IL8 protein. In brief, extracted proteins were separated using 14% SDS-PAGE and transferred onto an Immun-Blot PVDF membrane (BIO-RAD). The PVDF membrane was incubated in 5% non-fat milk in Tris-buffered saline with Tween 20 (TBST) buffer (20 mM Tris, 150 mM NaCl, 0.01% Tween 20), shaking at room temperature for 1 h. After incubation, the liquid phase was discarded and PVDF membrane was further incubated at room temperature, shaking overnight in 5% milk supplemented with a 6×HIS monoclonal antibody at 1:1000 dilution (Clontech Laboratories). Three wash steps were performed by incubating in TBST and shaking for 5 min at room temperature. To confirm the presence of the recombinant 6His-IL-8, 5% non-fat milk containing the secondary goat anti-mouse antibody at 1:1000 dilution (ThermoFisher Scientific) was added and incubated shaking at room temperature for 1 h. The wash steps were repeated and the protein was visualized using Western Lightning® ECL Pro (PerkinElmer Inc.).

In-Vitro Assessment of Neutrophil Chemotaxis Induced by rbIL-8

Bovine blood polymorphonuclear (PMN) cells were isolated as described by Roth and Kaeberle (1981). In brief, blood samples were centrifuged for 20 min at 1000×g and the plasma and buffy coat aspirated and discarded. PMN cells were separated from the remaining packed red blood cells by using two-volume hypotonic lysis. The PMN cells (primarily neutrophils, but also basophils and eosinophils) were adjusted to a final concentration of $6.0 \times 10^7$ cells/ml in Hanks Balanced Salt Solution (Grand Island Biological Co., Grand Island, N.Y.) at room temperature until they were subjected to functional assays.

The chemotactic assay was conducted in a 96-well chemotaxis chamber (Neuro Probe MBA96) fitted with a 5-µm framed filter following the manufacturer's instructions and as described previously (Shi, Kornovski et al. 1993). The framed filter is a polycarbonate membrane bonded to a rigid flame possessing a pressure-sensitive adhesive on the lower side. The 96-well chemotaxis chamber has a lower plate with a recess that accepts a microtiter plate, an upper plate with 96 through-holes, and a silicone rubber gasket secured to the underside of the upper plate with retention pins. The upper and the lower plates are attached to each other with a hinge on one side and latches on the opposite side. To set up the apparatus, a microtiter plate was filled (400 µL) with medium containing chemoattractant or medium alone and placed in the recess of the lower plate. The framed filter was then placed on top of the filled microtiter plate with the adhesive side down. The upper plate, with the gasket installed, was then closed on the filter and latched to the lower plate. 200 µL of cell suspension (between $6 \times 10^4$ and $6 \times 10^6$ cells) in PBS was then added to the wells of the upper plate. Assays were carried out at 37° C. in 5% CO2/95% air for 2 h. Upon completion of incubation, the medium in the wells of the upper plate was replaced with 200 µL of PBS-EDTA and incubated at 4° C. for 30 min. The microplate containing the filter was centrifuged to harvest cells that responded to rbIL-8.

Quantification of cells that responded to chemotaxis was performed using a rapid colorimetric assay based on reduction of 3-(4,5-dimethylthiazol-2-yl)-2,5-diphenyltetrazolium bromide (MTT; Sigma-Aldrich, St. Louis, Mo.), which measures living cells (Mosmann, 1983). Reduced MTT was measured based on optical density at 540 nm ($OD_{540}$) using a microplate reader (BioTek Instruments, Winooski, Vt.).

In-Vivo Assessment of Neutrophil Chemotaxis Induced by rbIL-8

Three experiments were conducted to assess the in vivo biological activity of rbIL-8 in treating animals based on recruitment of granulocytes into the reproductive tract, and to assess the effect of local and systemic rbIL-8 stimulation on the dynamics of circulating white blood cells. Given the possibility that the effects of rbIL-8 are dependent on animal's age and physiological status, in-vivo chemotaxis trials were conducted using 1-year-old Holstein heifers and non-pregnant lactating Holstein cows.

Animals and Facilities.

Holstein heifers and lactating cows from a single farm located near Ithaca, N.Y. were used in this study within the period of March to June 2014. The farm milked 3,300 Holstein cows 3 times daily in a double 52-stall parallel milking parlor. Cows were housed in free-stall barns equipped with sprinklers, fans, and sand-bedded stalls. Animals had ad libitum access to water and received a TMR ration formulated to meet or exceed nutritional requirements of each category.

Study Design and Data Collection.

Study 1:

One-year old Holstein heifers (n=20) were randomly allocated to receive a single intravaginal infusion containing 1.125 mg of rbIL-8 diluted in 20 mL of saline solution (rbIL-8; n=10) or 20 mL of sterile saline solution (CTR, n=10) on study d 0. Initial dose of rbIL-8 was based on data from other species in which a dose of 25 µg/kg has previously been shown to be effective rabbits (Ley et al., 1993), and suggested to elicit significant local and/or systemic inflammatory reactions (Watanabe et al., 2012). Animal health status was monitored continuously by one of the veterinarians of the research team for first 12 h after treatment and once daily until study d 4. Animals were evaluated for rectal temperature (fever>39.5° C.), respiratory pattern (0=breathing slowly and evenly; 1=panting or breathing with obvious labor; 2=rapid breathing), attitude (0=alert; 1=depressed; 2=non-responsive), hydration status (0=euhydrated; 1=skin tented 2 to 5 s; 2=skin tented 6 to 10 s; and 3=skin tented≥10 s), and signs of pain or discomfort. Potential behavioral signs of pain were recognized and evaluated according to Forkman pain chart evaluation (Forkman 2015). Treatment was performed after cows were restrained in headlock stanchions, the external genital area of cows was washed with warm water and soap and dried with paper towels followed by a 30% iodine spray before treatment. The rbIL-8 or sterile saline solution was gently infused into the vaginal tract with individually wrapped sterile infusion tubes (Continental Plastic Corp., Delavan, Wis.) capped with a 5-mL screw-tip sterile syringe (Becton, Dickinson and Company, Franklin Lakes, N.J.) and deposited at the cranial aspect of the vagina. Cytological evaluation of the vaginal epithelium was performed before infusion and 3 h later using a cytobrush (Cytobrush Plus GT; Coopersurgical, Trumbull, Conn.) attached to a stainless-steel gun adapted for use in cattle (Kasimanickam et al., 2004). In brief, study cows were restrained in a head-lock stanchion and the perineum and vulva were cleansed with a paper towel and disinfected with 70% ethanol prior to sample collection. The lips of the vulva were opened and the cytobrush gun was inserted into the vagina. After swabbing (by gently rubbing or rolling) the vaginal wall, the applicator is removed and rolled (not smeared) onto a glass slide. Routine Diff-Quik staining was performed after air-drying the slide. Each slide was examined by the same examiner under bright-field microscopy at 400× magnification to aid in particular cell identification. The examiner counted 200 cells from each slide and the percentage of PMN leukocytes among all other cells was determined.

Study 2:

To ensure that the biological effects observed after treatment were in response to rbIL-8 and not to other proteins expressed by the vector; non-pregnant lactating Holstein cows (n=31) were allocated randomly to receive an intra-uterine infusion with 1,125 µg of rbIL-8 diluted in 20 mL of saline solution (rbIL-8; n=11), resin-purified lysate of *E. coli* BL21 that was not transfected with the plasmid coding for rbIL-8 diluted in 20 mL of saline solution (*E. coli*; n=10), and a negative control infused with 20 mL of saline solution (CTR, n=10). Intrauterine infusion of purified lysate of *E. coli* BL21 (free of the plasmid coding for rbIL-8) was prepared as using the same technique that was described for the rIL-8 preparation. Cows were restrained in headlock stanchions and the perineal area and vulva were cleansed with paper towels and disinfected with 70% ethanol before treatments were applied. A sterile uterine infusion pipette was manipulated into the uterus, the tip was exposed to the uterine lumen, and the treatment was infused into the uterus. Cytological evaluation of the endometrium was performed before infusion and 24 h after using a cytobrush (Cytobrush Plus GT; Coopersurgical, Trumbull, Conn.) attached to a stainless-steel gun adapted for use in cattle (Kasimanickam et al., 2004). Before sample collection, the perineum and vulva were cleansed as described in study 1. In brief, the lips of the vulva were opened and the cytobrush gun was inserted into the vagina and passed through the cervix. Once inside of the uterine body, the cytobrush was exposed, rotated clockwise a full 360 degrees to obtain cellular material from the endometrium, and then withdrawn inside of the gun. Slides for cytological examination were prepared on farm by rolling the cytobrush on a clean glass microscope slide and air-dried before being stained with modified Wright-Giemsa stain (Diff-Quik 1, Dade Diagnostics, West Monroe, La.). Slides were examined as described in study 1.

Study 3.

This approach comprised use of a single dose of rbIL-8 via two different routes (intravenous and intravaginal) to evaluate the effect of local and systemic rbIL-8 stimulation on the dynamics of circulating white blood cells. In total, 30 non-pregnant 8-month-old Holstein heifers were randomly allocated into 1 of 3 treatments: intravenous rbIL-8 (n=10); intravaginal rbIL-8 (n=10); or intravaginal saline (n=10). The intravenous dose was composed of 1,125 µg of rbIL-8 diluted in 5 mL of saline solution infused into the jugular vein. The intravaginal treatment contained the same dose of 1,125 µg of rbIL-8 diluted in 20 mL of saline solution or 20 mL of saline solution. Intravaginal treatments were administered as described in study 1.

Animal health status (i.e. respiratory pattern, attitude, hydration status, and signs of pain or discomfort) was monitored continuously by one of the veterinarians of the research team for the next 12 h after treatment and once daily until the last day of the study at day 14. Rectal temperature was recorded right before treatment (0 h) and at 2 h, 6 h and 24 h. For determination of differential leukocyte counts, blood samples were collected at enrollment and at 10 min, 2 h, 4 h, 6 h, 1 d, 2 d, 7 d, and 14 d post treatment from the coccygeal vein/artery were drawn into 2-ml syringe and transferred immediately into commercial 2-mL Vacutainer tubes containing lithium-heparin (Becton-Dickinson, U.S.A.). Blood samples were submitted to the New York State Veterinary Diagnostic Laboratory for complete blood count analysis.

Statistical Analyses

Continuous variables were analyzed by ANOVA using the GLIMMIX procedure of SAS version 9.3 (SAS Institute Inc., Cary, N.C.). Results from in vitro chemotactic assays were analyzed by one-way ANOVA. Data from in vivo studies were analyzed by repeated measures ANOVA. Treatment, time, and the interaction of treatment and time were included as fixed effects into the statistical models whereas animal identification number was added as a random effect. For studies with more than two treatments, pairwise comparisons were performed using the method of Tukey. Tests for normality of residuals and homogeneity of variances were conducted for each dependent variable. Results are presented as least squares means and standard error of the means. Differences with $P \leq 0.05$ were considered significant and those with $0.05 < P \leq 0.10$ were considered tendencies.

The following results were obtained using the materials and methods described for this Part I.

Expression and Purification of Recombinant Bovine IL-8

Expression of the rbIL-8 protein was analyzed by 12% Tris-glycine SDS-PAGE stained with Coomassie brilliant blue. The results showed that rbIL-8 was expressed successfully (data not shown). Western blot analysis also confirmed the overexpression of the rbIL-8 by a specific monoclonal antibody against bovine native IL-8 (data not shown). Recombinant bovine IL-8 is known to be a thermostable protein, so to determine optimal recovery conditions, we heated the cell lysate under different temperature regimens (i.e., different temperatures for the same time, and the same temperature for different times). The results showed that most other bacterial proteins could be removed by heating the cell lysate at 70° C. for 10 min and that after this step the rbIL-8 protein could be further purified by using an AKTA pure chromatography system. The purity of the final rbIL-8 was more than 95% (data not shown).

Chemotactic Activity of rbIL-8

In Vitro Chemotactic Assays

Results from in vitro chemotactic assays confirmed the bioactivity of rbIL-8. Based on optical density values, chemoattractant properties of rbIL-8 was 10-fold greater ($P \leq 0.05$) compared with control wells (FIG. 1A).

Study 1

Figure 1:
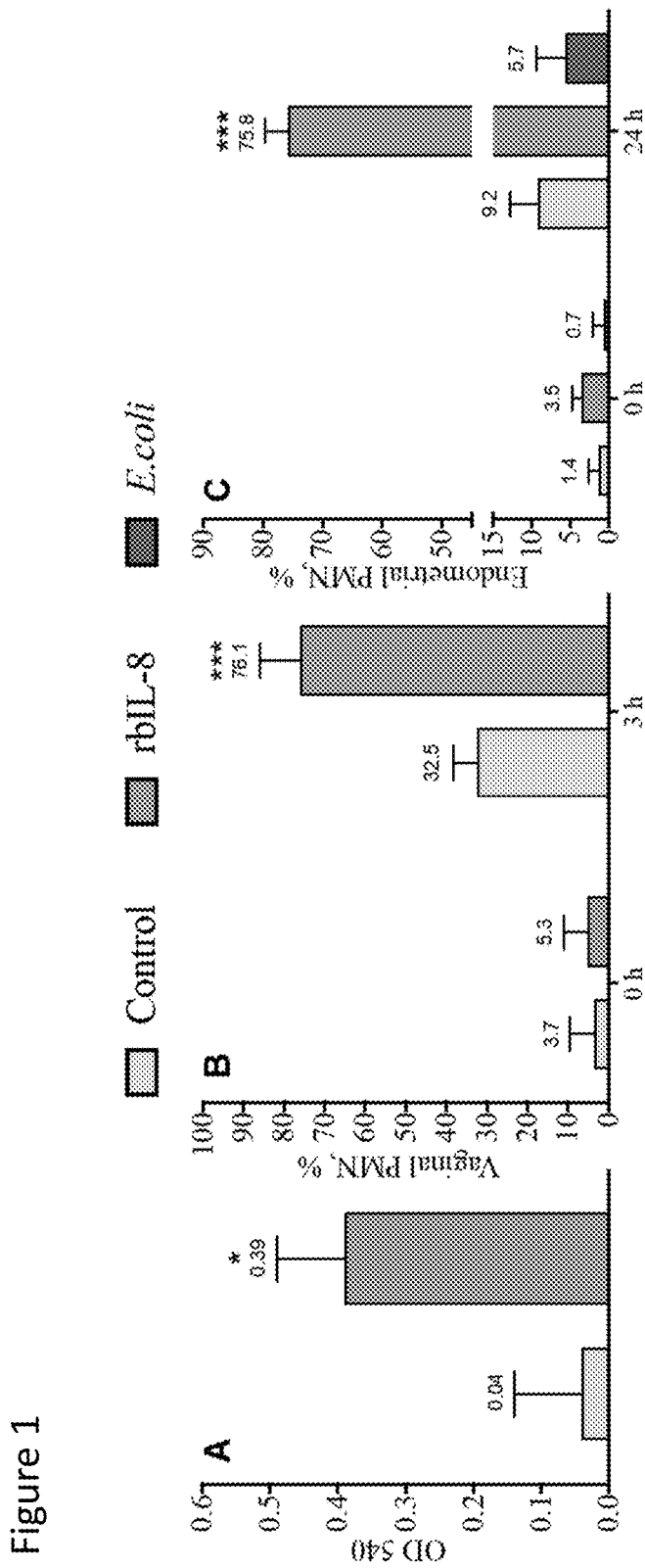
FIG. 1. Effect of rbIL-8 on in vitro chemotaxis is presented in figure A. The proportion of polymorphonuclear cells (PMN) in the vagina (B) of heifers treated with rbIL-8 or saline solution is presented in figure B (study 1). The proportion of PMN in the endometrium of cows treated with rbIL-8, *E. coli*, or saline solution is presented in figure C (study 2). For study 1, Holstein heifers received 1,125 μg of rbIL-8 or saline solution intravaginally. For study 2, non-pregnant lactating Holstein cows received an intrauterine infusion with 1,125 μg of rbIL-8, resin-purified lysate of *E. coli* BL21 that was not transfected with the plasmid coding for rbIL-8 or saline solution. Error bars indicate SEM. *$P \leq 0.05$ ***$P \leq 0.001$.

Similar to in vitro results, an increase in vaginal neutrophils was observed in heifers treated with rbIL-8 within 3 h of treatment, but not in control heifers (FIG. 1B).

Study 2

Intrauterine infusion of rbIL-8 increased the proportion of PMN cells in uterine cytological samples from 3.5% before treatment to 75.8% 24 h later—an increase that was not observed in untreated controls and cows treated with resin-purified lysate of *E. coli* BL21 that was not transfected with the plasmid coding for rbIL-8 (FIG. 1C). These results indicate that the rbIL-8 is biologically active and successfully induced neutrophil activation, chemotaxis, and diapedesis both in vitro and in vivo.

Study 3—Route Administration Trial

Figure 2:
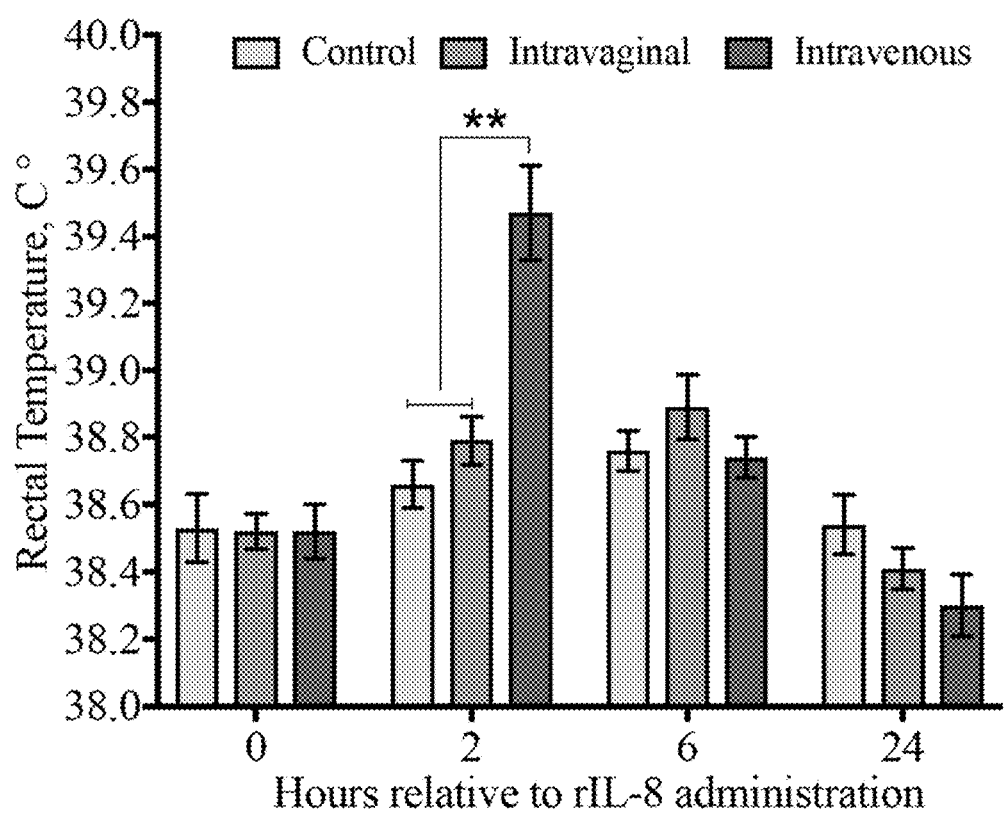
FIG. 2. Rectal temperature (° C.) of non-pregnant heifers that received a single intravenous rbIL-8, intravaginal rbIL-8 dose, or saline solution at 0 h (before treatment), 6 h, and 24 h relative to the rbIL-8 administration (study 3). Error bars indicate SEM.*$P \leq 0.001$, $P \leq 0.01$, *$P \leq 0.05$.

Intravenous injection of rbIL-8 resulted in a transient increase in rectal temperature, which was only observed at the measurement taken 2 h after treatment compared with heifers treated with rbIL-8 intravaginally or untreated controls (FIG. 2). No difference in rectal temperature among groups was observed at the measurements taken 6 and 24 h post treatment. Respiratory pattern, attitude, hydration status, and signs of pain or discomfort were not affected by treatment and remained within normal limits for the duration of the study.

Figure 3:
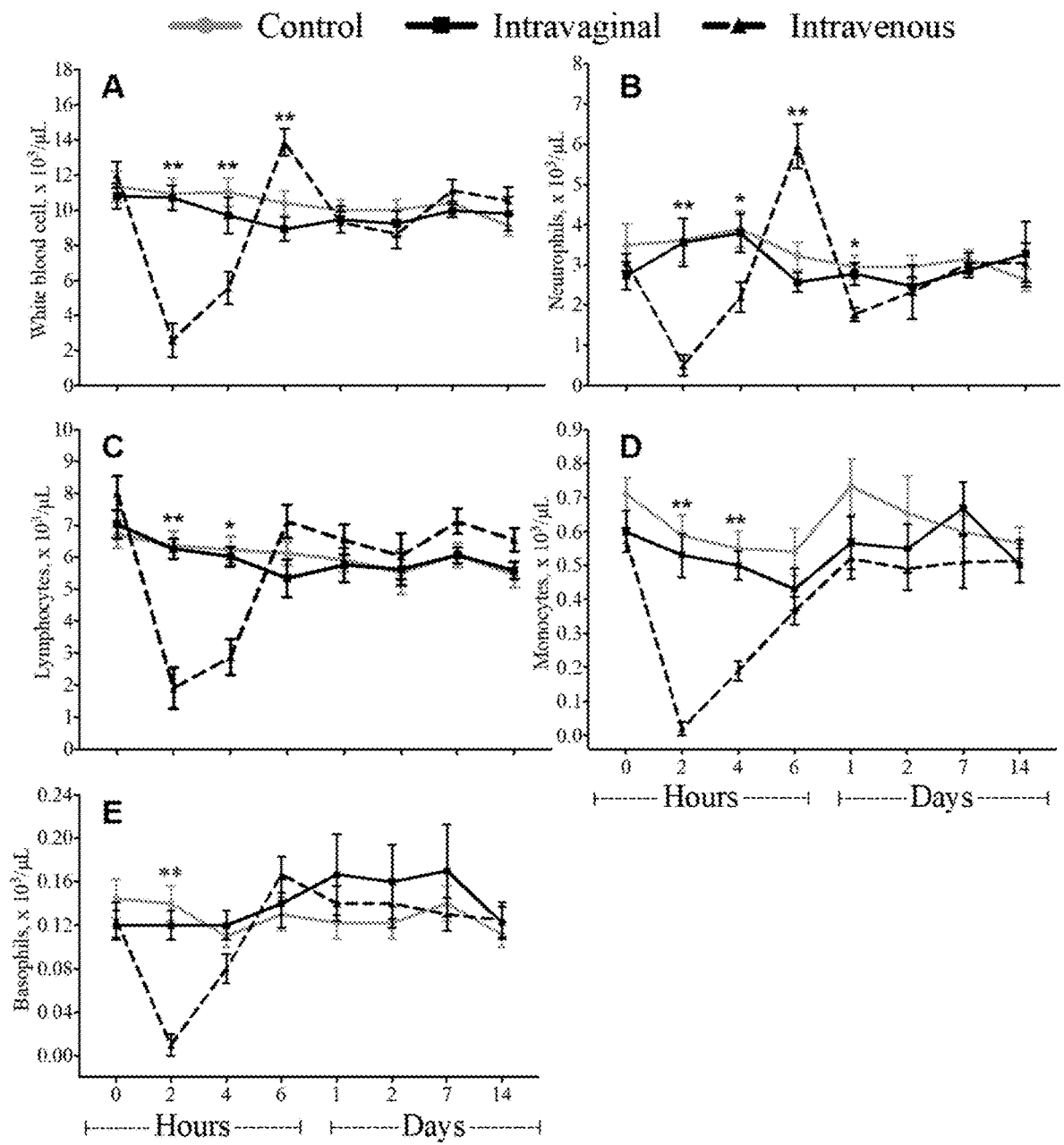
FIG. 3. The dynamic of the concentration of white blood cells (A), neutrophils (B), lymphocytes (C), monocytes (D), and basophils (E) of non-pregnant heifers treated with rbIL-8 intravenously or intravaginally, or saline solution (study 3). Blood samples were collected subsequently on 2 h, 4 h, 6 h, and on days 1, 2, 7 and 14. Error bars indicate SEM.*$P \leq 0.001$, $P \leq 0.01$, *$P \leq 0.05$.

White blood cell counts in control animals and those treated with rbIL-8 intravaginally were stable during the entire experimental period (FIG. 3A). On the other hand, animals treated with rbIL-8 intravenously displayed a marked reduction in white blood cells 2 h after injection that was sustained until 4 h post treatment. Such reduction was driven by a decrease in blood counts of neutrophils (FIG. 3B), lymphocytes (FIG. 3C), monocytes (FIG. 3D), and basophils (FIG. 3E). Basophil counts in heifers treated with rb-IL-8 intravenously returned to the same levels as the other two groups at 4 h after treatment. Nevertheless, counts of neutrophils, lymphocytes, and monocytes remained lower ($P<0.05$) at 4 h after treatment in heifers treated with rbIL-8 intravenously compared with counterparts treated with rbIL-8 intravaginally and controls. At 6 hours after treatment, heifers treated with rbIL-8 intravenously displayed a rebound in white blood cell counts (FIG. 3A) driven primarily by a dramatic increase in neutrophil counts (FIG. 3B).

This Part I demonstrated standardization of the process of cloning, production, and purification of rbIL-8 from bacterial culture. We tested different heating temperatures and heating times for partial purification of rbIL-8. We found that partial purification was achieved after heating the bacterial lysate at 70° C. for 10 min, after which most of the bacterial proteins were removed. Similar results have been reported for human recombinant IL8 (Hou et al., 2005). After a column chromatography step, this purification procedure resulted in final yields of 1.2 mg of >95% pure rbIL-8 per liter of *E. coli*-BL21 culture. Similar results were seen by Caswell et al. (1999), who reported a protein yield of 0.7 mg of purified recombinant bovine IL-8 for every liter of induced *E. coli* culture. We then conducted functional tests, both in vitro and in vivo, to ensure that rbIL-8 was biologically active. The results of our in vitro and in vivo tests indicated that rbIL-8 can be successfully produced by *E. coli*-BL21 and that the purified protein is biologically active. This approach is included in the disclosure.

The development of disease-like signs that impair the wellbeing and potentially performance was a concern of treating dairy cows with rbIL-8. We completed two studies to evaluate potential negative effects of rbIL-8 treatment in cattle; however, no major adverse effects on health parameters and welfare measures were observed in heifers and lactating cows. Experimental animals that received intrauterine infusion of rbIL-8 were monitored constantly in case of signs of disease, but no adverse effects were evident. We also demonstrated that vaginal and intrauterine infusion with rbIL-8 is effective in recruiting neutrophils into the reproductive tract.

Bacteria-derived factors are particularly suitable for investigation of inflammatory and immune processes because they are often potent immune-stimulators. A study showed that several bacterial species secrete substances with chemotactic activity toward leukocytes into the culture supernatant (Tsukamoto et al., 1999). That study showed that bacteriocin purified from a culture supernatant of *Streptococcus mutans* induced chemotaxis of human PMN leukocytes and monocytes. However, in the present disclosure, the presence of such extraneous immune stimulators (i.e. contaminants from rbIL-8 production) able to elicit intrauterine granulocyte recruitment was ruled out. Non-pregnant lactating Holstein cows treated with an intrauterine infusion of rbIL-8 underwent a major increase in the proportion of PMN whereas controls treated with resin-purified lysate of *E. coli* BL21 that did not have the expression plasmid coding for IL-8 did not. Taken together, these results indicate that the produced rbIL-8 is highly pure and biologically active and can be used safely to modulate immune responses in cattle.

The elevation in body temperature in response to rbIL-8 observed 2 h after intravenous treatment with intravenous rbIL-8 was expected as the pyrogenic effect of IL-8 has been reported previously (Rothwell et al., 1990; Zampronio et al., 1995). Interestingly, in another study by Zampronio et al. (1994) recombinant human IL-8 injected intravenously into rabbits was not pyrogenic whereas intracerebroventricular injection induced fever which might be attributed to the lower dosage used in that study. In addition, the range of mediators capable of producing fever in different species, together with their doses and routes of administration vary widely. For example, intravenous doses of lipopolysaccharide, IL-1β, and TNF-α that induce fever in rabbits and humans are smaller than that in rats (Kettelhut and Goldberg, 1988; Zampronio et al., 1994; Zampronio et al., 2000). Similarly, intravenous administration of IL-6 at doses 20 times higher than that which induces fever in rabbits does not promote fever in rats (Helle et al., 1988; Rothwell et al., 1990).

Intravenous administration of rbIL-8 altered the peripheral blood leukocyte distribution in this example. Cytokines are well-known promoters of white blood cell differentiation (Zhu and Emerson, 2002). In this Part I, rbIL-8 administration decreased the white blood population within the first 4 h after intravenous injection; however, a sustained alteration past this point was not observed. Specifically, the levels of blood neutrophils, basophils, lymphocytes, and monocytes behaved similarly after treatment with a significant drop in white blood cells in the intravenous treated animals observed 2 h after treatment, followed by a relative increase at 4 h after treatment. However, neutrophils were the only leukocyte to increase significantly at 6 h after intravenous rbIL-8 treatment.

The results from this Part I show that the purification method described herein was effective and resulted in biologically active rbIL-8 that can be used safely to modulate immune responses in cattle. In particular, we have standardized the process of cloning, production, and purification of rbIL-8 from bacterial culture. Subsequent column chromatography resulted in final purified yields of 1.2 mg of >95% pure rbIL-8 per liter of *E. coli* culture. Experiments were conducted to evaluate the safety of treating animals with rbIL-8 and to assess its biological activity in vivo. No adverse effects on health and welfare were observed during the preliminary studies conducted in heifers, and lactating cows that were allocated to receive 1.125 µg of rbIL-8 intravenously or intrauterine infusion. Intrauterine infusion with 1.125 µg of rbIL-8 induced a 20-fold increase in the proportion of PMN cells in uterine cytology, which was not observed in resin-purified lysate of *E. coli* BL21 that was not transfected with the plasmid coding for rbIL-8. Additionally, intravenous treatment with rbIL-8 have marked effects on white blood cell populations including general leukopenia between 2 and 4 h after intravenous injection and a rebound increase in neutrophil counts at 6 h. These results show that this purification method is effective and results in biologically active rbIL-8 that can be used safely in cattle.

References for Part I. This reference listing, nor any other reference cited herein, is meant to be an indication that any reference is material to patentability.

Baggiolini, M., A. Walz, and S. L. Kunkel. 1989. Neutrophil-activating peptide-1/interleukin 8, a novel cytokine that activates neutrophils. J. Clin. Invest., 84:1045-1049.

Caswell, J. L., D. M. Middleton, and J. R. Gordon. 1999. Production and functional characterization of recombinant bovine interleukin-8 as a specific neutrophil activator and chemoattractant. Vet. Immunol. Immunopathol., 67:327-340.

Elliott, C. L., D. M. Slater, W. Dennes, L. Poston, and P. R. Bennett. 2000. Interleukin 8 expression in human myometrium: changes in relation to labor onset and with gestational age. Am. J. Reprod. Immunol., 43:272-277.

Forkman, K. B. G. P. H. A. L. M. B. (2015). "Pain evaluation in dairy cattle." *Applied Animal Behaviour Science* Volume 171 (October 2015): Pages 25-32.

Gilbert, R. O., S. T. Shin, C. L. Guard, H. N. Erb, and M. Frajblat. 2005. Prevalence of endometritis and its effects on reproductive performance of dairy cows. Theriogenology, 64:1879-1888.

Goff, J. P., and R. L. Horst. 1997. Physiological changes at parturition and their relationship to metabolic disorders. J. Dairy Sci., 80: 1260-1268.

Gunnink, J. W. 1984a. Post-partum leucocytic activity and its relationship to caesarian section and retained placenta. Vet. Q., 6:55-57.

Gunnink, J. W. 1984b. Retained placenta and leucocytic activity. *Vet. Q.*, 6:49-51.

Hammon, D. S., I. M. Evjen, T. R. Dhiman, J. P. Goff, and J. L. Walters. 2006. Neutrophil function and energy status in Holstein cows with uterine health disorders. Vet. Immunol. Immunopathol., 113:21-29.

Hechtman, D. H., M. I. Cybulsky, H. J. Fuchs, J. B. Baker, and M. A. Gimbore. 1991. Intravascular interleukin-8: an inhibitor of polymorphnuclear leukocyte accumulation at sites of acute inflammation. J. Immunol., 147:8863.

Helle, M., J. P. Brakenhoff, E. R. De Groot, and L. A. Aarden. 1988. Interleukin 6 is involved in interleukin 1-induced activities. Eur. J. Immunol., 18: 957-959.

Heuwieser, W., and E. Grunert. 1987. Steroid hormone profile in the afterbirth expulsion period of cattle, Dtsch. Tierarztl. Wochenschr., 94:311-314.

Hou, D., Z. Yan, J. Shi, W. Han, and Y. Zhang. 2005. Expression and one-step ion-exchange purification of (AAR)IL-8 (human IL-8 receptor antagonist). Protein Expr. Purif., 44:104-109.

Hussain, A. M. 1989. Bovine uterine defense mechanisms: a review. Zentralbl Veterinarmed B, 36:641-651.

Kasimanickam, R., T. F. Duffield, R. A. Foster, C. J. Gartley, K. E. Leslie, J. S. Walton, and W. H. Johnson. 2004. Endometrial cytology and ultrasonography for the detection of subclinical endometritis in postpartum dairy cows. Theriogenology, 62: 9-23.

Kehrli, M. E., Jr., B. J. Nonnecke, and J. A. Roth. 1989. Alterations in bovine neutrophil function during the peri-parturient period. Am. J. Vet. Res., 50:207-214.

Kettelhut, I. C., and A. L. Goldberg. 1988. Tumor necrosis factor can induce fever in rats without activating protein breakdown in muscle or lipolysis in adipose tissue. J. Clin. Invest., 81:1384-1389.

Kimura, K., J. P. Goff, M. E. Kehrli, Jr., and T. A. Reinhardt. 2002. Decreased neutrophil function as a cause of retained placenta in dairy cattle. J. Dairy Sci., 85: 544-550.

Laham, N., S. P. Brennecke, and G. E. Rice. 1999. Interleukin-8 release from human gestational tissue explants: effects of gestation, labor, and chorioamnionitis. Biol. Reprod., 61:823-827.

Ley, K., J. B. Baker, M. I. Cybulsky, M. A. Gimbrone, Jr., and F. W. Luscinskas. 1993. Intravenous interleukin-8 inhibits granulocyte emigration from rabbit mesenteric venules without altering L-selectin expression or leukocyte rolling. *J. Immunol.*, 151:6347-6357.

Mitchell, G. B., B. N. Albright, and J. L. Caswell. 2003. Effect of interleukin-8 and granulocyte colony-stimulating factor on priming and activation of bovine neutrophils. Infect. Immun., 71:1643-1649.

Morsey, M. A., Y. Popowych, J. Kowalski, G. Gerlach, D. Godson, M. Campos, and L. A. Babiuk. 1996. Molecular cloning and expression of bovine interleukin-8. Microb. Pathog., 20:203-212.

Mosmann, T. 1983. Rapid colorimetric assay for cellular growth and survival: application to proliferation and cytotoxicity assays. J. Immunol. Methods, 65:55-63.

Paape, M., J. Mehrzad, X. Zhao, J. Detilleux, and C. Burvenich. 2002. Defense of the bovine mammary gland by polymorphonuclear neutrophil leukocytes. J. Mammary. Gland. Biol. Neoplasia., 7:109-121.

Peters, M. D., I. D. Silveira, and V. Fischer. 2015. Impact of subclinical and clinical mastitis on sensitivity to pain of dairy cows. Animal, 9: 2024-2028.

Roth, J. A., and M. L. Kaeberle. 1981. Isolation of neutrophils and eosinophils from the peripheral blood of cattle and comparison of their functional activities. J. Immunol. Methods, 45:153-164.

Rothwell, N. J., A. J. Hardwick, and I. Lindley. 1990. Central actions of interleukin-8 in the rat are independent of prostaglandins. Horm. Metab. Res., 22:595-596.

Sheldon, I. M., G. S. Lewis, S. LeBlanc, and R. O. Gilbert. 2006. Defining postpartum uterine disease in cattle. Theriogenology, 65:1516-1530.

Shi, Y., B. S. Kornovski, R. Savani and E. A. Turley (1993). "A rapid, multiwell colorimetric assay for chemotaxis." *J Immunol Methods* 164(2): 149-154.

Sigrell, J. A., P. Eklund, M. Galin, L. Hedkvist, P. Liljedahl, C. M. Johansson, T. Pless, and K. Torstenson. 2003. Automated multi-dimensional purification of tagged proteins. J. Struct. Funct. Genomics, 4:109-114.

Stojkov, J., M. A. von Keyserlingk, J. N. Marchant-Forde, and D. M. Weary. 2015. Assessment of visceral pain associated with metritis in dairy cows. J. Dairy. Sci., 98: 5352-5361. Tsukamoto, Y., S. Fukutani, Y. Takayama, H. Fukushima, H. Sagawa, and M. Mori. 1990. Characterization of leukocyte chemotactic activity of bacteriocin from *Streptococcus mutans* Rm-10. *Inflammation*, 14:561-569.

Van Zee, K. J., E. Fischer, A. S. Hawes, C. A. Hebert, T. G. Terrell, J. B. Baker, S. F. Lowry, and L. L. Moldawer. 1992. Effects of intravenous IL-8 administration in non-human primates. J. Immunol., 148:1746-1752.

Watanabe, A., J. Hirota, S. Shimizu, S. Inumaru, and K. Kimura. 2012. Single intramammary infusion of recombinant bovine interleukin-8 at dry-off induces the prolonged secretion of leukocyte elastase, inflammatory lactoferrin-derived peptides, and interleukin-8 in dairy cows. Vet. Med. Int., 2012:172072.

Zampronio, A. R., M. E. Hoadley, G. Luheshi, N. J. Rothwell, G. E. de Souza, and S. J. Hopkins. 2000. Interleukin (IL)-6 release and fever induced by a pre-formed pyrogenic factor (PFPF) derived from LPS-stimulated macrophages. Eur. Cytokine Netw., 11:589-596.

Zampronio, A. R., C. A. Silva, F. Q. Cunha, S. H. Ferreira, I. R. Pela, and G. E. Souza. 1995. Indomethacin blocks the febrile response induced by interleukin-8 in rabbits. Am. J. Physiol., 269: R1469-1474.

Zampronio, A. R., G. E. Souza, C. A. Silva, F. Q. Cunha, and S. H. Ferreira. 1994. Interleukin-8 induces fever by a prostaglandin-independent mechanism. Am. J. Physiol., 266:R1670-1674.

Zhu, J., and S. G. Emerson. 2002. Hematopoietic cytokines, transcription factors and lineage commitment. Oncogene, 21:3295-3313.

Part II

This Part II demonstrates effects rbIL-8 treatment on health, metabolism, and milk production in Holstein cattle, and in particular provides analysis of the effects of rbIL-8 on postpartum uterine health, hyperketonemia, and milk production. The incidences of retained placenta, clinical metritis, puerperal metritis, and endometritis were evaluated. Recombinant bIL-8 treatment altered the serum levels of some metabolites, reduced the incidence of hyperketonemia, but was not associated with the occurrence of postpartum uterine diseases. Both intrauterine infusion and intravenous injection of rbIL-8 induced a significant long-lasting increase in milk production. Specifically, the effects of rbIL-8 on milk production were evaluated in two additional studies (study 2 and 3 of this Part II) to evaluate whether a single administration of rbIL-8 within 12 h of parturition improves lactation performance in Holstein cows.

The following materials and methods were used to produce the results described in this Part II.

Ethics Statement

The research protocol was reviewed and approved by the Cornell University Institutional Animal Care and Use Committee (protocol number 2013-0039). The methods were carried out in accordance with approved guidelines.

Farm and Management

Three studies were conducted in a large commercial dairy farm located in Cayuga County near Ithaca, N.Y. The farm milked approximately 3,800 Holstein cows thrice daily in a rotary parlor with integrated milk meters that record individual production at every milking (DeLaval, Tumba, Sweden). Cows were housed in naturally ventilated free stall barns with concrete stalls bedded with manure solids. All cows were offered a TMR and feed was pushed up 8 times a day. Diets consisted of approximately 55% forage and 45% concentrate on a dry matter basis. Diets were formulated to meet or exceed the National Research Council nutrient requirements for lactating Holstein cows weighing 650 kg and producing 45 kg of 3.5% fat-corrected milk (National Research Council, 2001). Cow displaying signs of calving were moved to individual maternity pens for delivery, where trained farm personnel assisted with parturition as needed. After calving, cows were transferred to a postpartum pen where they remained for approximately 40 d. Farm's reproductive management used for the first service a Presynch-Ovsynch protocol in combination with estrus detection (Pursley et al., 1995, Moreira et al., 2001). A Resynch (Fricke et al., 2003) protocol was started in non-pregnant cows 33±3 d after previous inseminations. A voluntary waiting period of 50 d was used. Estrus was detected based only on electronic activity sensors worn around the neck (Alpro, DeLaval, Mo.).

Study Design, Treatments, and Sample Collection

Study 1.

In total, 213 cows (primiparous, n=104; multiparous, n=109) were enrolled in the study from July 2014 to August 2014. Cows were blocked by parity and, within block, randomly allocated into one of three treatment groups: control (CTR; n=67), low-dose of rbIL-8 (L-IL8; n=80), and high-dose of rbIL-8 (H-IL8; n=66). Cows allocated to L-IL8 and H-IL8 received an intrauterine infusion of 250 mL of saline solution containing 11.25 and 1,125 g of rbIL-8, respectively. Control cows received an intrauterine infusion of 250 mL of saline solution. Recombinant bovine IL-8 was produced and purified according to the methods described herein. Treatments were administered by the research team within 12 h of parturition. Cows were restrained in headlock stanchions and the perineal area was cleansed with paper towels and disinfected with 70% ethanol. A sterile gilt AI catheter (Livestock Concepts, Hawarden) attached to a 250 mL saline bag was introduced into the cranial vagina. The catheter was manipulated into the uterus, the tip was exposed to the uterine lumen, and the treatment was infused into the uterus.

Blood samples were collected from 60 cows (20 cows per treatment) on d 0 (before treatment), 1, 2, and 3 relative to calving via coccygeal vein/artery puncture into an evacuated tube without anticoagulant (Becton, Dickinson and Company, Franklin Lakes, N.J.). Blood samples were transported to the laboratory on ice and centrifuged at 2,000×g for 15 min at 4° C., Serum was harvested and frozen at −80° C. until assayed. For each cow, body condition scores (BCS) was recorded at enrollment and at 35 days in milk (DIM) by a single investigator using a 5-point scale with a quarter-point system, as previously described (Edmonson et al., 1989). Rectal temperature (RT) was measured at enrollment and at 3, 6, and 9 DIM using a digital thermometer (GLA M750, GLA Agriculture Electronics, CA). Milk yield was recorded at every milking using on-farm milk meters and monthly averages obtained during the first 6 months postpartum were used for statistical analyses.

Study 2.

A total of 164 primiparous cows were enrolled in the study from October 2015 to December 2015. Cows were randomly allocated into one of four treatment groups control (CTR; n=41), low-dose of rbIL-8 (L-IL8; n=41), medium-dose of rbIL-8 (M-IL8; n=41), and high-dose of rbIL-8 (H-IL8; n=41). Cows allocated to L-IL8, M-IL8, and H-IL8 received a single intrauterine infusion of 250 mL of saline solution containing 0.14, 14, and 1,400 μg of rbIL-8, respectively. Control cows received an intrauterine infusion of 250 mL of saline solution. Treatments were administered within 12 h of parturition as described in study 1. Body condition score was scored at enrollment and at 35 DIM. Rectal temperature was recorded at enrollment and at 3 and 10 DIM using a digital thermometer (GLA M750, GLA Agriculture Electronics, CA). Milk yield was recorded at every milking using on-farm milk meters and monthly averages obtained during the first 6 months postpartum were used for statistical analyses.

Study 3.

A total of 39 cows (primiparous, n=20; multiparous, n=19) were enrolled in the study from March 2016 to April 2016. Cows were blocked by parity and previous 305-d mature equivalent lactation yields (305-ME; multiparous only). Within each block, cows were randomly allocated to one of two treatment groups. Cows assigned to the rbIL-8 group received 70 μg of rbIL-8 (rbIL-8; n=20) intravenously via the tail vein/artery using a 5 mL syringe attached to a 20-gauge 1-inch long hypodermic needle. Cows assigned to the control group (CTR, n=19) received 5 mL of saline solution via the same route. Body condition was scored at enrollment (Edmonson et al., 1989). Milk yield was recorded at every milking using on-farm milk meters and weekly averages obtained during the first 15 weeks postpartum were used for statistical analyses.

Analyses of IL-8, Metabolites, and Insulin in Serum (Study 1)

Concentrations of IL-8 in serum was determined using a human IL-8 ELISA kit (R&D Systems Inc., Minneapolis, Minn.), validated for bovine serum (Shuster et al., 1996). Insulin concentrations were determined using a commercial ELISA kit for bovine insulin (Bovine Insulin ELISA, ALPCO, Salem, N.H.). Plasma concentrations of non-esterified fatty acids (NEFA; NEFA-C® kit; Wako Pure Chemical Industries, Richmond, Va.) and β-hydroxybutyrate (BHB; (Williamson and Mellanby, 1974), Sigma-Aldrich, St. Louis, Mo.) were determined by colorimetric methods. Haptoglobin concentrations were determined using a colorimetric procedure as previously described (Bicalho et al., 2014), and reported as optical density readings at 450 nm of wavelength.

Disease Definitions

Retained fetal membranes assessed by trained farm personnel was defined as failure to deliver fetal membranes by 24 h after calving. Diagnosis of metritis and endometritis were performed by research personnel based on evaluation of vaginal mucus retrieved using a Metricheck device (Metricheck, SimcroTech, Hamilton, New Zealand). Vaginal discharge was scored using a modified 0 to 5 scale (0=no secretion material retrieved; 1=clear mucus; 2=clear mucus with flecks of pus; 3=mucopurulent discharge containing <50% of pus; 4=mucopurulent discharge containing≥50% of pus; 5=watery, red-brown, fetid vaginal discharge). Cows with a score=5 were considered to have clinical metritis. Puerperal metritis was defined as cows having clinical metritis with a RT>39.5° C. Cows with a score≥3 were considered to have clinical endometritis. Metritis diagnosis was performed at 3, 6 and 9 DIM. Clinical endometritis was evaluated at 35 DIM. Hyperketonemia was defined as cows with serum BHB concentrations≥1.2 mmol/L.

Statistical Analysis

Descriptive statistical analyses were performed using JMP PRO version 12 (SAS Institute Inc., Cary, N.C.) using the ANOVA function for continuous data and chi-square and Fisher's tests for categorical data. Body condition score loss was assessed using the GLIMMIX procedure of SAS. Continuous data collected over time were analyzed using general linear mixed models with the MIXED procedure of SAS version 9.4 (SAS/STAT, SAS Institute Inc., Cary, N.C.). Normality and homoscedasticity of residuals were assessed using residual plots. Initial statistical models included the fixed effects of treatment, parity, dystocia, stillbirth, BCS at calving, days of gestation at calving, RT at calving, sire predicted transmitting ability for milk yield, age in days at calving, time, and the two-way interaction terms between independent variables. Several covariance structures were tested, and the Akaike information criterion (AIC) was used to select the best model fit. Variables and their respective interaction terms were retained in the model when P≤0.15. Significances were considered when P≤0.05 or a trend if 0.05<P≤0.10. For all models, Tukey's honest significance test for multiple comparisons was used. Data are reported as least squares mean (LSM)±standard error of the mean (SEM) unless otherwise stated.

Categorical variables were analyzed by logistic regression models using the binary distribution of the GLIMMIX procedure of SAS. Initial models included the fixed effects of treatment, parity, dystocia, stillbirth, BCS at enrollment, RT at enrollment, and the interaction term treatment by parity. Variables and their respective interaction terms were retained in the model when P≤0.15. Dunnett's significance test for multiple comparisons was used. To evaluate the effect of all rbIL-8 treatments combined against the CTR group on the incidence of hyperketonemia, a contrast was performed. Finally, the effect of treatment on reproduction was analyzed by Cox's proportional hazard using the PHREG procedure in SAS. Control groups were used as reference for comparison. Treatment, parity, twin, stillbirth, dystocia, BCS at enrollment, and the interaction treatment by parity were offered to the model as independent variables, and retained when P≤0.15.

The following results were obtained using the foregoing materials and methods.

Descriptive Data

Descriptive statistics regarding the number of multiparous and primiparous animals enrolled, BCS at enrollment, RT at enrollment, days carried calf, and the incidence of twins, dystocia, stillbirth, and male calf for studies 1, 2, and 3 are depicted in Table 1.

Incidence of Uterine Diseases and Hyperketonemia (Study 1)

Treatment did not affect the incidence of RFM (CTR=4.5; L-IL8=2.5; H-IL8=4.6%; P=0.78). Similarly, treatment did not affect the incidence of metritis, puerperal metritis, and endometritis (Table 2) nor did it affect RT during the first 9 d postpartum (FIG. 4). Intrauterine infusion of the low dose of rbIL-8 reduced (P=0.04) the incidence of hyperketonemia compared with controls (Table 3). Additionally, a contrast used to assess the overall effect of therapy (L-IL8 and H-IL8 vs. CTR) on the incidence of hyperketonemia, indicated that rbIL-8 treatment significantly decreased (P=0.02) the incidence of hyperketonemia when compared with CTR cows (Table 3).

Concentration of IL-8, NEFA, BHB, and Haptoglobin (Study 1)

Serum levels of IL8 was significantly increased (P=0.04) for H-IL8 cows when compared to CTR cows (FIG. 5). However, we detected that both L-IL8 and H-IL8 groups had higher (P<0.05) IL-8 serum concentration at d 3 compared with CTR group (FIG. 5).

A treatment by parity interaction was observed for NEFA serum concentrations (P<0.001). Multiple comparison tests depicted that primiparous cows treated with H-IL8 had lower (P=0.008) concentrations of NEFA in serum compared with CTR (FIG. 6A). Conversely, multiparous cows treated with H-IL8 had higher (P=0.01) serum NEFA concentrations than CTR cows (FIG. 6A). We also observed that multiparous cows treated with rbIL-8 had higher (P≤0.05) NEFA levels at d 1 than CTR multiparous cows. Serum concentrations of BHB did not differ (P=0.18) among treatment groups (FIG. 6C). Finally, haptoglobin concentrations were not different (P=0.96) among treatment groups (FIG. 6D).

Body Condition Score and Reproductive Performance

Study 1.

Body condition score loss from calving until 35 d after parturition was not affected (P=0.30) by treatment (FIG. 7A). Additionally, treatment did not alter (P=0.95) the hazard of pregnancy during the first 280 DIM (adjusted hazard ratio: L-IL8=0.91, 95% CI: 0.57 to 1.47; H-IL8=0.98, 95% CI: 0.59 to 1.63).

Study 2.

No differences were observed (P=0.95) on body condition score loss from calving until 35 d after parturition among treatment groups (FIG. 7B).

Lactation Performance

Study 1.

The effects of treatment on milk, FCM, and ECM yields during the first 6 months after calving are presented on Table 4 and FIG. 5-A. Treated cows produced approximately 3.26 kg/d more milk compared with controls (Table 4). Moreover, FCM was higher (P=0.004) for cows that received rbIL-8 compared with CTR cows. Relative to CTR, rbIL-8 cows produced approximately 2.68 kg/d more FCM (P=0.004; Table 4). We observed that cows treated with rbIL-8 produced approximately 3.04 kg/d more ECM compared with CTR cows (P=0.001; Table 4).

Study 2.

The effect of treatment on milk, FCM, and ECM yields during the first 6 months after calving are presented in Table 4 and FIG. 8B. As observed in study 1, treatment increased milk, FCM, and ECM yields (P<0.001). We observed that L-IL8, M-IL8, and H-IL8 cows produced 1.17, 2.18, and 2.39 kg/d more milk when compared with controls, respectively (Table 4). Cows in the L-IL8, M-IL8, and H-IL8 groups produced 2.18, 2.96, and 3.40 kg/d more FCM than CTR cows, respectively (Table 4). Moreover, cows in the L-IL8, M-IL8, and H-IL8 groups produced 1.77, 2.78, and 3.24 kg/d more ECM when compared with the CTR group, respectively (Table 4).

Study 3.

Treatment was again associated with a significant increase in milk yield (P=0.04, FIG. 9). Treated cows produced 4 kg/d more milk (rbIL-8=42.7±1.4; CTR=38.7±1.4) when compared with CTR cows (FIG. 9).

It will be apparent from the foregoing results that this Part II demonstrates in three independent studies that rbIL-8 administration in the immediate postpartum, using both intrauterine and intravenous administration, was associated with a significant increase in milk production. In addition, the administration of rbIL-8 reduced the incidence of hyperketonemia.

Although in study 1 of this Part II a direct effect on milk yield was not anticipated, cows treated with intrauterine rbIL-8 at calving produced approximately 3.26, 2.68, and 3.04 kg/d more milk, FCM, and ECM yields, respectively, compared with CTR cows during the first 6 months after parturition. The observed effect of rbIL-8 on milk yield in study 1 was replicated in study 2; where rbIL-8 cows produced significantly more milk, FCM, and ECM yields when compared with CTR cows. Additionally, when cows were treated with a single intravenous administration of rbIL-8 shortly after calving, we observed that they produced 4 kg/d more milk than CTR cows during the first 15 weeks after parturition. Surprisingly, the observed positive effect on milk yield was not associated with increased BCS loss. Considering the observed results in the current study of rbIL-8 on hyperketonemia combined with the above-mentioned previously reported effects of IL-8 on hepatocytes, without intending to be bound by any particular theory, it is considered that by improving liver function in early lactation, rbIL-8 might stimulate appetite and increase feed intake, and therefore it would not affect significantly BCS. It is also known that high-producing cows utilize more nutrients for milk synthesis compared with low-producing cows. As a result, feed intake increases to support the demands imposed for milk production (Baumgard et al., 2017).

Recent studies have shown that the use of a nonsteroidal anti-inflammatory drug (NSAID) increased whole-lactation milk yield (Farney et al., 2013a, Farney et al., 2013b, Carpenter et al., 2015). However, in those studies, several pro-inflammatory markers, such as thromboxane B2, 13-hydroxyoctadecadienoic acid, 9-hydroxyoctadecadienoic acid, and pro-inflammatory eicosanoids, increased after the cows received the anti-inflammatory agent. Therefore, it is not clear if the observed effect on milk yield was due to cows entering an anti-inflammatory state or due to a rebound effect that triggered an inflammatory response after the anti-inflammatory therapy. Nevertheless, a recent study has demonstrated that the administration of sodium salicylate during the early postpartum was not associated with milk production (Carpenter et al., 2018). In addition, other studies have evaluated the effect of flunixin meglumine and meloxicam on milk production of Holstein cows reporting neutral or negative effects (Newby et al., 2013, Newby et al., 2017).

Taken together, considering the effects of rbIL-8 treatment that we observed on circulating metabolites, hyperketonemia, and on milk production, and the evidence that rbIL-8 induces insulin resistance, promotes angiogenesis, reduces apoptosis and stimulates cell proliferation, without intending to be constrained by any particular theory, it is considered that a single administration of rbIL-8 at the day of calving increases insulin resistance in peripheral tissues, increases mammary cell proliferation, and enhances hepatic function during lactation; thus, improving metabolic health and milk yield in Holstein cows. Interpretation of data for prevention of uterine disease by IL-8 administration is complicated by not being able to compare data for administration before parturition or closer to 12 hours after calving.

Tables

TABLE 1

Descriptive data for cows enrolled in studies 1, 2, and 3. One-way ANOVA and chi-square analysis were used for comparing continuous and categorical data, respectively.

| Item | Study 1 | | | | Study 2 | | | | | Study 3 | | |
| --- | --- | --- | --- | --- | --- | --- | --- | --- | --- | --- | --- | --- |
| | L-IL8 | H-IL8 | CTR | P-value[1] | L-IL8 | M-IL8 | H-LI8 | CTR | P-value[1] | rbIL-8 | CTR | P-value[1] |
| Average Parity | 1.49 | 1.53 | 1.52 | 0.34 | — | — | — | — | — | 1.50 | 1.50 | 1.00 |
| No. of primiparous, n | 41 | 31 | 32 | — | 41 | 41 | 41 | 41 | — | 10 | 10 | — |
| No. of multiparous, n | 39 | 35 | 35 | — | — | — | — | — | — | 10 | 9 | — |

TABLE 1-continued

Descriptive data for cows enrolled in studies 1, 2, and 3. One-way ANOVA and chi-square analysis were used for comparing continuous and categorical data, respectively.

| Item | Study 1 | | | | Study 2 | | | | | Study 3 | | |
|---|---|---|---|---|---|---|---|---|---|---|---|---|
| | L-IL8 | H-IL8 | CTR | P-value[1] | L-IL8 | M-IL8 | H-LI8 | CTR | P-value[1] | rbIL-8 | CTR | P-value[1] |
| Total enrolled animals, n | 80 | 66 | 67 | — | 41 | 41 | 41 | 41 | — | 20 | 19 | — |
| Average BCS[2] at enrollment | 3.41 | 3.40 | 3.36 | 0.42 | 3.59 | 3.59 | 3.67 | 3.62 | 0.60 | 3.46 | 3.39 | 0.33 |
| Average RT[1] at enrollment, °C. | 38.8 | 38.8 | 38.7 | 0.60 | 38.9 | 38.9 | 38.9 | 39.0 | 0.52 | — | — | — |
| Average days carried calf, d | 277.4 | 275.2 | 274.9 | 0.17 | 278.0 | 277.6 | 280.0 | 277.4 | 0.13 | 277.7 | 279.4 | 0.28 |
| Twins, % | 0.00 | 3.00 | 5.00 | 0.08 | 0.00 | 2.44 | 0.00 | 0.00 | 0.98 | 5.00 | 5.26 | 1.00 |
| Dystocia, % | 3.75 | 1.50 | 3.00 | 0.87 | 4.88 | 9.76 | 4.88 | 4.88 | 0.84 | 0.00 | 5.26 | 0.48 |
| Stillbirth, % | 6.25 | 3.03 | 4.48 | 0.66 | 4.88 | 12.2 | 7.32 | 4.88 | 0.68 | 5.00 | 15.8 | 0.34 |
| Male calf, % | 46.0 | 38.0 | 34.0 | 0.31 | 36.6 | 34.1 | 46.3 | 34.1 | 0.62 | 35.9 | 42.1 | 0.43 |

Study 1: CTR = 250 mL of saline solution; L-IL8 = 11.25 μg of rbIL-8 diluted in 250 mL of saline solution; H-IL8 = 1,125 μg of rbIL-8 diluted in 250 mL of saline solution.
Study 2: CTR = 250 mL of saline solution; L-IL8 = 0.14 μg of rbIL-8 diluted in 250 mL of saline solution; M-IL8 = 14 μg of rbIL-8 diluted in 250 mL of saline solution; H-IL8 = 1,400 μg of rbIL-8 diluted in 250 mL of saline solution.
Study 3: CTR = 5 mL of saline solution; rbIL-8 = 70 μg of rbIL-8 diluted in 5 mL of saline solution.
[1]For the chi-square test, we followed the assumption that no cell should have an expected frequency of less than 5; when the assumption was not satisfied, Fisher's exact test was used.
[2]BCS = Body condition score.
[3]RT = Rectal temperature.

TABLE 2

Effects of different rbIL-8 doses on the incidence of clinical metritis, puerperal metritis, and endometritis based on vaginal discharge score in cows from study 1.

| Group | % Incidence | Odds ratio (95% CI) | P-value[1] Trt |
|---|---|---|---|
| | Clinical metritis | | |
| CTR | 21.54 | Reference | |
| L-IL8 | 27.03 | 1.64 (0.70-3.84) | 0.21 |
| H-IL8 | 15.87 | 0.75 (0.29-1.26) | |
| | Puerperal metritis | | |
| CTR | 4.62 | Reference | |
| L-IL8 | 8.11 | 1.80 (0.43-7.62) | 0.71 |
| H-IL8 | 6.35 | 1.40 (0.30-6.59) | |
| | Endometritis | | |
| CTR | 15.25 | Reference | |
| L-IL8 | 12.68 | 1.06 (0.36-3.10) | 0.97 |
| H-IL8 | 12.28 | 0.95 (0.31-2.93) | |

[1]Study 1: CTR = 250 mL of saline solution, n = 67; L-IL8 = 11.25 μg of rbIL-8 diluted in 250 mL of saline solution, n = 80; H-IL8 = 1,125 μg of rbIL-8 diluted in 250 mL of saline solution, n = 66.
[1]Trt, treatment.

TABLE 3

Effects of different rbIL-8 doses on the incidence of hyperketonemia in cows from study 1.

| | % Incidence | | P-value[1] | | |
|---|---|---|---|---|---|
| Group | Hyperketonemia | Odds ratio (95% CI) | Trt | D | C |
| CTR | 35.29 | Reference | — | | |
| L-IL8 | 15.79 | 0.37 (0.16-0.85) | 0.05 | 0.04 | 0.02 |
| H-IL8 | 22.22 | 0.51 (0.23-1.11) | | 0.16 | |

Study 1: CTR = 250 mL of saline solution, n = 67; L-IL8 = 11.25 μg of rbIL-8 diluted in 250 mL of saline solution, n = 80; H-IL8 = 1,125 μg of rbIL-8 diluted in 250 mL of saline solution, n = 66.

[1]Trt, treatment; C = contrast between CTR and all rbIL-8 doses combined; D = different rbIL-8 treatment groups were tested against the control group using Dunnett's procedure.

TABLE 4

Effect of different rbIL-8 doses on production parameters of cows from studies 1 and 2 during the first six months after calving.

| Study | TDM (LSM ± SEM) | P-value[1] | 3.5% FCM (LSM ± SEM) | P-value[1] | ECM (LSM ± SEM) | P-value[1] |
|---|---|---|---|---|---|---|
| | | | Kg/d | | | |
| Study 1 | | | | | | |
| CTR | 31.5 ± 1.2 | <0.001 | 35.0 ± 1.2 | 0.004 | 33.5 ± 1.2 | 0.001 |
| L-IL8 | 34.8 ± 1.3 | | 37.6 ± 1.6 | | 36.4 ± 1.3 | |
| H-IL8 | 34.8 ± 1.3 | | 37.7 ± 1.6 | | 36.6 ± 1.3 | |
| Study 2 | | | | | | |
| CTR | 31.7 ± 1.8 | <0.001 | 32.5 ± 1.9 | <0.001 | 32.6 ± 1.9 | <0.001 |
| L-IL8 | 32.9 ± 1.8 | | 34.7 ± 1.9 | | 34.4 ± 1.9 | |

TABLE 4-continued

Effect of different rbIL-8 doses on production parameters of cows from studies 1 and 2 during the first six months after calving.

| Study | TDM (LSM ± SEM) | P-value[1] | 3.5% FCM (LSM ± SEM) Kg/d | P-value[1] | ECM (LSM ± SEM) | P-value[1] |
|---|---|---|---|---|---|---|
| M-IL8 | 33.9 ± 1.7 | | 35.5 ± 1.8 | | 35.4 ± 1.8 | |
| H-IL8 | 34.1 ± 1.7 | | 35.9 ± 1.8 | | 35.9 ± 1.8 | |

Study 1: CTR = 250 mL of saline solution, n = 67; L-IL8 = 11.25 μg of rbIL-8 diluted in 250 mL of saline solution, n = 80; H-IL8 = 1,125 μg of rbIL-8 diluted in 250 mL of saline solution, n = 66.
Study 2: CTR = 250 mL of saline solution, n = 41; L-IL8 = 0.14 μg of rbIL-8 diluted in 250 mL of saline solution, n = 41; M-IL8 = 14 μg of rbIL-8 diluted in 250 mL of saline solution, n = 41; H-IL8 = 1,400 μg of rbIL-8 diluted in 250 mL of saline solution, n = 41.
[1]P-values indicate overall treatment effects.
TDM = Test day milk.
FCM = Fat corrected milk.
ECM = Energy corrected milk.

References for Part II

REFERENCES

Bauman, D. E. and R. G. Vernon. 1993. Effects of exogenous bovine somatotropin on lactation. Annu Rev Nutr 13:437-461.

Baumgard, L. H., R. J. Collier, and D. E. Bauman. 2017. A 100-Year Review: Regulation of nutrient partitioning to support lactation. J Dairy Sci 100(12):10353-10366.

Bell, A. W. and D. E. Bauman. 1997. Adaptations of glucose metabolism during pregnancy and lactation. J Mammary Gland Biol Neoplasia 2(3):265-278.

Bendre, M. S., D. C. Montague, T. Peery, N. S. Akel, D. Gaddy, and L. J. Suva. 2003. Interleukin-8 stimulation of osteoclastogenesis and bone resorption is a mechanism for the increased osteolysis of metastatic bone disease. Bone 33(1):28-37.

Bicalho, M. L., F. S. Lima, E. K. Ganda, C. Foditsch, E. B. Meira, Jr., V. S. Machado, A. G. Teixeira, G. Oikonomou, R. O. Gilbert, and R. C. Bicalho. 2014. Effect of trace mineral supplementation on selected minerals, energy metabolites, oxidative stress, and immune parameters and its association with uterine diseases in dairy cattle. J Dairy Sci 97(7):4281-4295.

Bicalho, M. L. S., V. S. Machado, G. Oikonomou, R. O. Gilbert, and R. C. Bicalho. 2012. Association between virulence factors of *Escherichia coli, Fusobacterium necrophorum*, and *Arcanobacterium pyogenes* and uterine diseases of dairy cows. Veterinary Microbiology 157(1-2):125-131.

Brantley, D. M., C. L. Chen, R. S. Muraoka, P. B. Bushdid, J. L. Bradberry, F. Kittrell, D. Medina, L. M. Matrisian, L. D. Kerr, and F. E. Yull. 2001. Nuclear factor-kappaB (NF-kappaB) regulates proliferation and branching in mouse mammary epithelium. Mol Biol Cell 12(5):1445-1455.

Cao, Y., G. Bonizzi, T. N. Seagroves, F. R. Greten, R. Johnson, E. V. Schmidt, and M. Karin. 2001. IKKalpha provides an essential link between RANK signaling and cyclin D1 expression during mammary gland development. Cell 107(6):763-775.

Carpenter, A. J., C. M. Ylioja, L. K. Mamedova, K. E. Olagaray, and B. J. Bradford. 2018. Effects of early postpartum sodium salicylate treatment on long-term milk, intake, and blood parameters of dairy cows. J Dairy Sci 101(2):1437-1447.

Carpenter, A. J., C. M. Ylioja, C. F. Vargas, L. K. Mamedova, L. G. Mendonca, J. F. Coetzee, L. C. Hollis, R. Gehring, and B. J. Bradford. 2015. Hot topic: Early postpartum treatment of commercial dairy cows with nonsteroidal antiinflammatory drugs increases whole-lactation milk yield. J Dairy Sci.

Chang, L., S. H. Chiang, and A. R. Saltiel. 2004. Insulin signaling and the regulation of glucose transport. Mol Med 10(7-12):65-71.

Colletti, L. M., M. Green, M. D. Burdick, S. L. Kunkel, and R. M. Strieter. 1998. Proliferative effects of CXC chemokines in rat hepatocytes in vitro and in vivo. Shock 10(4):248-257.

De Koster, J. D. and G. Opsomer. 2013. Insulin Resistance in Dairy Cows. Vet Clin N Am-Food A 29(2):299-+.

Drackley, J. K. 1999. ADSA Foundation Scholar Award. Biology of dairy cows during the transition period: the final frontier? J Dairy Sci 82(11):2259-2273.

Drackley, J. K., S. S. Donkin, and C. K. Reynolds. 2006. Major advances in fundamental dairy cattle nutrition. J Dairy Sci 89(4):1324-1336.

Dubuc, J., T. F. Duffield, K. E. Leslie, J. S. Walton, and S. J. LeBlanc. 2010. Risk factors for postpartum uterine diseases in dairy cows. J Dairy Sci 93(12):5764-5771.

Duffield, T. F., K. D. Lissemore, B. W. McBride, and K. E. Leslie. 2009. Impact of hyperketonemia in early lactation dairy cows on health and production. J Dairy Sci 92(2):571-580.

Edmonson, A. J., I. J. Lean, L. D. Weaver, T. Farver, and G. Webster. 1989. A Body Condition Scoring Chart for Holstein Dairy-Cows. Journal of Dairy Science 72(1):68-78.

Farney, J. K., L. K. Mamedova, J. F. Coetzee, B. KuKanich, L. M. Sordillo, S. K. Stoakes, J. E. Minton, L. C. Hollis, and B. J. Bradford. 2013a. Anti-inflammatory salicylate treatment alters the metabolic adaptations to lactation in dairy cattle. Am J Physiol-Reg I 305(2):R110-R117.

Farney, J. K., L. K. Mamedova, J. F. Coetzee, J. E. Minton, L. C. Hollis, and B. J. Bradford. 2013b. Sodium salicylate treatment in early lactation increases whole-lactation milk and milk fat yield in mature dairy cows. Journal of Dairy Science 96(12):7709-7718.

Franchini, M., E. Monnais, D. Seboek, T. Radimerski, E. Zini, K. Kaufmann, T. Lutz, C. Reusch, M. Ackermann, B. Muller, and P. Linscheid. 2010. Insulin resistance and increased lipolysis in bone marrow derived adipocytes stimulated with agonists of Toll-like receptors. Horm Metab Res 42(10):703-709.

Fricke, P. M., D. Z. Caraviello, K. A. Weigel, and M. L. Welle. 2003. Fertility of dairy cows after resynchronization of ovulation at three intervals following first timed insemination. Journal of Dairy Science 86(12):3941-3950.

Fujishiro, M., Y. Gotoh, H. Katagiri, H. Sakoda, T. Ogihara, M. Anai, Y. Onishi, H. Ono, M. Abe, N. Shojima, Y. Fukushima, M. Kikuchi, Y. Oka, and T. Asano. 2003. Three mitogen-activated protein kinases inhibit insulin signaling by different mechanisms in 3T3-L1 adipocytes. Mol Endocrinol 17(3):487-497.

Galvao, K. N., M. J. B. F. Flaminio, S. B. Brittin, R. Sper, M. Fraga, L. Caixeta, A. Ricci, C. L. Guard, W. R. Butler, and R. O. Gilbert. 2010. Association between uterine disease and indicators of neutrophil and systemic energy status in lactating Holstein cows. Journal of Dairy Science 93(7):2926-2937.

Gilbert, R. O., S. T. Shin, C. L. Guard, H. N. Erb, and M. Frajblat. 2005. Prevalence of endometritis and its effects on reproductive performance of dairy cows. Theriogenology 64(9):1879-1888.

Goff, J. P. and R. L. Horst. 1997. Physiological changes at parturition and their relationship to metabolic disorders. Journal of Dairy Science 80(7):1260-1268.

Greenfield, R. B., M. J. Cecava, and S. S. Donkin. 2000. Changes in mRNA expression for gluconeogenic enzymes in liver of dairy cattle during the transition to lactation. J Dairy Sci 83(6):1228-1236.

Hammon, D. S., I. M. Evjen, T. R. Dhiman, J. P. Goff, and J. L. Walters. 2006. Neutrophil function and energy status in Holstein cows with uterine health disorders. Vet Immunol Immunopathol 113(1-2):21-29.

Han, I. K. and I. H. Kim. 2005. Risk factors for retained placenta and the effect of retained placenta on the occurrence of postpartum diseases and subsequent reproductive performance in dairy cows. J Vet Sci 6(1):53-59.

Hardy, O. T., R. A. Perugini, S. M. Nicoloro, K. Gallagher-Dorval, V. Puri, J. Straubhaar, and M. P. Czech. 2011. Body mass index-independent inflammation in omental adipose tissue associated with insulin resistance in morbid obesity. Surg Obes Relat Dis 7(1):60-67.

Hogaboam, C. M., C. L. Bone-Larson, M. L. Steinhauser, N. W. Lukacs, L. M. Colletti, K. J. Simpson, R. M. Strieter, and S. L. Kunkel. 1999. Novel CXCR2-dependent liver regenerative qualities of ELR-containing CXC chemokines. FASEB J 13(12):1565-1574.

Holmes, W. E., J. Lee, W. J. Kuang, G. C. Rice, and W. I. Wood. 1991. Structure and functional expression of a human interleukin-8 receptor. Science 253(5025):1278-1280.

Hou, Y., C. H. Ryu, J. A. Jun, S. M. Kim, C. H. Jeong, and S. S. Jeun. 2014. IL-8 enhances the angiogenic potential of human bone marrow mesenchymal stem cells by increasing vascular endothelial growth factor. Cell Biol Int 38(9):1050-1059.

Hussain, A. M. 1989. Bovine Uterine Defense-Mechanisms—a Review. J Vet Med B 36(9):641-651.

Kanayama, N., T. Terao, and K. Horiuchi. 1988. The role of human neutrophil elastase in the premature rupture of membranes. Asia Oceania J Obstet Gynaecol 14(3):389-397.

Kehrli, M. E. and J. P. Goff. 1989. Periparturient Hypocalcemia in Cows—Effects on Peripheral-Blood Neutrophil and Lymphocyte Function. Journal of Dairy Science 72(5):1188-1196.

Kimura, K., J. P. Goff, M. E. Kehrli, and T. A. Reinhardt. 2002. Decreased neutrophil function as a cause of retained placenta in dairy cattle. Journal of Dairy Science 85(3):544-550.

Kobashi, C., S. Asamizu, M. Ishiki, M. Iwata, I. Usui, K. Yamazaki, K. Tobe, M. Kobayashi, and M. Urakaze. 2009. Inhibitory effect of IL-8 on insulin action in human adipocytes via MAP kinase pathway. J Inflamm (Lond) 6:25.

Kohn, A. D., S. A. Summers, M. J. Birnbaum, and R. A. Roth. 1996. Expression of a constitutively active Akt Ser/Thr kinase in 3T3-L1 adipocytes stimulates glucose uptake and glucose transporter 4 translocation. J Biol Chem 271(49):31372-31378.

Martin, D., R. Galisteo, and J. S. Gutkind. 2009. CXCL8/IL8 stimulates vascular endothelial growth factor (VEGF) expression and the autocrine activation of VEGFR2 in endothelial cells by activating NFkappaB through the CBM (Carma3/Bcl10/Malt1) complex. J Biol Chem 284(10):6038-6042.

Mathews, A. T., J. E. Rico, N. T. Sprenkle, A. L. Lock, and J. W. McFadden. 2016. Increasing palmitic acid intake enhances milk production and prevents glucose-stimulated fatty acid disappearance without modifying systemic glucose tolerance in mid-lactation dairy cows. J Dairy Sci 99(11):8802-8816.

McArt, J. A., D. V. Nydam, and G. R. Oetzel. 2012. Epidemiology of subclinical ketosis in early lactation dairy cattle. J Dairy Sci 95(9):5056-5066.

McNamara, J. P. and J. K. Hillers. 1986. Adaptations in lipid metabolism of bovine adipose tissue in lactogenesis and lactation. J Lipid Res 27(2):150-157.

Mitchell, G. B., B. N. Albright, and J. L. Caswell. 2003. Effect of interleukin-8 and granulocyte colony-stimulating factor on priming and activation of bovine neutrophils. Infection and Immunity 71(4):1643-1649.

Moreira, F., C. Orlandi, C. A. Risco, R. Mattos, F. Lopes, and W. W. Thatcher. 2001. Effects of presynchronization and bovine somatotropin on pregnancy rates to a timed artificial insemination protocol in lactating dairy cows. J Dairy Sci 84(7):1646-1659.

Newby, N. C., K. E. Leslie, H. D. P. Dingwell, D. F. Kelton, D. M. Weary, L. Neuder, S. T. Millman, and T. F. Duffield. 2017. The effects of periparturient administration of flunixin meglumine on the health and production of dairy cattle. Journal of Dairy Science 100(1):582-587.

Newby, N. C., D. L. Pearl, S. J. LeBlanc, K. E. Leslie, M. A. G. von Keyserlingk, and T. F. Duffield. 2013. Effects of meloxicam on milk production, behavior, and feed intake in dairy cows following assisted calving. Journal of Dairy Science 96(6):3682-3688.

Onuffer, J. J. and R. Horuk. 2002. Chemokines, chemokine receptors and small-molecule antagonists: recent developments. Trends Pharmacol Sci 23(10):459-467.

Osawa, Y., M. Nagaki, Y. Banno, D. A. Brenner, T. Asano, Y. Nozawa, H. Moriwaki, and S. Nakashima. 2002. Tumor Necrosis Factor Alpha-Induced Interleukin-8 Production via NF—B and Phosphatidylinositol 3-Kinase/Akt Pathways Inhibits Cell Apoptosis in Human Hepatocytes. Infection and Immunity 70(11):6294-6301.

Overton, M. and J. Fetrow. 2008. Economics of postpartum uterine health. Proc. Dairy Cattle Reprod. Council Conv. Omaha, Nebr. Dairy Cattle Reproductive Council, Hartland, Wis. (2008), pp. 39-43.

Pursley, J. R., M. O. Mee, and M. C. Wiltbank. 1995. Synchronization of ovulation in dairy cows using PGF2alpha and GnRH. Theriogenology 44(7):915-923.

Rath, W., M. Winkler, and B. Kemp. 1998. The importance of extracellular matrix in the induction of preterm delivery. J Perinat Med 26(6):437-441.

Reynolds, C. K., P. C. Aikman, B. Lupoli, D. J. Humphries, and D. E. Beever. 2003. Splanchnic metabolism of dairy cows during the transition from late gestation through early lactation. Journal of Dairy Science 86(4):1201-1217.

Saremi, B., S. Winand, P. Friedrichs, A. Kinoshita, J. Rehage, S. Danicke, S. Haussler, G. Breves, M. Mielenz, and H. Sauerwein. 2014. Longitudinal profiling of the tissue-specific expression of genes related with insulin sensitivity in dairy cows during lactation focusing on different fat depots. PLoS One 9(1):e86211.

Selim, S., S. Salin, J. Taponen, A. Vanhatalo, T. Kokkonen, and K. T. Elo. 2014. Prepartal dietary energy alters transcriptional adaptations of the liver and subcutaneous adipose tissue of dairy cows during the transition period. Physiol Genomics 46(9):328-337.

Shuster, D. E., E. K. Lee, and M. E. Kehrli. 1996. Bacterial growth, inflammatory cytokine production, and neutrophil recruitment during coliform mastitis in cows within ten days after calving, compared with cows at midlactation. American Journal of Veterinary Research 57(11): 1569-1575.

Srivastava, S., M. Matsuda, Z. Hou, J. P. Bailey, R. Kitazawa, M. P. Herbst, and N. D. Horseman. 2003. Receptor activator of NF-kappaB ligand induction via Jak2 and Stat5a in mammary epithelial cells. J Biol Chem 278(46):46171-46178.

Strieter, R. M., P. J. Polverini, S. L. Kunkel, D. A. Arenberg, M. D. Burdick, J. Kasper, J. Dzuiba, J. Van Damme, A. Walz, D. Marriott, and et al. 1995. The functional role of the ELR motif in CXC chemokine-mediated angiogenesis. J Biol Chem 270(45):27348-27357.

von Soosten, D., U. Meyer, E. M. Weber, J. Rehage, G. Flachowsky, and S. Danicke. 2011. Effect of trans-10, cis-12 conjugated linoleic acid on performance, adipose depot weights, and liver weight in early-lactation dairy cows. J Dairy Sci 94(6):2859-2870.

Williamson, D. H. and j. Mellanby. 1974. D-(-)-3-hydroxybutyrate. In Bergmeyer, H. U. (ed.), Methods of Enzymatic Analysis, Academic Press, New York, pp.: 1836-1839.

Part III

This Part III demonstrates that systemic administration of rbIL-8 induces long-term whole-body insulin resistance in bull calves. The data show the effects of systemic administration of rbIL-8 on glucose clearance and insulin response following a glucose challenge, blood metabolites, immune cell populations, and inflammatory parameters in bull Holstein calves. Glucose tolerance tests were performed 12 h and 7 d after the last rbIL-8 dose. Intravenous administration of rbIL-8 induced long-term insulin resistance, decreased average daily gain, elevated rectal temperature, and increased serum concentrations of haptoglobin, metabolites, and white blood cell counts.

As shown above, we demonstrated that a single intrauterine or intravenous administration rbIL-8 into Holstein dairy cows on the day of parturition is associated with a long-lasting increase in milk production. Intrauterine treatment altered IL-8 plasma levels, indicating that the increase in milk yield was caused by a systemic effect of rbIL-8. Additionally, 24 h after treatment, we noted a sharp increase in the concentration of serum non-esterified fatty acids (NEFA) in cows treated with rbIL-8. It is well documented in the literature that insulin has both anti-lipolytic and lipogenic effects, resulting in reduced NEFA mobilization (Herdt, 2000, De Koster and Opsomer, 2013). Therefore, the increase in NEFA levels that we observed could reflect a state of insulin resistance.

High-producing dairy cows undergo extreme metabolic adaptations during the transition from late gestation to early lactation. Feed consumption increases approximately 2-fold between the week preceding parturition and the first 30 d postpartum but remains insufficient to meet lactational nutrient demands (Bell, 1995, Reynolds et al., 2003). During this period of negative nutrient balance, homeorhetic mechanisms trigger the mobilization of body reserves to support milk synthesis. Transient insulin resistance allows glucose to be spared by peripheral tissues and directed toward the synthesis of lactose in the mammary gland (Bell and Bauman, 1997). Furthermore, the reduced insulin response enhances lipolysis and muscle breakdown (De Koster and Opsomer, 2013). As a result of this catabolic state, high-producing dairy cows can lose 1.5 kg/d of body weight in the first three weeks postpartum when energy balance is −7 to −9 Mcal NEL/d (Bell, 1995, Koltes and Spurlock, 2011). The liver is the major organ responsible for processing nutrients and metabolites during the transition period (Reynolds et al., 2003); thus, manipulating homeorhesis while optimizing hepatic function in the early postpartum period is expected to enhance lactational performance. One clear example of an exogenous treatment that alters homeorhetic controls to increase milk production in lactating dairy cows is recombinant bovine somatotropin (rbST). Treatment with rbST increases milk production through complex, coordinated effects in multiple tissues, for example by increasing hepatic gluconeogenesis, inducing insulin resistance, decreasing glucose oxidation, and modulating the activity and function of the mammary gland (Bell and Bauman, 1997). However, repeated administration of rbST is necessary to sustain its positive effect on milk yield, which requires labor and treatment costs.

There are numerous studies demonstrating a key role of pro-inflammatory cytokines, such as IL-8, IL-6, and TNF-$\alpha$, in mediating insulin resistance (Kushibiki et al., 2000; Kobashi et al., 2009 and Hardy et al., 2011). For instance, Holstein steers treated s.c. once daily for 12 d with rbTNF-$\alpha$ displayed decreased peripheral insulin sensitivity (Kushibiki et al., 2000). A direct effect of IL-8 on the insulin response has only been demonstrated in vitro, where exposure to IL-8 induced insulin resistance in human adipocytes (Kobashi et al., 2009). Insulin resistance is one of the major homeorhetic regulations that occurs in dairy cows to support lactation. Thus, adjusting energy partitioning by altering tissue responses to insulin has the potential to increase milk production.

We tested to determine whether systemic administration of rbIL-8 to bull Holstein calves affects response to a glucose challenge, increases systemic inflammation, and alter white blood cell populations, and explored the effects of rbIL-8 on the insulin response in peripheral tissue, on metabolites, on inflammatory parameters, and on white blood cell counts in bull Holstein calves.

The following materials and methods were used to produce the results described in this Part III.

Ethics Statement

The research protocol was reviewed and approved by the Cornell University Institutional Animal Care and Use Committee (protocol number 2016-0017). The methods were carried out in accordance with the approved guidelines.

Animals, Facilities, and Management

Eighteen Holstein bull calves between 17 and 29 d old and between 39.5 and 73.3 kg of body weight (BW) were purchased from a commercial dairy farm and shipped to the research barn situated in the large animal sector of Cornell University, Ithaca, N.Y. Calves born only by normal calving were included in the study. After calving, calves were fed with 4 L of pooled pasteurized colostrum within 6 h of birth. Each individual pen (concrete walls with stainless steel gate; 2 m²) was bedded with pine shavings and cleaned on a daily basis. Animals were acclimated for 7 d prior to initiation of the study. Calves were fed with 9 L of raw milk, purchased from the Cornell University Teaching Dairy, twice daily (0630 and 1600 h). Additionally, water was available between feedings, and calf starter (Calf starter 18% CP, DuMOR) was offered ad libitum.

Experimental Design and Sample Collection

The day of enrollment was considered as d 1 and the study duration was 10 d. Calves were randomly allocated to one of two treatment groups: rbIL-8 (rbIL-8, n=10) or control (CTR, n=8). Originally the study was designed to administer the treatments s.c. However, following the first treatment, a large local inflammatory reaction was observed, so the route of administration was changed to i.v. Therefore, calves assigned to the rbIL-8 group received 1 s.c. injection (d 1, 0900 h) and 6 i.v. injections (d 1 at 1600 h; d 2 and d 3 at 0900 and 1600 h; and d 4 at 0900 h) of rbIL-8 (4 μg/kg BW). Calves assigned to the CTR group received 2 mL of sterile saline solution (VEDCO Inc., Saint Joseph, Mo.) according to the above schedule. Recombinant bovine IL-8 was produced and purified as described herein. Long-term 16 Ga catheters (MILA INTERNATIONAL INC., Florence, Ky.) were inserted into the left jugular vein 1 d before the first treatment for collection of blood during the study period and for administration of glucose. The catheters were maintained by flushing with heparinized saline solution. Blood samples were collected on d 1, 2, 3 and 4 prior to treatment; at 30 min prior to treatment (0830 h); at 30, 60, 120, 240 and 360 min after treatment; and daily at 0830 h for the rest of the study period via jugular vein catheter into vacutainer K2-EDTA Blood Collection Tubes (BD Vacutainer®, Franking Lakes, N.J.) and immediately placed on ice. Within 1 h after blood collection, samples were used for hemogram determination using a Vet hemogram instrument (Heska-Hemature™, Loveland, Colo.), and plasma was obtained by centrifugation (2,000×g for 15 min at 4° C.) and aliquoted into 2-mL eppendorf tubes and stored at −80° C. until analysis. Additionally, rectal temperature (RT) was recorded daily and after treatment at the same time as the blood sample collections, as described above. Measurements of BW were taken at birth, and on d 0, 1, 3, 5, 7 and 10 of the study, at 1400-1500 h. Consumption of calf starter and milk was recorded daily throughout the study period.

Evaluation of the Peripheral Response to Insulin and Glucose Disappearance

The peripheral response to insulin and glucose disappearance was evaluated using intravenous glucose tolerance test (IVGTT) in all calves enrolled in the study. The tests were performed 7 h after the last treatment (d 4, 1600 h) and on d 10 (0800 h) of the study. Calves were fasted for 10 h prior to each test. Calves were infused with 0.25 g/kg of BW of glucose (dextrose 50%, wt/vol; Phoenix Scientific Inc., St. Joseph, Mo.) followed by 5 mL of sterile saline solution to flush the catheter. Blood was sampled at −15, 0, 15, 30, 45, 60, 90 and 120 min relative to glucose infusion. Catheters were flushed between sampling points with sterile saline solution containing sodium heparin to avoid clotting. The initial 3 mL of blood drawn from the catheter at every sampling point was discarded before the sample was collected to avoid dilution. Blood was collected into vacutainer K2-EDTA Blood Collection Tubes (BD Vacutainer®, Franking Lakes, N.J.). Samples were placed on ice immediately and centrifuged at 2,000×g for 15 min at 4° C. within 1 h of collection. Plasma was harvested and stored at −80° C. until assayed.

Insulin and Metabolite Assays

Plasma concentrations of NEFA (NEFA-C® kit; Wako Pure Chemical Industries, Richmond, Va.), β-hydroxybutyrate (BHB) ((Williamson and Mellanby, 1974); Sigma-Aldrich, St. Louis, Mo.), plasma urea nitrogen (PUN) (Sigma-Aldrich, St. Louis, Mo.), and glucose (Sigma-Aldrich, St. Louis, Mo.) were determined by colorimetric methods. Insulin concentration was determined using a commercial ELISA kit for bovine insulin (Bovine Insulin ELISA, ALPCO, Salem, N.H.). Haptoglobin concentration was determined using a colorimetric procedure as previously described (Bicalho et al., 2014). Results of haptoglobin concentrations were reported as optical density readings at 450 nm of wavelength.

Statistical Methods

All statistical analyses were performed using SAS (version 9.4; SAS/STAT, SAS Institute Inc., Cary, N.C.). The effects of rbIL-8 on dry matter intake (DMI) of starter, milk consumption, average daily gain (ADG), feed efficiency, blood cell parameters, RT, and plasma concentration of haptoglobin, metabolites and insulin, were analyzed using mixed general linear mixed models with the MIXED procedure of SAS version 9.4 (SAS/STAT, SAS Institute Inc., Cary, N.C.). Normality and homoscedasticity of residuals were assessed using residual plots. Fixed effects of treatment, time, BW at d 0, age at d 0, and the two-way interaction treatment by time were offered to the model as independent variables and calf was considered a random effect. For data collected over time, data points were correlated within each research subject. Manual backward stepwise elimination of variables was undertaken when $P>0.10$. The baseline values for each of the variables were included in the model as covariates. Several covariance structures were tested, and that with the lowest Akaike information criterion (AIC) was selected. One-way ANOVA was used to compare the mean of the following variables: birth weight, BW at d 0, age at d 0, final weight, total milk intake (MI), and total starter intake. Plasma concentrations of glucose and insulin from IVGTT were used to create response curves. The positive incremental area under the curve (AUC) of glucose and insulin was calculated in SAS, correcting for baseline based on the trapezoidal method as previously described (Cardoso et al., 2011). Significant differences were considered when $P \leq 0.05$ or a trend if $0.05 < P \leq 0.10$. For all models, significant differences between time points were tested using Bonferroni adjustment for multiple comparisons. Data are reported as least squares mean (LSM)±standard error of the mean (SEM) unless otherwise stated.

The following results were obtained using the materials and methods described above for this Part III.

Intravenous Glucose Tolerance Test

Glucose AUC did not differ between treatment groups among all IVGTT (FIG. 1A-B). On the IVGTT performed at 12 h after treatment, plasma concentration of insulin was greater ($P \leq 0.05$) in the rbIL-8 group at 15 and 30 min after glucose infusion and tended to be greater ($P \leq 0.10$) at 45 min compared to the CTR group (FIG. 10A). On IVGTT performed on study d 10, rbIL-8 calves had greater ($P \leq 0.05$) plasma concentrations of insulin at 15 and 30 min after glucose infusion compared with their CTR counterparts (FIG. 10B). Compared to CTR calves, rbIL-8 calves attended to have a greater insulin AUC during IVGTT test conducted 12 hours after treatment (P≤0.10) and had greater (P≤0.05) insulin AUC during IVGTT test performed on study d 10 (FIG. 10A-B).

Insulin and Blood Metabolite Concentrations

No differences were observed in the plasma concentration of glucose and insulin between treatment groups (FIG. 11). Treatment with rbIL-8 increased (P≤0.01) BHB plasma concentrations particularly at study d 3 and 8 (FIG. 11). No differences were observed in plasma concentrations of NEFA between the two groups (FIG. 11).

FIG. 12 illustrates the dynamics of insulin, glucose, BHB and NEFA after treatment on d 1 (s.c.) and d 2 (i.v.). Treatment did affect the serum concentrations of glucose (P≤0.10), insulin (P≤0.05), BHB (P≤0.05) and NEFA (P≤0.01). Compared to CTR calves, rbIL-8-treated calves had a greater (P≤0.05) glucose concentration at 30 min after the first treatment on d 2 followed by an acute increase (P≤0.01) in insulin concentrations at 120 min. Plasma BHB concentration tended to be greater on d 2 at 30 min, and increased (P≤0.05) from 60 to 120 min after treatment in the rbIL-8 group compared with controls. Finally, greater (P≤0.05) concentrations of NEFA were observed at 360 min on d 2 in calves that were treated with rbIL-8 compared with controls.

Although an overall effect of treatment on plasma concentrations of PUN were not observed, an interaction between treatment and time was observed (P≤0.01). Calves treated with rbIL-8 greater (P≤0.05) concentrations of PUN in plasma on d 10 compared with controls (FIG. 13). Treatment by time interaction was also observed (P≤0.01) for haptoglobin concentrations, wherein calves treated with rbIL-8 had greater (P≤0.05) concentrations of haptoglobin in plasma on d 2 and d 3 compared with controls (FIG. 14).

Hemogram Parameters and Rectal Temperature

Results of daily, multi time-point monitoring of RT, and absolute numbers of white blood cells (WBC), lymphocytes (LYM), monocytes (MONO) and granulocytes (GRAN) are depicted in FIGS. 6 and 7. Treatment with rbIL-8 affected RT (P=0.03), WBC (P≤0.01), LYM (P≤0.01), MONO (P≤0.01), and GRAN (P≤0.01). Calves treated with rbIL-8 had increased (P≤0.05) RT at 60 and 120 min after the first treatment on d 2, and a trend was observed 30 min after the treatment on d 3. Moreover, RT was greater at d 8 (P≤0.05) and d 10 (P≤0.05), and tended to be greater at d 9 (P≤0.10) in the rbIL8-treated group compared with the CTR group (FIG. 15). Calves in the rbIL-8 treatment group had (P≤0.01) and tended to have (P≤0.10) greater counts of WBC at 240 and 360 min after the first treatment on d 1, and at 30 min before the first treatment on d 2, respectively (FIG. 16). Compared to controls, rbIL-8 calves tended to have (P≤0.10) greater LYM counts at 30 min after the first treatment on d 2 and at 30 min before the first treatment on d 4, and a significant increase (P≤0.05) was observed on d 10 (FIG. 16). Relative to controls, rbIL-8 calves tended to have (P≤0.10) and had greater (P≤0.05) counts of MONO at 240 and 360 min after the first treatment on d 1, respectively. Additionally, a trend (P≤0.10) was observed at 120 min after the first treatment on d 4, where rbIL-8 calves had greater MONO concentration than controls (FIG. 16). Finally, greater (P≤0.01) counts of GRAN was observed at 240 and 360 min after the first treatment on d 1 in the treatment group compared with the controls (FIG. 16).

Growth and Intake

No differences were detected in birth weight, BW at d 0, age at d 0 and final weight between the treatment and control groups (Table 5). However, a significant effect (P≤0.05) was found for BW, where CTR calves tended to be heavier (P≤0.10) at d 7 and d 10 compared with rbIL-8-treated calves (FIG. 17). Moreover, no differences were detected in milk consumption, MI, and starter intake between the rbIL-8-treated and CTR groups (Table 5). Therefore, ADG was smaller (P≤0.05) for rbIL-8-treated calves compared with CTR and feed efficiency tended to be smaller (P≤0.10) for rbIL-8 compared with CTR calves (Table 5).

TABLE 5

Birth weight, body weight at d 0 and d 10, age at d 0, and starter intake, milk consumption, total milk intake, average daily gain, and feed efficiency from d 1 to d 10 of Holstein bull calves treated with rbIL-8 (n = 10) and controls (n = 8). Results are reported as least squares mean (LSM) and standard error of the mean (SEM) unless otherwise stated.

| Treatment | CTR | | rbIL-8 | | |
| --- | --- | --- | --- | --- | --- |
| Variable | LSM | SEM | LSM | SEM | P-value |
| Birth weight, kg | 41.3[1] | 1.11 | 42.1[1] | 0.99 | 0.64 |
| BW day 0, kg | 53.6[1] | 3.36 | 55.8[1] | 3.00 | 0.62 |
| Age day 0, days | 31.9[1] | 1.45 | 31.4[1] | 1.30 | 0.80 |
| Final weight, kg | 60.5[1] | 3.87 | 61.0[1] | 3.46 | 0.92 |
| ADG, kg/d | 0.66 | 0.06 | 0.45 | 0.05 | 0.02 |
| Starter DMI, kg/d | 0.31 | 0.09 | 0.42 | 0.08 | 0.41 |
| Milk Consumption, L/d | 5.77 | 0.17 | 5.72 | 0.16 | 0.82 |
| Total MI, kg DM[2] | 7.73[1] | 0.41 | 7.53[1] | 0.37 | 0.74 |
| Total Starter Intake, kg | 2.85[1] | 0.80 | 2.29[1] | 0.71 | 0.61 |
| Feed efficiency[3] | 0.67 | 0.08 | 0.47 | 0.07 | 0.09 |

[1]Mean (ANOVA test).
[2]Total Milk Intake (MI, kg DM) was calculated assuming total milk solids of 13.5%.
[3]DMI includes milk intake and starter intake.

It will be recognized from the foregoing results that, based on findings of an effect of rbIL-8 on milk production discussed above, the studies in this Part III were performed to investigate one of the potential underlying physiological mechanisms through which rbIL-8 could enhance lactation performance, which is also demonstrated above. We determined that systemic treatment with rbIL-8 induced long-lasting peripheral insulin resistance in bull Holstein calves. In addition, rbIL-8 administration resulted in a decrease in ADG, elevated RT, increased haptoglobin, and altered blood metabolites and white blood cell counts.

In dairy cows, the onset of lactation is supported by dramatic metabolic adaptations that involve key metabolites, hormones and body tissues. Such coordinated metabolic changes that support a physiological state (e.g. lactation) are defined as homeorhesis (Bell and Bauman, 1997). Insulin resistance is described as a reduction in the biological response to insulin in peripheral tissues (De Koster and Opsomer, 2013) and is considered one of the major homeorhetic adaptations that postpartum cows experience to support milk and energy demands (Bell and Bauman, 1997; De Koster and Opsomer, 2013). Interestingly, it has been demonstrated that peripheral tissue insulin responses differ between beef and dairy cattle (Bossaert et al., 2009). In that study, Holstein-Friesian calves (dairy calves) were found to have lower insulin sensitivity compared with beef-breed calves, suggesting that the reduction in insulin sensitivity in the former may be a consequence of genetic selection for milk yield to support lactation (Bossaert et al., 2009).

As discussed above, we demonstrated that a single intra-uterine or intravenous administration shortly after parturition of rbIL-8 increased milk yield in a sustained manner in lactating Holstein cows. Although the cellular mechanism underlying the decrease in insulin response in early lactation is not clear, the present data indicates that rbIL-8 might induce insulin resistance. In this PART III, a metabolic test (IVGTT) showed that systemic treatments with rbIL-8 induced long-lasting insulin resistance in bull Holstein calves. Additionally, we showed that after the first treatment on d 2, rbIL-8 induced hyperglycemia that was reflected by an increase in serum insulin. In non-insulin resistant animals, insulin has anti-lipolytic and lypogenic effects. However, instead of identifying a depletion in NEFA, we observed that rbIL-8-treated calves had a higher serum concentration of NEFA (coincident with insulin elevation) compared with controls.

In mammals, the role of pro-inflammatory cytokines such as IL-8, IL-6, and TNF-α in altering the insulin response has been extensively studied (Kushibiki et al., 2000, Kobashi et al., 2009, Hardy et al., 2011). For instance, Holstein steers treated once daily for 12 d with rbTNF-α exhibited decreased peripheral insulin sensitivity when assessed with IVGTT and an intravenous insulin tolerance test (Kushibiki et al., 2000). To our knowledge, the effect of IL-8 on insulin action in dairy cattle has not been investigated. Results presented here for rbIL-8 on the development of insulin resistance are similar the effects of IL-8 on insulin resistance in humans. The expression of IL-8 in omental fat depots is 2.7-fold greater in obese humans that are insulin-resistant compared with obese patients classified as insulin-sensitive (Hardy et al., 2011). In support, the direct effect of IL-8 on the response to insulin was demonstrated in vitro, wherein exposure to IL-8 induced insulin resistance in human adipocytes by reducing the effect of the insulin-stimulated AKT pathway (Kobashi et al., 2009).

Insulin-receptor signaling has a direct effect on activation of the AKT pathway, which promotes GLUT4 translocation for glucose uptake, stimulates glycogen synthesis, and inhibits gluconeogenesis (Brockman, 1985, Stephens and Pilch, 1995, Barthel and Schmoll, 2003). In addition, the AKT pathway plays a central role in muscle hypertrophy and atrophy (Sandri, 2008). Its activation decreases muscle proteolysis by inhibiting the ubiquitin-proteasome pathway, which results in decreased muscle mobilization (Mann et al., 2016). Although PUN can be influenced by a variety of parameters (e.g., dehydration, dietary protein and energy intake, rumen degradability, and liver and kidney function), it is used as a blood marker to directly reflect the protein status of an animal. For instance, in fasted steers, increased muscle protein turnover to meet energy needs is associated with higher levels of PUN (Ward et al., 1992). Here, although an overall treatment effect on plasma PUN was not observed, a treatment by time interaction was observed, since on d 10, rbIL-8-treated calves had a higher concentration of PUN compared to controls.

Without intending to be constrained by any particular theory, in view of the data in this disclosure for the effects of rbIL-8 on altered insulin action, concomitant with reduced ADG and feed efficiency despite no changes in DMI, as well as increased serum concentrations of BHB and PUN, without intending to be constrained by any particular theory, it is considered that the reduced insulin response led to diminished AKT-phosphorylation (reducing its activity), which could promote the release of glucogenic and ketogenic amino acids from skeletal muscle to the blood stream. Thus, the elevated plasma BHB and PUN levels described for the first time herein could be due to a systemic rise in amino acid levels owing to increased muscle breakdown. Therefore, this activated mechanism of proteolysis might explain the decreased ADG in calves treated with rbIL-8 compared with controls.

In this Part III, the repeated administration of rbIL-8 caused several changes to the white blood cell population. Interleukin-8 is the main chemoattractant for neutrophils and can be produced by smooth muscle, epithelial cells, endothelial cells, and any cell of the innate immune system with toll-like receptors (Mitchell et al., 2003). In addition, cytokines are well-known promoters of white blood cell differentiation. Here, although rbIL-8 administration altered the blood GRAN concentration during treatments, a sustained alteration of GRAN was not observed. Nevertheless, a chronic shift in white blood cell counts (e.g., for LYM and MONO) was detected, a condition previously linked with obesity-related insulin resistance in humans (Harford et al., 2011). It has been demonstrated that infiltration of macrophages and T cells into peripheral tissues contributes to inflammation and alters insulin action there (Vozarova et al., 2002a, Kintscher et al., 2008, Harford et al., 2011). In addition, it has been shown that a high white blood cell count is associated with a decrease in insulin action and predicts the development of type 2 diabetes (Vozarova et al., 2002b). Thus, and again without intending to be bound by any particular interpretation, it could be hypothesized that rbIL-8 treatments induced activation of the immune system, which was reflected in the altered and elevated white blood cell population. As a result, immune cells might accumulate in peripheral tissues, diminishing the insulin response. Based on the effects rbIL-8 had on the blood immune cells in the present study, it is contemplated that the link between immunity and metabolism could explain the chronic alteration of the insulin response that we observed.

A marker of inflammation evaluated in this Part III was the plasma concentration of a member of acute-phase proteins. Haptoglobin is produced by the liver in response to a systemic increase in pro-inflammatory cytokines (Baumann et al., 1989). Here, we demonstrated that repeated administration of rbIL-8 into bull calves induced a significant increase in plasma haptoglobin during the treatment period. Therefore, considering together the detected increases of haptoglobin, RT, and blood cell counts in calves treated with rbIL-8, and without intending to be bound by any particular theory, it is considered that rbIL-8 elicited those effects by acting as an inflammatory stimulus.

Based on our finding of rbIL-8 enhancing milk yield in lactating cows combined with the results presented in this Part III, and again without intending to be bound by any particular view, it is considered that rbIL-8 promotes insulin resistance in lactating dairy cows to benefit the homeorhetic shift that occurs during the transition from gestation to lactation to support milk production.

References for Part III

REFERENCES

Barthel, A. and D. Schmoll. 2003. Novel concepts in insulin regulation of hepatic gluconeogenesis. Am J Physiol Endocrinol Metab 285(4):E685-692.

Baumann, H., K. R. Prowse, S. Marinkovic, K. A. Won, and G. P. Jahreis. 1989. Stimulation of hepatic acute phase response by cytokines and glucocorticoids. Ann N Y Acad Sci 557:280-295, discussion 295-286.

Bell, A. W. 1995. Regulation of organic nutrient metabolism during transition from late pregnancy to early lactation. J Anim Sci 73(9):2804-2819.

Bell, A. W. and D. E. Bauman. 1997. Adaptations of glucose metabolism during pregnancy and lactation. J Mammary Gland Biol Neoplasia 2(3):265-278.

Bicalho, M. L., F. S. Lima, E. K. Ganda, C. Foditsch, E. B. Meira, Jr., V. S. Machado, A. G. Teixeira, G. Oikonomou, R. O. Gilbert, and R. C. Bicalho. 2014. Effect of trace mineral supplementation on selected minerals, energy metabolites, oxidative stress, and immune parameters and its association with uterine diseases in dairy cattle. J Dairy Sci 97(7):4281-4295.

Bossaert, P., J. L. Leroy, S. De Campeneere, S. De Vliegher, and G. Opsomer. 2009. Differences in the glucose-induced insulin response and the peripheral insulin responsiveness between neonatal calves of the Belgian Blue, Holstein-Friesian, and East Flemish breeds. J Dairy Sci 92(9):4404-4411.

Brockman, R. P. 1985. Role of insulin in regulating hepatic gluconeogenesis in sheep. Can J Physiol Pharmacol 63(11):1460-1464.

Cardoso, F. C., W. Sears, S. J. LeBlanc, and J. K. Drackley. 2011. Technical note: Comparison of 3 methods for analyzing areas under the curve for glucose and nonesterified fatty acids concentrations following epinephrine challenge in dairy cows. Journal of Dairy Science 94(12): 6111-6115.

De Koster, J. D. and G. Opsomer. 2013. Insulin Resistance in Dairy Cows. Vet Clin N Am-Food A 29(2):299-+.

Hardy, O. T., R. A. Perugini, S. M. Nicoloro, K. Gallagher-Dorval, V. Puri, J. Straubhaar, and M. P. Czech. 2011. Body mass index-independent inflammation in omental adipose tissue associated with insulin resistance in morbid obesity. Surg Obes Relat Dis 7(1):60-67.

Harford, K. A., C. M. Reynolds, F. C. McGillicuddy, and H. M. Roche. 2011. Fats, inflammation and insulin resistance: insights to the role of macrophage and T-cell accumulation in adipose tissue. Proc Nutr Soc 70(4):408-417.

Herdt, T. H. 2000. Ruminant adaptation to negative energy balance—Influences on the etiology of ketosis and fatty liver. Vet Clin N Am-Food A 16(2):215-+.

Kintscher, U., M. Hartge, K. Hess, A. Foryst-Ludwig, M. Clemenz, M. Wabitsch, P. Fischer-Posovszky, T. F. Barth, D. Dragun, T. Skurk, H. Hauner, M. Bluher, T. Unger, A. M. Wolf, U. Knippschild, V. Hombach, and N. Marx. 2008. T-lymphocyte infiltration in visceral adipose tissue: a primary event in adipose tissue inflammation and the development of obesity-mediated insulin resistance. Arterioscler Thromb Vasc Biol 28(7): 1304-1310.

Kobashi, C., S. Asamizu, M. Ishiki, M. Iwata, I. Usui, K. Yamazaki, K. Tobe, M. Kobayashi, and M. Urakaze. 2009. Inhibitory effect of IL-8 on insulin action in human adipocytes via MAP kinase pathway. J Inflamm (Lond) 6:25.

Koltes, D. A. and D. M. Spurlock. 2011. Coordination of lipid droplet-associated proteins during the transition period of Holstein dairy cows. Journal of Dairy Science 94(4): 1839-1848.

Kushibiki, S., K. Hodate, Y. Ueda, H. Shingu, Y. Mori, T. Itoh, and Y. Yokomizo. 2000. Administration of recombinant bovine tumor necrosis factor-alpha affects intermediary metabolism and insulin and growth hormone secretion in dairy heifers. J Anim Sci 78(8):2164-2171.

Mann, S., D. V. Nydam, A. Abuelo, F. A. L. Yepes, T. R. Overton, and J. J. Wakshlag. 2016. Insulin signaling, inflammation, and lipolysis in subcutaneous adipose tissue of transition dairy cows either overfed energy during the prepartum period or fed a controlled-energy diet. Journal of Dairy Science 99(8):6737-6752.

Mitchell, G. B., B. N. Albright, and J. L. Caswell. 2003. Effect of interleukin-8 and granulocyte colony-stimulating factor on priming and activation of bovine neutrophils. Infection and Immunity 71(4):1643-1649.

Reynolds, C. K., P. C. Aikman, B. Lupoli, D. J. Humphries, and D. E. Beever. 2003. Splanchnic metabolism of dairy cows during the transition from late gestation through early lactation. Journal of Dairy Science 86(4):1201-1217.

Sandri, M. 2008. Signaling in muscle atrophy and hypertrophy. Physiology (Bethesda) 23:160-170.

Stephens, J. M. and P. F. Pilch. 1995. The metabolic regulation and vesicular transport of GLUT4, the major insulin-responsive glucose transporter. Endocr Rev 16(4): 529-546.

Vozarova, B., N. Stefan, R. Hanson, R. S. Lindsay, C. Bogardus, P. A. Tataranni, C. Metz, and R. Bucala. 2002a. Plasma concentrations of macrophage migration inhibitory factor are elevated in Pima Indians compared to Caucasians and are associated with insulin resistance. Diabetologia 45(12): 1739-1741.

Vozarova, B., C. Weyer, R. S. Lindsay, R. E. Pratley, C. Bogardus, and P. A. Tataranni. 2002b. High white blood cell count is associated with a worsening of insulin sensitivity and predicts the development of type 2 diabetes. Diabetes 2002; 51:455-461pmid: 11812755.

Ward, J. R., D. M. Henricks, T. C. Jenkins, and W. C. Bridges. 1992. Serum Hormone and Metabolite Concentrations in Fasted Young Bulls and Steers. Domestic Animal Endocrinology 9(2):97-103.

Williamson, D. H. and J. Mellanby. 1974. D-(−)-3-hydroxybutyrate. Pages 1836-1840 in Methods of Enzymatic Analysis. H. U. Bergmeyer, ed. Academic Press, London, UK.

Part IV

This Example demonstrates an increase in dry matter intake using intra-uterine and intravenous administrations of IL-8, as demonstrated in Part IV FIGS. 18-20.

While the invention has been described through specific embodiments, routine modifications will be apparent to those skilled in the art and such modifications are intended to be within the scope of the present invention.

The invention claimed is:

1. A method for i) improving health of a non-human female mammal, and/or ii) increasing milk production and/or increasing fat content of milk produced by a non-human female mammal, and/or iii) increasing dry matter intake of a non-human female mammal, and/or iv) producing insulin resistance in a non-human female mammal, the method comprising administering to the non-human female mammal an effective amount of Interleukin-8 (IL-8) such that at least i), ii), iii), iv), or a combination thereof occurs subsequent to the administration, wherein the non-human female mammal is within twenty weeks after parturition when the IL-8 is administered.

2. The method of claim 1, wherein the administration of the IL-8 is an intrauterine administration or a systemic administration.

3. The method of claim 2, wherein the systemic administration is an intravenous administration.

4. The method of claim 1, wherein administering the IL-8 is performed only a single time, and wherein at least the amount of milk produced by the non-human female mammal is increased.

5. The method of claim 2, wherein administering the IL-8 is performed only a single time, and wherein at least the amount of milk produced by the non-human female mammal is increased.

6. The method of claim 3, wherein administering the IL-8 is performed only a single time, and wherein at least the amount of milk produced by the non-human female mammal is increased.

7. The method of claim 6, wherein the non-human female mammal is a bovine female mammal.

8. The method of claim 7, wherein the non-human female mammal is a dairy cow.

9. The method of claim 1, wherein the non-human female mammal is a member of a population of non-human female mammals of the same species, the method further comprising administering the IL-8 to other members of the population such that i), ii), iii), iv), or a combination thereof occurs in the other members of the population subsequent to the administration, wherein the other members of the population are within twenty weeks after parturition when the IL-8 is administered.

10. The method of claim 9, wherein at least ii) occurs in the other members subsequent to the administration.

11. The method of claim 9, wherein the non-human mammal is a female bovine mammal.

12. The method of claim 11, wherein the non-human female mammal is a dairy cow.

* * * * *

SEQUENCE LISTING

<160> NUMBER OF SEQ ID NOS: 14

<210> SEQ ID NO 1
<211> LENGTH: 101
<212> TYPE: PRT
<213> ORGANISM: Bos taurus

<400> SEQUENCE: 1

Met Thr Ser Lys Leu Ala Val Ala Leu Leu Ala Ala Phe Leu Leu Ser
1               5                   10                  15

Ala Ala Leu Cys Glu Ala Ala Val Leu Ser Arg Met Ser Thr Glu Leu
            20                  25                  30

Arg Cys Gln Cys Ile Lys Thr His Ser Thr Pro Phe His Pro Lys Phe
        35                  40                  45

Ile Lys Glu Leu Arg Val Ile Glu Ser Gly Pro His Cys Glu Asn Ser
    50                  55                  60

Glu Ile Ile Val Lys Leu Thr Asn Gly Asn Glu Val Cys Leu Asn Pro
65                  70                  75                  80

Lys Glu Lys Trp Val Gln Lys Val Val Gln Val Phe Val Lys Arg Ala
                85                  90                  95

Glu Lys Gln Asp Pro
            100

<210> SEQ ID NO 2
<211> LENGTH: 101
<212> TYPE: PRT
<213> ORGANISM: Bubalus bubalus

<400> SEQUENCE: 2

Met Thr Ser Lys Leu Ala Val Ala Leu Leu Ala Ala Phe Leu Leu Ser
1               5                   10                  15

Ala Ala Leu Cys Glu Ala Ala Val Leu Ser Arg Met Ser Thr Glu Leu
            20                  25                  30

Arg Cys Gln Cys Ile Lys Thr His Ser Thr Pro Phe His Pro Lys Phe
        35                  40                  45

Ile Lys Glu Leu Arg Val Ile Glu Ser Gly Pro His Cys Glu Asn Ser
    50                  55                  60

Glu Ile Ile Val Lys Leu Thr Asn Gly Lys Glu Val Cys Leu Asn Pro
65                  70                  75                  80

Lys Glu Lys Trp Val Gln Lys Val Val Gln Val Phe Val Lys Arg Ala
                85                  90                  95

Glu Lys Gln Asp Pro
            100

<210> SEQ ID NO 3
<211> LENGTH: 101
<212> TYPE: PRT
<213> ORGANISM: Cervus elephus

<400> SEQUENCE: 3

Met Thr Ser Lys Leu Ala Val Ala Leu Leu Ala Ala Phe Leu Leu Ser
1               5                   10                  15

Ala Ala Leu Cys Glu Ala Ala Val Leu Ser Arg Met Ser Thr Glu Leu
            20                  25                  30

Arg Cys Gln Cys Ile Lys Thr His Ser Thr Pro Phe His Pro Lys Phe
        35                  40                  45

Ile Lys Glu Leu Arg Val Ile Glu Ser Gly Pro His Cys Glu Asn Ser
    50                  55                  60

Glu Ile Ile Val Lys Leu Thr Asn Gly Lys Glu Val Cys Leu Asn Pro
65                  70                  75                  80

Lys Glu Lys Trp Val Gln Lys Val Val Glu Val Phe Val Lys Arg Ala
                85                  90                  95

Glu Lys Gln Asp Pro
            100

<210> SEQ ID NO 4
<211> LENGTH: 101
<212> TYPE: PRT
<213> ORGANISM: Ovis aries

<400> SEQUENCE: 4

Met Thr Ser Lys Leu Ala Val Ala Leu Leu Ala Ala Phe Leu Leu Ser
1               5                   10                  15

Ala Ala Leu Cys Glu Ala Ala Val Leu Ser Arg Met Ser Thr Glu Leu
            20                  25                  30

Arg Cys Gln Cys Ile Lys Thr His Ser Thr Pro Phe His Pro Lys Phe
        35                  40                  45

Ile Lys Glu Leu Arg Val Ile Glu Ser Gly Pro His Cys Glu Asn Ser
    50                  55                  60

Glu Ile Ile Val Lys Leu Thr Asn Gly Lys Glu Val Cys Leu Asp Pro
65                  70                  75                  80

Lys Glu Lys Trp Val Gln Lys Val Val Gln Ala Phe Leu Lys Arg Ala
                85                  90                  95

Glu Lys Gln Asp Pro
            100

<210> SEQ ID NO 5
<211> LENGTH: 97
<212> TYPE: PRT
<213> ORGANISM: Equus caballus

<400> SEQUENCE: 5

Met Thr Ser Lys Leu Ala Val Ala Leu Leu Ala Val Phe Leu Leu Ser
1               5                   10                  15

Ala Ala Leu Cys Glu Ala Ala Val Val Ser Arg Ile Thr Ala Glu Leu
            20                  25                  30

Arg Cys Gln Cys Ile Lys Thr His Ser Lys Pro Phe Asn Pro Lys Leu
        35                  40                  45

Ile Lys Glu Met Arg Val Ile Glu Ser Gly Pro His Cys Glu Asn Ser
    50                  55                  60

Glu Ile Ile Val Lys Leu Val Asn Gly Ala Glu Val Cys Leu Asn Pro
65                  70                  75                  80

His Thr Lys Trp Val Gln Ile Ile Val Gln Ala Phe Leu Lys Arg Thr
                85                  90                  95

Glu

<210> SEQ ID NO 6
<211> LENGTH: 99
<212> TYPE: PRT
<213> ORGANISM: Homo sapiens

<400> SEQUENCE: 6

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
            85                  90                  95

Glu Asn Ser

<210> SEQ ID NO 7
<211> LENGTH: 101
<212> TYPE: PRT
<213> ORGANISM: Canis lupus familiaris

<400> SEQUENCE: 7

Met Thr Ser Lys Leu Ala Val Ala Leu Leu Ala Ala Phe Val Leu Ser
1               5                   10                  15

Ala Ala Leu Cys Glu Ala Ala Val Leu Ser Arg Val Ser Ser Glu Leu
            20                  25                  30

Arg Cys Gln Cys Ile Lys Thr His Ser Thr Pro Phe His Pro Lys Tyr
        35                  40                  45

Ile Lys Glu Leu Arg Val Ile Asp Ser Gly Pro His Cys Glu Asn Ser
    50                  55                  60

Glu Ile Ile Val Lys Leu Phe Asn Gly Asn Glu Val Cys Leu Asp Pro
65                  70                  75                  80

Lys Glu Lys Trp Val Gln Lys Val Val Gln Ile Phe Leu Lys Lys Ala
                85                  90                  95

Glu Lys Gln Asp Pro
            100

<210> SEQ ID NO 8
<211> LENGTH: 101
<212> TYPE: PRT
<213> ORGANISM: Felus catus

<400> SEQUENCE: 8

Met Thr Ser Lys Leu Val Val Ala Leu Leu Ala Ala Phe Met Leu Ser
1               5                   10                  15

Ala Ala Leu Cys Glu Ala Ala Val Leu Ser Arg Ile Ser Ser Glu Leu
            20                  25                  30

Arg Cys Gln Cys Ile Lys Thr His Ser Thr Pro Phe Asn Pro Lys Leu
        35                  40                  45

Ile Lys Glu Leu Thr Val Ile Asp Ser Gly Pro His Cys Glu Asn Ser
    50                  55                  60

Glu Ile Ile Val Lys Leu Val Asn Gly Lys Glu Val Cys Leu Asp Pro
65                  70                  75                  80

Lys Gln Lys Trp Val Gln Lys Val Val Glu Ile Phe Leu Lys Lys Ala
                85                  90                  95

Glu Lys Gln Asn Ala
            100

<210> SEQ ID NO 9
<211> LENGTH: 100
<212> TYPE: PRT
<213> ORGANISM: artificial sequence
<220> FEATURE:
<223> OTHER INFORMATION: IL-8 consensus
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid -continued

```
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 9

Met Thr Ser Lys Leu Ala Val Ala Leu Leu Ala Phe Leu Leu Ser
1               5                   10                  15

Ala Ala Leu Cys Glu Ala Ala Val Leu Ser Arg Xaa Ser Xaa Glu Leu
                20                  25                  30

Arg Cys Gln Cys Ile Lys Thr His Ser Thr Pro Phe His Pro Lys Phe
            35                  40                  45

Ile Lys Glu Leu Arg Val Ile Glu Ser Gly Pro His Cys Glu Asn Ser
        50                  55                  60

Glu Ile Ile Val Lys Leu Xaa Asn Gly Lys Val Cys Leu Xaa Pro Lys
65                  70                  75                  80

Glu Lys Trp Val Gln Lys Val Val Gln Val Phe Leu Lys Arg Ala Glu
                85                  90                  95

Lys Gln Asp Pro
            100

<210> SEQ ID NO 10
<211> LENGTH: 101
<212> TYPE: PRT
<213> ORGANISM: Bos taurus

<400> SEQUENCE: 10

Met Thr Ser Lys Leu Ala Val Ala Leu Leu Ala Phe Leu Leu Ser
1               5                   10                  15

Ala Ala Leu Cys Glu Ala Ala Val Leu Ser Arg Met Ser Thr Glu Leu
                20                  25                  30

Arg Cys Gln Cys Ile Lys Thr His Ser Thr Pro Phe His Pro Lys Phe
            35                  40                  45

Ile Lys Glu Leu Arg Val Ile Glu Ser Gly Pro His Cys Glu Asn Ser
        50                  55                  60

Glu Ile Ile Val Lys Leu Thr Asn Gly Asn Glu Val Cys Leu Asn Pro
65                  70                  75                  80

Lys Glu Lys Trp Val Gln Lys Val Val Gln Val Phe Val Lys Arg Ala
                85                  90                  95

Glu Lys Gln Asp Pro
            100

<210> SEQ ID NO 11
<211> LENGTH: 32
<212> TYPE: DNA
<213> ORGANISM: artificial sequence
<220> FEATURE:
<223> OTHER INFORMATION: primer

<400> SEQUENCE: 11
cggcgccgtg ctgtctcgta tgtccaccga ac                                    32

<210> SEQ ID NO 12
<211> LENGTH: 31
<212> TYPE: DNA
<213> ORGANISM: artificial sequence
<220> FEATURE:
```

```
<223> OTHER INFORMATION: primer

<400> SEQUENCE: 12
gctcgagtca cggatcttgt ttttctgcac g                                31

<210> SEQ ID NO 13
<211> LENGTH: 9
<212> TYPE: PRT
<213> ORGANISM: Bos taurus

<400> SEQUENCE: 13

Ala Val Leu Ser Arg Met Ser Thr Glu
1               5

<210> SEQ ID NO 14
<211> LENGTH: 119
<212> TYPE: PRT
<213> ORGANISM: artificial sequence
<220> FEATURE:
<223> OTHER INFORMATION: His-tagged bovine IL-8

<400> SEQUENCE: 14

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Asp Leu Tyr Asp Asp Asp Lys Ala Val Leu Ser Arg Met Ser Thr
            35                  40                  45

Glu Leu Arg Cys Gln Cys Ile Lys Thr His Ser Thr Pro Phe His Pro
50                  55                  60

Lys Phe Ile Lys Glu Leu Arg Val Ile Glu Ser Gly Pro His Cys Glu
65                  70                  75                  80

Asn Ser Glu Ile Ile Val Lys Leu Thr Asn Gly Asn Glu Val Cys Leu
                85                  90                  95

Asn Pro Lys Glu Lys Trp Val Gln Lys Val Val Gln Val Phe Val Lys
            100                 105                 110

Arg Ala Glu Lys Gln Asp Pro
            115
```